US007820882B2

(12) United States Patent
Dubcovsky et al.

(10) Patent No.: US 7,820,882 B2
(45) Date of Patent: Oct. 26, 2010

(54) NAC FROM WHEAT FOR INCREASING GRAIN PROTEIN CONTENT

(75) Inventors: Jorge Dubcovsky, Davis, CA (US); Tzion Fahima, Kiryat-Tivon (IL); Cristobal Uauy, Davis, CA (US); Assaf Distelfeld, Kiryat-Tivon (IL)

(73) Assignees: The Regents of the University of California, Oakland, CA (US); Carmel-Haifa University Economic Corp., Mount Carmel, Haifa (IL)

( * ) Notice: Subject to any disclaimer, the term of this patent is extended or adjusted under 35 U.S.C. 154(b) by 51 days.

(21) Appl. No.: 11/920,387

(22) PCT Filed: May 11, 2006

(86) PCT No.: PCT/US2006/018686

§ 371 (c)(1),
(2), (4) Date: Nov. 13, 2007

(87) PCT Pub. No.: WO2006/124752

PCT Pub. Date: Nov. 23, 2006

(65) Prior Publication Data

US 2009/0205070 A1    Aug. 13, 2009

Related U.S. Application Data

(60) Provisional application No. 60/680,603, filed on May 12, 2005.

(51) Int. Cl.
*A01H 5/00* (2006.01)
*C12N 15/82* (2006.01)
*C07H 21/04* (2006.01)

(52) U.S. Cl. .................. 800/298; 800/278; 800/285; 800/286; 800/295; 800/320.3; 435/320.1; 435/419; 435/468; 536/23.6; 536/22.1

(58) Field of Classification Search ................ None
See application file for complete search history.

(56) References Cited

U.S. PATENT DOCUMENTS

2004/0019927 A1    1/2004  Sherman et al.
2004/0045049 A1    3/2004  Zhang et al.
2004/0123343 A1    6/2004  La Rosa et al.

FOREIGN PATENT DOCUMENTS

EP          1 586 652 A      10/2005
WO      WO 03/000898 A      1/2003

OTHER PUBLICATIONS

Xie et al. Arabidopsis NAC1 transduces auxin signal downstream of TIR1 to promoter lateral root development. (2000) Genes & Development; vol. 14; pp. 3024-3036.*

Olsen et al. NAC transcription factors: structurally distinct, functionally divers. (2005) Trends in Plant Science; vol. 10; pp. 79-87.*

Olsen, A.N., et al.; "NAC Transcription Factors: Structurally Distinct, Functionality Diverse," *Trends in Plant Science*, Feb. 2005, vol. 10, No. 2, pp. 79-87.

Xie, Q. et al., "Arabidopis NAC1 Transduces Auxin Signal Downstream of T1R1 to Promote Lateral Root Development," *Genes & Development*, Dec. 1, 2000, vol. 14, 23 pages.

Chee, P.W., et al., "Evaluation of a High Grain Protein QTL from *Triticum turgidum* L. var. *dicoccoides* in an Adapted Durum Wheat Background," *Crop Science*, vol. 41(2), pp. 295-301 (Mar. 2001).

Distelfeld, A., et al., "Microcolinearity between a 2-cM region encompassing the grain protein content locus Gpc-6B1 on wheat chromosome 6B and a 350-kb region on rice chromosome 2," *Functional and Integrative Genomics*, vol. 4(1), pp. 59-66 (Mar. 2004).

Lin, J-F., et al., "Molecular events in senescing *Arabidopsis* leaves," *The Plant Journal*, vol. 39(4), pp. 612-628 (Aug. 1, 2004).

Miao, Y., et al., "Targets of the WRKY53 transcription factor and its role during leaf senescence in *Arabidopsis*," *Plant Molecular Biology*, vol. 55(6), pp. 853-867 (Aug. 1, 2004).

Olmos, S., et al., "Precise mapping of a locus affecting grain protein content in durum wheat," *Theoretical and Applied Genetics*, vol. 107(7), pp. 1243-1251 (Nov. 2003).

Sasaki, T., et al., "Oryza sativa Japonica Group genomic DNA, chromosome 7, BAC clone:OJ1092_A07," Database EMBL [Online], EBI Accession No. EMBL:AP003866, 12 pgs. (Jul. 10, 2001).

Tran, L-S., et al., "Isolation and Functional Analysis of Arabidopsis Stress-Inducible NAC Transcription Factors That Bind to a Drought-Responsive cis-Element in the *early responsive to dehydration stress 1* Promoter," *The Plant Cell*, vol. 16(9), pp. 2481-2498 (Sep. 2004).

Uauy, C., et al., "A NAC Gene Regulating Senescence Improves Grain Protein, Zinc, and Iron Content in Wheat," *Science*, vol. 314(5803), pp. 1298-1301 (Nov. 24, 2006).

Uauy, C., et al. "The high grain protein content gene Gpc-B1 accelerates senescence and has pleiotropic effects on protein content in wheat," *Journal of Experimental Botany*, vol. 57(11), pp. 2785-2794 (Aug. 2006, Advance Access Pub: Jul. 9, 2006).

Wabiko, H., et al., "Isolation of the leaf senescence-associated NAC-family gene from rice," Plant Biology (Rockville), & Annual Meeting of the American Society of Plant Biologists on Plant Biology, 1 pg., Abstract #345 (Jan. 1, 2002).

* cited by examiner

*Primary Examiner*—Cathy Kingdon Worley
(74) *Attorney, Agent, or Firm*—Townsend and Townsend and Crew LLP

(57) ABSTRACT

The present invention provides wheat NAC nucleic acids and proteins that modulate grain protein content and senescence in plants. Overexpression of a NAC coding sequence can accelerate senescence and increase grain protein content and inhibition of expression can delay senescence. The invention also provides methods of using the nucleic acids to produce transgenic plants with altered grain protein content or senescence.

15 Claims, 13 Drawing Sheets

FIG. 2

```
Td  DIC protein (SEQ ID NO: 16)   LNKLFQN--KDRYRQYGLWE
Td  LDN protein (SEQ ID NO: 18)   LNKLFQN--NDRYRQYGLWE
Os  BX000498                      LNKIFIT--KDKYRQYGLWE
At  NP_172459                     VNKLYLN-HSDKYRQYGLWE
At  AAD15570                      MNKLYVNPLQDRFRQYGLWD
At  AAS99719                      MNKLYVNPLQDRFRQYGLWD
At  CAB79353                      INKLYIG-HPDRFRQYGLWE
Os  XP_507326                     VNRLYIN-HPDRFRQYGLWE
At  XP_483712                     VNRLYIN-HPDRFRQYGLWE
At  NP_172460                     INNLYQN-HPDRFRQYGLWE
At  NP_172462                     VNRVLVH-HQDRFRQYGLWK
```

FIG. 5
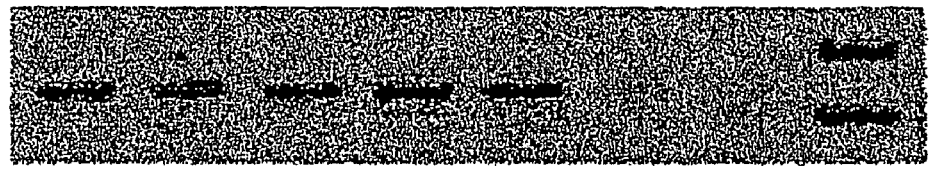
Actin
OsNAC

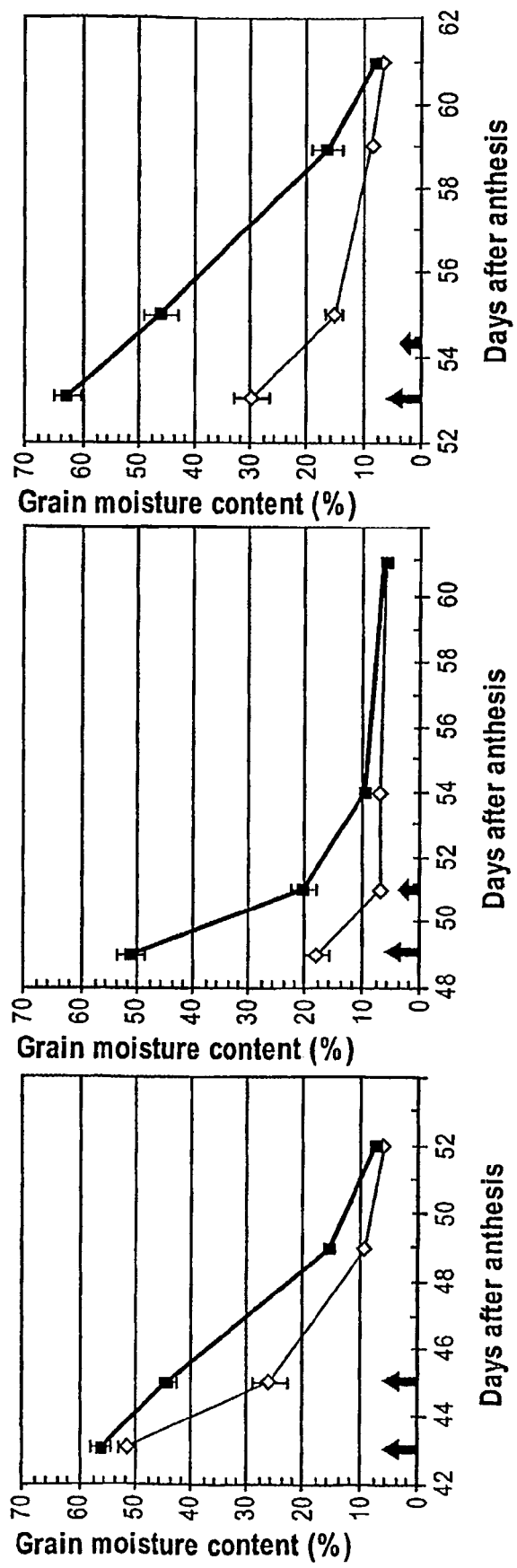

SEQUENCE LISTING

```
<160> NUMBER OF SEQ ID NOS: 31

<210> SEQ ID NO 1
<211> LENGTH: 3542
<212> TYPE: DNA
<213> ORGANISM: Triticum turgidum
<220> FEATURE:
<223> OTHER INFORMATION: functional Triticum turgidum var. dicoccoides
      WNAC-B1a (DIC) allele (BAC 916017) genomic DNA
<220> FEATURE:
<221> NAME/KEY: 5'UTR
<222> LOCATION: (1)..(1000)
<220> FEATURE:
<221> NAME/KEY: CDS
<222> LOCATION: join(1001..1241, 1457..1794, 1904..2542)
<223> OTHER INFORMATION: functional Triticum turgidum var. dicoccoides
      WNAC-B1a (DIC) allele predicted protein
<220> FEATURE:
<221> NAME/KEY: exon
<222> LOCATION: (1001)..(1241)
<220> FEATURE:
<221> NAME/KEY: intron
<222> LOCATION: (1242)..(1456)
<220> FEATURE:
<221> NAME/KEY: exon
<222> LOCATION: (1457)..(1794)
<220> FEATURE:
<221> NAME/KEY: intron
<222> LOCATION: (1795)..(1903)
<220> FEATURE:
<221> NAME/KEY: exon
<222> LOCATION: (1904)..(2542)
```

```
<220> FEATURE:
<221> NAME/KEY: 3'UTR
<222> LOCATION: (2543)..(3542)
<220> FEATURE:
<221> NAME/KEY: polyA_signal
<222> LOCATION: (2822)..(2830)
<223> OTHER INFORMATION: putative polyadenylation signal
<220> FEATURE:
<221> NAME/KEY: primer_bind
<222> LOCATION: (3013)..(3032)
<223> OTHER INFORMATION: primer designed for TA(30) microsatellite locus
<220> FEATURE:
<221> NAME/KEY: primer_bind
<222> LOCATION: (3229)..(3248)
<223> OTHER INFORMATION: primer designed for TA(30) microsatellite locus

<400> SEQUENCE: 1
cggtggcgag ttcgagtcct gaggagagca ttattttttac ccgttttttgg ttttgcgagc      60 gttttatgtt ctctggtttg cactcttcat gggccggccc agcgcggggc gctgcaggcg     120
tcaggagcgc caacgggcgc ctgcagcgcc gtataggagc tccctacatg tccttctaac     180
catccaatca cagattggtt tgcttttttt gacgaactga tttgttttta attgtttgaa     240
ttgcttacca catgtttcac gtggtctgac gaactggttg ggttcataag gtgtgtgaaa     300
tgaggtcacg atgttaaaag aggtacccctt tgattagttg cttcccgaga acatctgtg      360 ctaaaaaaga gagcaagaag aggtcacgat gttggtatca tgcggcccac cagaatatgc     420
tgaaatggag ctcagcacgg gccaacaaaa tacctagccc aggaagctac gaagccggtg     480
caaactacca ggccttaagc cgaaggatgg ggcaaggtga accgtgtccg gtccggctcc     540
cccgcgtccg cccgcataga aggaagtggc ggaatactct tcccatccca gaagaaaaaaa     600 taaggtagga agcggaatgg gtggccgtgg tcgcgcgagc ttgcgccgtc cggtggcgat     660
ctgacacgcg gtacgagcgg cggccggcat acgtgtccag cggcgacggg cccgcggccc     720
cgggctaggt acaacggtgc cgtatttctc ccctgctctc ctcgccacgg tttcacagcc     780
gccccgaaac caccagagct cccacagcag atcactcgcc cgcctctcct ctccttcctc     840
ccaaccgtcg ctgtaacaaa tcccactccg ttccttcctt cacactacct agaagctttg     900
gcagttgagt taggtgccca ccacaggggt gctctggtgg gatcatctgg tgtgtttgtt     960
ggtagctagc tagctagggg aagaagatct gatgaggtcc atgggcagct ccgactcatc    1020
ttccggctcg gcgcaaaaag caacgcggta tcaccatcag catcagccgc cgcctccgca    1080
gcggggctcg gcgccggagc tcccgccggg cttccggttc cacccgacgg acgaggagct    1140
ggtggtgcac tacctcaaga agaaggccga caaggcgccg ctccccgtca acatcatcgc    1200
cgaggtggat ctctacaagt tcgacccatg ggagctcccc ggtatgttat gtctatctcg    1260
tcggccggcc gtgcttactt tatcaagcgc cgcaaatttt cggtgcaatt aaataatcga    1320
ataatccatc catctcatgc ttatactcct gtgcacaagt agtatttta tattcttcca     1380 gtacacatgt gtgtagatgg tttatgtatg tgatcctgtc gtgcttgttc atgcgctcgg    1440
gatccggatc catcagagaa ggcgaccatc ggggagcagg agtggtactt cttcagcccg    1500
cgcgaccgca agtaccccaa cggcgcgcgg ccgaaccggg cggcgacgtc ggggtactgg    1560
aaggccaccg gcacggacaa gcctatcctg gcctcgggga cggggtgcgg cctggtccgg    1620
gagaagctcg gcgtcaagaa ggcgctcgtg ttctaccgcg ggaagccgcc caagggcctc    1680
aaaaccaact ggatcatgca cgagtaccgc ctcaccgacg catctggctc caccaccgcc    1740
accaaccgac cgccgccggt gaccggcggg agcagggctg ctgcctctct cagggtacgt    1800
acacgtgtcg atcgcacggt ctagcagtat ttaattgctc tccagcttaa ttagggtatt    1860
```

```
gttgatggtt gatgaagtta attatgtacc gtcgtctcat cagttggacg actgggtgct      1920
gtgccgcatc tacaagaaga tcaacaaggc cgcggccggc gatcagcaga ggaacacgga      1980
gtgcgaggac tccgtggagg acgcggtcac cgcgtacccg ctctatgcca cggcgggcat      2040
gaccggtgca ggtgcgcatg cagcaacta cgcttcacct tcactgctcc atcatcagga      2100
cagccatttc ctggacggcc tgttcacagc agacgacgcc ggcctctcgg cgggcgccac      2160
ctcgctgagc cacctagcag cggcggcgag ggcaagcccg gctccgacca aacagtttct      2220
cgccccgtcg tcttcgaccc cgttcaactg gctcgatgcg tcaccagtcg gcatcctccc      2280
acaggcaagg aattttcctg ggtttaacag gagcagaaac gtcggcaata tgtcgctgtc      2340
atcgacggcc gacatggctg gcgcagtgga caacggtgga ggcaatgcgg tgaacgccat      2400
gtctacctat cttcccgtgc aagacgggac gtaccatcag cagcatgtca tcctcggcgc      2460
tccgctggtg ccagaagccg ccgccgccac ctctggattc cagcatcccg ttcaaatatc      2520
cggcgtgaac tggaatccct gatcaaatga tatgaacacc acatcgggc atgcacgcac      2580 gcatgcataa cttttgcaag tcgtacaaca ttgctagcca gtagttgttg cagtttgtgg      2640
tagtcccttt cagtgagcac tgagtagttg catgcacatc accactgcat ggatatatat      2700
ggctgcattg caccatgggc acgtacttgt gcgaacttgc tagccatata tatagtagta      2760
caatagctag gagtattttc gaagtacaaa aaaatcataa catagtactc catatatatt      2820
gtaataaata tatttttag atatatatga gtatgataat agcttcatat gcatatacta      2880
tattgtagtg catatagtaa atatatatgc agttgattac aaaccccagt cagatacaat      2940
ttttggccgg gtctagctac ttatcatgta taaatagggg tgtatgtaaa tgagcaacgc      3000
atggtaactg catgcacgcg tatcattgat ctatatggac gtacactgta aactttttt      3060 tttcatgaat aagatttgcg aactagtatg tcgcagtggt ttagttatta tgtgaatggc      3120
ccttatatat atatatatat atatatatat atatatatat atatgttcga aaatgtgtg      3180 ttatctcctt aatttcattt ttgaaagaaa aacatcatct tgacagttgt cacatgtcca      3240
agctgtccgt ggatgcctcc ctaatcgccg ccgcgctcat gtaagttcta tgttgccttg      3300
ccaccacact taaactaggg aaagatatgt gaacgtaaga cataagtaca tctctatttc      3360
atcctttcat tcagctttta agaggtgtgc cacatgatta acaatgtct cttagtagtc      3420 tataaacagt tttatgtggg acacgctggg atccctgtcc tagctagatc aaaaggccag      3480 cagggggtg gggggggggg ggggtacata cgtgtagatg tactaattca acgtatgttc      3540
cc                                                                     3542
```

<210> SEQ ID NO 2
<211> LENGTH: 405
<212> TYPE: PRT
<213> ORGANISM: Triticum turgidum
<220> FEATURE:
<223> OTHER INFORMATION: functional Triticum turgidum var. dicoccoides
      WNAC-B1a (DIC) allele predicted protein
<220> FEATURE:
<221> NAME/KEY: DOMAIN
<222> LOCATION: (34)..(55)
<223> OTHER INFORMATION: conserved NAC (NAM/ATAF1/CUC2) domain
<220> FEATURE:
<221> NAME/KEY: DOMAIN
<222> LOCATION: (66)..(80)
<223> OTHER INFORMATION: conserved NAC (NAM/ATAF1/CUC2) domain
<220> FEATURE:
<221> NAME/KEY: DOMAIN
<222> LOCATION: (86)..(124)
<223> OTHER INFORMATION: conserved NAC (NAM/ATAF1/CUC2) domain

```
<220> FEATURE:
<221> NAME/KEY: DOMAIN
<222> LOCATION: (139)..(166)
<223> OTHER INFORMATION: conserved NAC (NAM/ATAF1/CUC2) domain
<220> FEATURE:
<221> NAME/KEY: DOMAIN
<222> LOCATION: (193)..(205)
<223> OTHER INFORMATION: conserved NAC (NAM/ATAF1/CUC2) domain

<400> SEQUENCE: 2
```

| | | | | | | | | | | | | | | |
|---|---|---|---|---|---|---|---|---|---|---|---|---|---|---|
| Met | Gly | Ser | Ser | Asp | Ser | Ser | Gly | Ser | Ala | Gln | Lys | Ala | Thr | Arg |
| 1 | | | | 5 | | | | | 10 | | | | | 15 |
| Tyr | His | His | Gln | His | Gln | Pro | Pro | Pro | Gln | Arg | Gly | Ser | Ala | Pro |
| | | | 20 | | | | | 25 | | | | | 30 | |
| Glu | Leu | Pro | Pro | Gly | Phe | Arg | Phe | His | Pro | Thr | Asp | Glu | Glu | Leu | Val |
| | | 35 | | | | | 40 | | | | | 45 | | | |
| Val | His | Tyr | Leu | Lys | Lys | Lys | Ala | Asp | Lys | Ala | Pro | Leu | Pro | Val | Asn |
| | 50 | | | | | 55 | | | | | 60 | | | | |
| Ile | Ile | Ala | Glu | Val | Asp | Leu | Tyr | Lys | Phe | Asp | Pro | Trp | Glu | Leu | Pro |
| 65 | | | | | 70 | | | | | 75 | | | | | 80 |
| Glu | Lys | Ala | Thr | Ile | Gly | Glu | Gln | Glu | Trp | Tyr | Phe | Phe | Ser | Pro | Arg |
| | | | | 85 | | | | | 90 | | | | | 95 | |
| Asp | Arg | Lys | Tyr | Pro | Asn | Gly | Ala | Arg | Pro | Asn | Arg | Ala | Ala | Thr | Ser |
| | | | 100 | | | | | 105 | | | | | 110 | | |
| Gly | Tyr | Trp | Lys | Ala | Thr | Gly | Thr | Asp | Lys | Pro | Ile | Leu | Ala | Ser | Gly |
| | | 115 | | | | | 120 | | | | | 125 | | | |
| Thr | Gly | Cys | Gly | Leu | Val | Arg | Glu | Lys | Leu | Gly | Val | Lys | Lys | Ala | Leu |
| | 130 | | | | | 135 | | | | | 140 | | | | |
| Val | Phe | Tyr | Arg | Gly | Lys | Pro | Pro | Lys | Gly | Leu | Lys | Thr | Asn | Trp | Ile |
| 145 | | | | | 150 | | | | | 155 | | | | | 160 |
| Met | His | Glu | Tyr | Arg | Leu | Thr | Asp | Ala | Ser | Gly | Ser | Thr | Thr | Ala | Thr |
| | | | | 165 | | | | | 170 | | | | | 175 | |
| Asn | Arg | Pro | Pro | Pro | Val | Thr | Gly | Gly | Ser | Arg | Ala | Ala | Ala | Ser | Leu |
| | | | 180 | | | | | 185 | | | | | 190 | | |
| Arg | Leu | Asp | Asp | Trp | Val | Leu | Cys | Arg | Ile | Tyr | Lys | Lys | Ile | Asn | Lys |
| | | 195 | | | | | 200 | | | | | 205 | | | |
| Ala | Ala | Ala | Gly | Asp | Gln | Gln | Arg | Asn | Thr | Glu | Cys | Glu | Asp | Ser | Val |
| | 210 | | | | | 215 | | | | | 220 | | | | |
| Glu | Asp | Ala | Val | Thr | Ala | Tyr | Pro | Leu | Tyr | Ala | Thr | Ala | Gly | Met | Thr |
| 225 | | | | | 230 | | | | | 235 | | | | | 240 |
| Gly | Ala | Gly | Ala | His | Gly | Ser | Asn | Tyr | Ala | Ser | Pro | Ser | Leu | Leu | His |
| | | | | 245 | | | | | 250 | | | | | 255 | |
| His | Gln | Asp | Ser | His | Phe | Leu | Asp | Gly | Leu | Phe | Thr | Ala | Asp | Asp | Ala |
| | | | 260 | | | | | 265 | | | | | 270 | | |
| Gly | Leu | Ser | Ala | Gly | Ala | Thr | Ser | Leu | Ser | His | Leu | Ala | Ala | Ala | Ala |
| | | 275 | | | | | 280 | | | | | 285 | | | |
| Arg | Ala | Ser | Pro | Ala | Pro | Thr | Lys | Gln | Phe | Leu | Ala | Pro | Ser | Ser | Ser |
| | 290 | | | | | 295 | | | | | 300 | | | | |
| Thr | Pro | Phe | Asn | Trp | Leu | Asp | Ala | Ser | Pro | Val | Gly | Ile | Leu | Pro | Gln |
| 305 | | | | | 310 | | | | | 315 | | | | | 320 |
| Ala | Arg | Asn | Phe | Pro | Gly | Phe | Asn | Arg | Ser | Arg | Asn | Val | Gly | Asn | Met |
| | | | | 325 | | | | | 330 | | | | | 335 | |
| Ser | Leu | Ser | Ser | Thr | Ala | Asp | Met | Ala | Gly | Ala | Val | Asp | Asn | Gly | Gly |
| | | | 340 | | | | | 345 | | | | | 350 | | |
| Gly | Asn | Ala | Val | Asn | Ala | Met | Ser | Thr | Tyr | Leu | Pro | Val | Gln | Asp | Gly |
| | | 355 | | | | | 360 | | | | | 365 | | | |

```
Thr Tyr His Gln Gln His Val Ile Leu Gly Ala Pro Leu Val Pro Glu
    370                 375                 380

Ala Ala Ala Ala Thr Ser Gly Phe Gln His Pro Val Gln Ile Ser Gly
385                 390                 395                 400

Val Asn Trp Asn Pro
                405

<210> SEQ ID NO 3
<211> LENGTH: 2517
<212> TYPE: DNA
<213> ORGANISM: Triticum turgidum
<220> FEATURE:
<223> OTHER INFORMATION: non-functional Triticum turgidum var. durum
      WNAC-B1b tetraploid cultivar Langdon (LDN) allele
      frame-shift mutation genomic DNA
<220> FEATURE:
<221> NAME/KEY: 5'UTR
<222> LOCATION: (1)..(922)
<220> FEATURE:
<221> NAME/KEY: variation
<222> LOCATION: (657)
<223> OTHER INFORMATION: polymorphic base between LDN and DIC alleles
<220> FEATURE:
<221> NAME/KEY: CDS
<222> LOCATION: join(923..1164, 1380..1717, 1827..2230)
<223> OTHER INFORMATION: non-functional Triticum turgidum var. durum
      WNAC-B1b tetraploid cultivar Langdon (LDN) allele
      frame-shift mutation predicted protein assuming
      conserved exon structure
<220> FEATURE:
<221> NAME/KEY: mutation
<222> LOCATION: (933)
<223> OTHER INFORMATION: 1-bp t insertion frame-shift mutation
<220> FEATURE:
<221> NAME/KEY: exon
<222> LOCATION: (923)..(1164)
<220> FEATURE:
<221> NAME/KEY: variation
<222> LOCATION: (1224)
<223> OTHER INFORMATION: polymorphic base between LDN and DIC alleles
<220> FEATURE:
<221> NAME/KEY: intron
<222> LOCATION: (1165)..(1379)
<220> FEATURE:
<221> NAME/KEY: exon
<222> LOCATION: (1380)..(1717)
<220> FEATURE:
<221> NAME/KEY: intron
<222> LOCATION: (1718)..(1826)
<220> FEATURE:
<221> NAME/KEY: exon
<222> LOCATION: (1827)..(2230)
<220> FEATURE:
<221> NAME/KEY: 3'UTR
<222> LOCATION: (2231)..(2517)

<400> SEQUENCE: 3
ttgcctcttc atgggccggc ccagcgcggg gcgctgcagg cgtcaggagc gccaacgggc        60
gcctgcagcg ccgtatagga gctccctaca tgtccttcta accatccaat cacagattgg       120
tttgcttttt ttgacgaact gatttgtttt taattgtttg aattgcttac cacatgtttc       180
acgtggtctg acgaactggt tgggttcata aggtgtgtga aatgaggtca cgatgttaaa       240
agaggtaccc tttgattagt tgcttcccga gaaacatctg tgctaaaaaa gagagcaaga       300
agaggtcacg atgttggtat catgcggccc accagaatat gctgaaatgg agctcagcac       360
gggccaacaa ataccctagc ccaggaagct acgaagccgg tgcaaactac caggccttaa       420
gccgaaggat ggggcaaggt gaaccgtgtc cggtccggct cccccgcgtc cgcccgcata       480
gaaggaagtg gcggaatact cttcccatcc cagaagaaaa aataaggtag gaagcggaat       540
```

```
gggtggccgt ggtcgcgcga gcttgcgccg tccggtggcg atctgacacg cggtacgagc    600
ggcggccggc atacgtgtcc agcggcgacg ggcccgcggc cccgggctag gtacaaaggt    660
gccgtatttc tcccctgctc tcctcgccac ggtttcacag ccgccccgaa accaccagag    720
ctcccacagc agatcactcg cccgcctctc tctccttcc tcccaaccgt cgctgtaaca     780
aatcccactc cgttccttcc ttcacactac ctagaagctt tggcagttga gttaggtgcc    840
caccacaggg gtgctctggt gggatcatct ggtgtgtttg ttggtagcta gctagctagg    900
ggaagaagat ctgatgaggt ccatgggcag cttccgactc atcttccggc tcggcgcaaa    960
aagcaacgcg gtatcaccat cagcatcagc cgccgcctcc gcagcggggc tcggcgccgg   1020
agctcccgcc gggcttccgg ttccacccga cggacgagga gctggtggtg cactacctca   1080
agaagaaggc cgacaaggcg ccgctccccg tcaacatcat cgccgaggtg gatctctaca   1140
agttcgaccc atgggagctc cccggtatgt tatgtctatc tcgtcggccg gccgtgctta   1200
ctttatcaag cgccgcaaat tttaggtgca attaaataat cgaataatcc atccatctca   1260
tgcttatact cctgtgcaca agtagtattt ttatattctt ccagtacaca tgtgtgtaga   1320
tggtttatgt atgtgatcct gtcgtgcttg ttcatgcgct cgggatccgg atccatcaga   1380
gaaggcgacc atcggggagc aggagtggta cttcttcagc ccgcgcgacc gcaagtaccc   1440
caacggcgcg cggccgaacc gggcggcgac gtcgggggtac tggaaggcca ccggcacgga   1500
caagcctatc ctggcctcgg gacggggtg cggcctggtc cgggagaagc tcggcgtcaa    1560
gaaggcgctc gtgttctacc gcgggaagcc gcccaagggc ctcaaaacca actggatcat   1620
gcacgagtac cgcctcaccg acgcatctgg ctccaccacc gccaccaacc gaccgccgcc   1680
ggtgaccggc gggagcaggg ctgctgcctc tctcagggta cgtacacgtg tcgatcgcac   1740
ggtctagcag tatttaattg ctctccagct taattagggt attgttgatg gttgatgaag   1800
ttaattatgt accgtcgtct catcagttgg acgactgggt gctgtgccgc atctacaaga   1860
agatcaacaa ggccgcggcc ggcgatcagc agaggaacac ggagtgcgag gactccgtgg   1920
aggacgcggt caccgcgtac ccgctctatg ccacggcggg catgaccggt gcaggtgcgc   1980
atggcagcaa ctacgcttca ccttcactgc tccatcatca ggacagccat ttcctggacg   2040
gcctgttcac agcagacgac gccggcctct cggcgggcgc cacctcgctg agccacctag   2100
cagcggcggc gagggcaagc ccggctccga ccaaacagtt tctcgccccg tcgtcttcga   2160
ccccgttcaa ctggctcgat gcgtcaccag tcggcatcct cccacaggca aggaattttc   2220
ctgggtttaa caggagcaga aacgtcggca atatgtcgct gtcatcgacg gccgacatgg   2280
ctggcgcagt ggacaacggt ggaggcaatg cggtgaacgc catgtctacc tatcttcccg   2340
tgcaagacgg gacgtaccat cagcagcatg tcatcctcgg cgctccgctg gtgccagaag   2400
ccgccgccgc cacctctgga ttccagcatc ccgttcaaat atccggcgtg aactggaatc   2460
cctgatcaaa tgatatgaac accacatacg ggcatgcacg cacgcatgca taactttt    2517
```

<210> SEQ ID NO 4
<211> LENGTH: 327
<212> TYPE: PRT
<213> ORGANISM: Triticum turgidum
<220> FEATURE:
<223> OTHER INFORMATION: non-functional Triticum turgidum var. durum
      WNAC-B1b tetraploid cultivar Langdon (LDN) allele
      frame-shift mutation predicted protein assuming
      conserved exon structure

<400> SEQUENCE: 4

```
Met Gly Ser Phe Arg Leu Ile Phe Arg Leu Gly Ala Lys Ser Asn Ala
1               5                   10                  15

Val Ser Pro Ser Ala Ala Ala Ser Ala Ala Gly Leu Gly Ala
            20                  25                  30

Gly Ala Pro Ala Gly Leu Pro Val Pro Pro Asp Gly Arg Gly Ala Gly
        35                  40                  45

Gly Ala Leu Pro Gln Glu Glu Gly Arg Gln Gly Ala Ala Pro Arg Gln
    50                  55                  60

His His Arg Arg Gly Gly Ser Leu Gln Val Arg Pro Met Gly Ala Pro
65                  70                  75                  80

Arg Glu Gly Asp His Arg Gly Ala Gly Val Val Leu Leu Gln Pro Ala
                85                  90                  95

Arg Pro Gln Val Pro Gln Arg Arg Ala Ala Glu Pro Gly Gly Asp Val
                100                 105                 110

Gly Val Leu Glu Gly His Arg His Gly Gln Ala Tyr Pro Gly Leu Gly
            115                 120                 125

Asp Gly Val Arg Pro Gly Pro Gly Glu Ala Arg Arg Gln Glu Gly Ala
    130                 135                 140

Arg Val Leu Pro Arg Glu Ala Ala Gln Gly Pro Gln Asn Gln Leu Asp
145                 150                 155                 160

His Ala Arg Val Pro Pro His Arg Arg Ile Trp Leu His His Arg His
                165                 170                 175

Gln Pro Thr Ala Ala Gly Asp Arg Arg Glu Gln Gly Cys Cys Leu Ser
            180                 185                 190

Gln Val Gly Arg Leu Gly Ala Val Pro His Leu Gln Glu Asp Gln Gln
            195                 200                 205

Gly Arg Gly Arg Arg Ser Ala Glu Glu His Gly Val Arg Gly Leu Arg
        210                 215                 220

Gly Gly Arg Gly His Arg Val Pro Ala Leu Cys His Gly Gly His Asp
225                 230                 235                 240

Arg Cys Arg Cys Ala Trp Gln Gln Leu Arg Phe Thr Phe Thr Ala Pro
                245                 250                 255

Ser Ser Gly Gln Pro Phe Pro Gly Arg Pro Val His Ser Arg Arg Arg
            260                 265                 270

Arg Pro Leu Gly Gly Arg His Leu Ala Glu Pro Ser Ser Gly Gly
            275                 280                 285

Glu Gly Lys Pro Gly Ser Asp Gln Thr Val Ser Arg Pro Val Val Phe
    290                 295                 300

Asp Pro Val Gln Leu Ala Arg Cys Val Thr Ser Arg His Pro Pro Thr
305                 310                 315                 320

Gly Lys Glu Phe Ser Trp Val
                325

<210> SEQ ID NO 5
<211> LENGTH: 3162
<212> TYPE: DNA
<213> ORGANISM: Triticum turgidum
<220> FEATURE:
<223> OTHER INFORMATION: Triticum turgidum var. durum variety Langdon A
      genome WNAC-A1 genomic DNA
<220> FEATURE:
<221> NAME/KEY: 5'UTR
<222> LOCATION: (1)..(614)
<220> FEATURE:
<221> NAME/KEY: CDS
<222> LOCATION: join(615..852, 1072..1409, 1522..2163)
<223> OTHER INFORMATION: Triticum turgidum var. durum variety Langdon A
``` genome WNAC-A1 predicted protein
<220> FEATURE:
<221> NAME/KEY: exon
<222> LOCATION: (615)..(852)
<220> FEATURE:
<221> NAME/KEY: intron
<222> LOCATION: (853)..(1071)
<220> FEATURE:
<221> NAME/KEY: exon
<222> LOCATION: (1072)..(1409)
<220> FEATURE:
<221> NAME/KEY: intron
<222> LOCATION: (1410)..(1521)
<220> FEATURE:
<221> NAME/KEY: exon
<222> LOCATION: (1522)..(2163)
<220> FEATURE:
<221> NAME/KEY: 3'UTR
<222> LOCATION: (2164)..(3162)

<400> SEQUENCE: 5

```
acgatgttag gtatcatgcg gcccaccaga atatgctgaa atggagctca gcacgggccg      60
ataaaacacc caggaagcta cgaagccggt gcaaactagg ccttgggccg aaggacgggg     120
caaggtgagc cgtggtccgg tccggctccc ccgcgccatc ccagaagaga aaaaagtga     180
ggaagcggaa tgggtggagg tggtcgcgcg agctcgcgcc gtccggtggc gatctgacac     240
gcggtacgag cggcggccgg catacgtgtc cagcggcgac gggcccgcgg ccccgggcaa     300
ggttacaacg gagccgtatt tactcctccc ctgctctcct cgccacggtt tcacagccgc     360
cccgaaacca ccagagcttc caccgcagat cactcgcccg cctcccctct cctctcctcc     420
caaccgtcgc ggtaacaaat cccactccgt tccttccttc atcacactac ctagaagctt     480
tggcagttga gttaggtgcc caccacagaa tcgaattccc gcggccgcca tggcggggcg     540
ctccggtggg atcatctggt gtgtttgttg gtagctagct tgctagggg aacgaagaag      600
atccgatgag gtccatgggc agctccgact catcctccgg ctcggcgcaa aaagcagcgc     660
ggcatcagca tgagccgccg cctccgcggc agcggggctc ggcgccggag ctcccaccgg     720
gcttccggtt ccacccgacg gacgaggagc tggtcgtgca ctacctcaag aagaaggccg     780
ccaaggtgcc gctccccgtc accatcatcg ccgaggtgga tctctacaag ttcgacccat     840
gggagctccc cggtatgcta tgtctatctc gtcggccgtg cttgatttat cacgcgccgc     900
aaatttccgg tgcaattaaa taatcgaata atccatccat ctcatgctta tactattgct     960
gtgcacaagt attttatat tcttctagca cacatgtgtg tagatatctg ggttatgtat     1020
gtgatcctgt cgtgcttgtt catgcgctcg ggatcggat ccatccatca gagaaggcga     1080
ccttcgggga gcaggagtgg tacttcttca gcccgcgcga ccgcaagtac cccaacggcg     1140
cgcggccgaa ccgggcggcg acgtcgggct actggaaggc caccggcacg gacaaaccta     1200
tcctggcctc ggggacgggg tgcggcctgg tccgggagaa gctcggcgtc aagaaggcgc     1260
tcgtcttcta ccgcgggaag ccgcccaagg gcctcaaaac caactggatc atgcacgagt     1320
accgcctcac cgacgtgtct ggctccacca ccaccagccg gccgccgccg cctgtgaccg     1380
gcgggagccg ggctgcagcc tctctgaggg tacgtacacg tgtcgatcgc acggtatagc     1440
tagcagtatt taattactct cgagcttaat tagggtattg ttgatggttg atgaagttaa     1500
ttatgtacgt cgtctcatca gttggacgac tgggtgctgt gccgcatcta caagaagatc     1560
aacaaggccg cggccggaga tcagcagagg agcacggagt gcgaggactc cgtggaggac     1620
gcggtcaccg cgtacccgct ctatgccacg cgggcatgg ccggtgcagg tgcgcatggc     1680
agcaactacg cttcaccttc actgctccat catcaggaca gccatttcct ggagggcctg     1740
```

```
ttcacagcag acgacgccgg cctctcggcg ggcgccacct cgctgagcca cctggccgcg    1800
gcggcgaggg cgagcccggc tccgaccaaa cagtttctcg ccccgtcgtc ttcaaccccg    1860
ttcaactggc tcgatgcgtc acccgccggc atcctgccac aggcaaggaa tttccctggg    1920
tttaacagga gcagaaacgt cggcaatatg tcgctgtcat cgacggccga catggctggc    1980
gcggccggca atgcggtgaa cgccatgtcc gcatttatga atcctctccc cgtgcaagac    2040
gggacgtacc atcaacacca tgtcatcctc ggcgcccac tggcgccaga ggctaccaca     2100
ggcggcgcca cctctggttt ccagcatccc gtccaagtat ccggcgtgaa ctggaatccc    2160
tgagcaaatg atatgaacac cacatacgcg catgcacgca tgcataactt ttgcaagtgt    2220
agccagtagt tgttgcagtt cgtggtagtc gctttcagtg agcactgagt agctagctgc    2280
atgcacatca ccattgcatg gatatatatg gctgcattgc accatggcca cgtacttgtc    2340
cgaacttgct agcccatata gtagcacata gctagggagt atttttcgaag taaaaaagat    2400 cataacatag tgctccatat atattgtagt aaatatatat tttagatata tgagtatgat    2460
attagcgtca tatgcatata gtatatattg tagtgcatat agcaaataca tatgcagttg    2520
attacaaacc ccagtcagat ataattttg gccgggtcta gctacgcatc atgtataaat      2580
aggtgtgtat gtaaataagc aacgcatggt aattgcatac acgggtatga ttcatctaca    2640
tggacctaca tcgtataact ttttttgcg aatgaagttt tgtgagctac tatgttgcag      2700
tggtttagtt attagttatg tgagtggccc ttatgcgcca atcttttata catagattgg    2760
aatttatatg ctaaatatgt ttgacaattg tgtgttatct ccttaattcc acttttcaaa    2820
ggaaaacttc tttccttgga atggaaggca ggcttggcga tacagatgtt cagatctcct    2880
accattataa ccgactctat gtaagcctaa ccctctccgg tgtctatata aaccggaggg    2940
ttttagtcag taggacaaca tacacatcaa caatcatacc ataggctagc ttctagggtt    3000
tagcctctct gatctcgtgg tagatctact cttgtactac ccatatcatc aatattaatc    3060
aagcaggacg tagggtttta cctccatcga gagggcccaa acctgggtaa aacttcatgt    3120
ccattgtctc ctgttaccat ccggcctaga cgtatagttc gg                       3162

<210> SEQ ID NO 6
<211> LENGTH: 405
<212> TYPE: PRT
<213> ORGANISM: Triticum turgidum
<220> FEATURE:
<223> OTHER INFORMATION: Triticum turgidum var. durum variety Langdon A
      genome WNAC-A1 predicted protein
<220> FEATURE:
<221> NAME/KEY: DOMAIN
<222> LOCATION: (34)..(55)
<223> OTHER INFORMATION: conserved NAC (NAM/ATAF1/CUC2) domain
<220> FEATURE:
<221> NAME/KEY: DOMAIN
<222> LOCATION: (66)..(80)
<223> OTHER INFORMATION: conserved NAC (NAM/ATAF1/CUC2) domain
<220> FEATURE:
<221> NAME/KEY: DOMAIN
<222> LOCATION: (86)..(124)
<223> OTHER INFORMATION: conserved NAC (NAM/ATAF1/CUC2) domain
<220> FEATURE:
<221> NAME/KEY: DOMAIN
<222> LOCATION: (139)..(166)
<223> OTHER INFORMATION: conserved NAC (NAM/ATAF1/CUC2) domain
<220> FEATURE:
<221> NAME/KEY: DOMAIN
<222> LOCATION: (193)..(205)
<223> OTHER INFORMATION: conserved NAC (NAM/ATAF1/CUC2) domain

<400> SEQUENCE: 6
```

```
Met Gly Ser Ser Asp Ser Ser Gly Ser Ala Gln Lys Ala Ala Arg
  1               5                  10                  15

His Gln His Glu Pro Pro Pro Arg Gln Arg Gly Ser Ala Pro Glu
             20                  25                  30

Leu Pro Pro Gly Phe Arg Phe His Pro Thr Asp Glu Glu Leu Val Val
         35                  40                  45

His Tyr Leu Lys Lys Ala Ala Lys Val Pro Leu Pro Val Thr Ile
 50                  55                  60

Ile Ala Glu Val Asp Leu Tyr Lys Phe Asp Pro Trp Glu Leu Pro Glu
 65                  70                  75                  80

Lys Ala Thr Phe Gly Glu Gln Glu Trp Tyr Phe Phe Ser Pro Arg Asp
                 85                  90                  95

Arg Lys Tyr Pro Asn Gly Ala Arg Pro Asn Arg Ala Ala Thr Ser Gly
             100                 105                 110

Tyr Trp Lys Ala Thr Gly Thr Asp Lys Pro Ile Leu Ala Ser Gly Thr
         115                 120                 125

Gly Cys Gly Leu Val Arg Glu Lys Leu Gly Val Lys Lys Ala Leu Val
130                 135                 140

Phe Tyr Arg Gly Lys Pro Lys Gly Leu Lys Thr Asn Trp Ile Met
145                 150                 155                 160

His Glu Tyr Arg Leu Thr Asp Val Ser Gly Ser Thr Thr Thr Ser Arg
                 165                 170                 175

Pro Pro Pro Pro Val Thr Gly Gly Ser Arg Ala Ala Ser Leu Arg
             180                 185                 190

Leu Asp Asp Trp Val Leu Cys Arg Ile Tyr Lys Lys Ile Asn Lys Ala
         195                 200                 205

Ala Ala Gly Asp Gln Gln Arg Ser Thr Glu Cys Glu Asp Ser Val Glu
         210                 215                 220

Asp Ala Val Thr Ala Tyr Pro Leu Tyr Ala Thr Ala Gly Met Ala Gly
225                 230                 235                 240

Ala Gly Ala His Gly Ser Asn Tyr Ala Ser Pro Ser Leu Leu His His
                 245                 250                 255

Gln Asp Ser His Phe Leu Glu Gly Leu Phe Thr Ala Asp Asp Ala Gly
             260                 265                 270

Leu Ser Ala Gly Ala Thr Ser Leu Ser His Leu Ala Ala Ala Arg
         275                 280                 285

Ala Ser Pro Ala Pro Thr Lys Gln Phe Leu Ala Pro Ser Ser Ser Thr
         290                 295                 300

Pro Phe Asn Trp Leu Asp Ala Ser Pro Ala Gly Ile Leu Pro Gln Ala
305                 310                 315                 320

Arg Asn Phe Pro Gly Phe Asn Arg Ser Arg Asn Val Gly Asn Met Ser
                 325                 330                 335

Leu Ser Ser Thr Ala Asp Met Ala Gly Ala Ala Gly Asn Ala Val Asn
             340                 345                 350

Ala Met Ser Ala Phe Met Asn Pro Leu Pro Val Gln Asp Gly Thr Tyr
             355                 360                 365

His Gln His His Val Ile Leu Gly Ala Pro Leu Ala Pro Glu Ala Thr
         370                 375                 380

Thr Gly Gly Ala Thr Ser Gly Phe Gln His Pro Val Gln Val Ser Gly
385                 390                 395                 400

Val Asn Trp Asn Pro
                405
```

<210> SEQ ID NO 7
<211> LENGTH: 1712
<212> TYPE: DNA
<213> ORGANISM: Triticum tauschii
<220> FEATURE:
<223> OTHER INFORMATION: Triticum tauschii D genome WNAC-D1 genomic DNA
<220> FEATURE:
<221> NAME/KEY: 5'UTR
<222> LOCATION: (1)..(104)
<220> FEATURE:
<221> NAME/KEY: CDS
<222> LOCATION: join(105..342, 551..894, 1010..1654)
<223> OTHER INFORMATION: Triticum tauschii D genome WNAC-D1 predicted
    protein
<220> FEATURE:
<221> NAME/KEY: exon
<222> LOCATION: (105)..(342)
<220> FEATURE:
<221> NAME/KEY: intron
<222> LOCATION: (343)..(550)
<220> FEATURE:
<221> NAME/KEY: exon
<222> LOCATION: (551)..(894)
<220> FEATURE:
<221> NAME/KEY: intron
<222> LOCATION: (895)..(1109)
<220> FEATURE:
<221> NAME/KEY: exon
<222> LOCATION: (1010)..(1654)
<220> FEATURE:
<221> NAME/KEY: 3'UTR
<222> LOCATION: (1655)..(1712)

<400> SEQUENCE: 7

| | | | | | |
|---|---|---|---|---|---|
| ggcagtgagt | taggtgccca | ccacaggggc | gctcgatctg | gtgggatcat | ccggtgtgtt | 60 |
| tgttggtagc | tagctagcta | agggaagagg | atccgatgag | gtccatgggc | agctcggact | 120 |
| catcttccgg | ctcggcgcaa | aaagcagcgc | ggcatcagca | tgagccgccg | cctccgcggc | 180 |
| agcggggctc | ggcgccggag | ctcccgccgg | gcttccggtt | ccaccgacg | gacgaggagc | 240 |
| tggtcgtgca | ctacctcaag | aagaaggccg | ccaaggtgcc | gctccccgtc | accatcatcg | 300 |
| ccgaggtgga | tctctacaag | ttcgacccat | gggagctccc | cggtatgtta | tgtctatctc | 360 |
| gtcggtcgtg | cttagtttat | caagcgccgc | aaaattccgg | cgcaattaaa | taatcgaata | 420 |
| atccatccat | ctcatgctta | tactcctgtg | cacaagtatt | tttatattct | tgtagtacac | 480 |
| atgtgtgtag | atggtttatg | tatgtgatcc | tgtcgtgctt | gttcatgcgc | tcgggatcgg | 540 |
| gatccatcag | agaaggcgac | cttcggggag | caggagtggt | acttcttcag | cccgcgcgac | 600 |
| cgcaagtacc | ccaacggcgc | gcggcccaac | cgggcggcga | cgtcggggta | ctggaaggcc | 660 |
| accggcacgg | acaaacctat | cctggcctcc | gggacggggt | gcggcctggt | ccggagaag | 720 |
| ctcggcgtca | agaaggcgct | cgtgttctac | gcgggaagc | cgcccaaggg | cctcaaaacc | 780 |
| aactggatca | tgcatgaata | ccgcctcacc | gacgcgtctg | gctccaccac | caccagccga | 840 |
| ccgccgccgc | cgccgcctgt | gaccggcggg | agcagggctg | ctgcctctct | gagggtacgt | 900 |
| acacgtgtcg | atcgcacggt | ctagctagca | gtatttaatt | gctctccagc | ttaattaggg | 960 |
| tattgttgat | ggttgatgaa | gttaattatg | tacgtcgtcg | tctcatcagt | tggatgactg | 1020 |
| ggtgctgtgc | cgcatctaca | agaagatcaa | caaggccgcg | gccggagatc | agcagaggag | 1080 |
| catggagtgc | gaggactccg | tggaggacgc | ggtcactgcg | tacccgctct | atgccacggc | 1140 |
| gggcatggcc | ggtgcaggtg | cgcatggcag | caactacgct | tcatcttcac | tgctccatca | 1200 |
| tcaggacagc | catttcctgg | acggcctgtt | cacagcagac | gacgccggcc | tctcggcggg | 1260 |
| cgccacctcg | ctgagccacc | tggccccggc | ggcgagggcg | agcccggctc | cgaccaaaca | 1320 |

```
gtttctcgcc ccgtcgtctt caaccccgtt caactggctc gaggcgtcag ccgctggcat    1380
cctgccacag gcaaggaatt tccctgggtt taacaggagc agaaacgtcg gcaatatgtc    1440
gctgtcatcg acggccgaca tggctggcgc ggccggcaat gcggtgaacg ccatgtctgc    1500
atttatgaat cctcttcccg tgcaagacgg gacgtaccat caacaccatg tcatcctcgg    1560
cgccccactg gcgccagagg ccaccgcagg cgccgccacc tctggtttcc agcatcatgc    1620
cgtccaaata tccggcgtga actggaatcc ctgagcaaat gatatgaaca ccacatacgc    1680
gcatgcacgc tcgcatgcat aactttgcaa ga                                  1712
```

<210> SEQ ID NO 8
<211> LENGTH: 408
<212> TYPE: PRT
<213> ORGANISM: Triticum tauschii
<220> FEATURE:
<223> OTHER INFORMATION: Triticum tauschii D genome WNAC-D1 predicted
      protein
<220> FEATURE:
<221> NAME/KEY: DOMAIN
<222> LOCATION: (33)..(54)
<223> OTHER INFORMATION: conserved NAC (NAM/ATAF1/CUC2) domain
<220> FEATURE:
<221> NAME/KEY: DOMAIN
<222> LOCATION: (65)..(79)
<223> OTHER INFORMATION: conserved NAC (NAM/ATAF1/CUC2) domain
<220> FEATURE:
<221> NAME/KEY: DOMAIN
<222> LOCATION: (85)..(123)
<223> OTHER INFORMATION: conserved NAC (NAM/ATAF1/CUC2) domain
<220> FEATURE:
<221> NAME/KEY: DOMAIN
<222> LOCATION: (138)..(165)
<223> OTHER INFORMATION: conserved NAC (NAM/ATAF1/CUC2) domain
<220> FEATURE:
<221> NAME/KEY: DOMAIN
<222> LOCATION: (194)..(206)
<223> OTHER INFORMATION: conserved NAC (NAM/ATAF1/CUC2) domain

<400> SEQUENCE: 8

```
Met Gly Ser Ser Asp Ser Ser Gly Ser Ala Gln Lys Ala Ala Arg
  1               5                  10                  15

His Gln His Glu Pro Pro Pro Arg Gln Arg Gly Ser Ala Pro Glu
                 20                  25                  30

Leu Pro Pro Gly Phe Arg Phe His Pro Thr Asp Glu Glu Leu Val
                 35                  40                  45

His Tyr Leu Lys Lys Lys Ala Ala Lys Val Pro Leu Pro Val Thr Ile
 50                  55                  60

Ile Ala Glu Val Asp Leu Tyr Lys Phe Asp Pro Trp Glu Leu Pro Glu
 65                  70                  75                  80

Lys Ala Thr Phe Gly Glu Gln Glu Trp Tyr Phe Phe Ser Pro Arg Asp
                 85                  90                  95

Arg Lys Tyr Pro Asn Gly Ala Arg Pro Asn Arg Ala Ala Thr Ser Gly
                100                 105                 110

Tyr Trp Lys Ala Thr Gly Thr Asp Lys Pro Ile Leu Ala Ser Gly Thr
                115                 120                 125

Gly Cys Gly Leu Val Arg Glu Lys Leu Gly Val Lys Lys Ala Leu Val
                130                 135                 140

Phe Tyr Arg Gly Lys Pro Pro Lys Gly Leu Lys Thr Asn Trp Ile Met
145                 150                 155                 160

His Glu Tyr Arg Leu Thr Asp Ala Ser Gly Ser Thr Thr Thr Ser Arg
                165                 170                 175
```

```
Pro Pro Pro Pro Pro Val Thr Gly Gly Ser Arg Ala Ala Ala Ser
            180                 185                 190

Leu Arg Leu Asp Asp Trp Val Leu Cys Arg Ile Tyr Lys Lys Ile Asn
        195                 200                 205

Lys Ala Ala Ala Gly Asp Gln Gln Arg Ser Met Glu Cys Glu Asp Ser
    210                 215                 220

Val Glu Asp Ala Val Thr Ala Tyr Pro Leu Tyr Ala Thr Ala Gly Met
225                 230                 235                 240

Ala Gly Ala Gly Ala His Gly Ser Asn Tyr Ala Ser Ser Ser Leu Leu
                245                 250                 255

His His Gln Asp Ser His Phe Leu Asp Gly Leu Phe Thr Ala Asp Asp
            260                 265                 270

Ala Gly Leu Ser Ala Gly Ala Thr Ser Leu Ser His Leu Ala Pro Ala
            275                 280                 285

Ala Arg Ala Ser Pro Ala Pro Thr Lys Gln Phe Leu Ala Pro Ser Ser
    290                 295                 300

Ser Thr Pro Phe Asn Trp Leu Glu Ala Ser Ala Ala Gly Ile Leu Pro
305                 310                 315                 320

Gln Ala Arg Asn Phe Pro Gly Phe Asn Arg Ser Arg Asn Val Gly Asn
                325                 330                 335

Met Ser Leu Ser Ser Thr Ala Asp Met Ala Gly Ala Ala Gly Asn Ala
                340                 345                 350

Val Asn Ala Met Ser Ala Phe Met Asn Pro Leu Pro Val Gln Asp Gly
                355                 360                 365

Thr Tyr His Gln His His Val Ile Leu Gly Ala Pro Leu Ala Pro Glu
            370                 375                 380

Ala Thr Ala Gly Ala Ala Thr Ser Gly Phe Gln His His Ala Val Gln
385                 390                 395                 400

Ile Ser Gly Val Asn Trp Asn Pro
                405

<210> SEQ ID NO 9
<211> LENGTH: 1558
<212> TYPE: DNA
<213> ORGANISM: Triticum turgidum
<220> FEATURE:
<223> OTHER INFORMATION: Triticum turgidum var. durum WNAC-B2 allele
      genomic DNA
<220> FEATURE:
<221> NAME/KEY: 5'UTR
<222> LOCATION: (1)..(23)
<220> FEATURE:
<221> NAME/KEY: CDS
<222> LOCATION: join(24..246, 437..756, 874..1521)
<223> OTHER INFORMATION: Triticum turgidum var. durum WNAC-B2 allele
      predicted protein
<220> FEATURE:
<221> NAME/KEY: exon
<222> LOCATION: (24)..(246)
<220> FEATURE:
<221> NAME/KEY: intron
<222> LOCATION: (247)..(436)
<220> FEATURE:
<221> NAME/KEY: exon
<222> LOCATION: (437)..(756)
<220> FEATURE:
<221> NAME/KEY: intron
<222> LOCATION: (757)..(873)
<220> FEATURE:
<221> NAME/KEY: exon
<222> LOCATION: (874)..(1521)
<220> FEATURE:
<221> NAME/KEY: 3'UTR
<222> LOCATION: (1522)..(1558)
```

<400> SEQUENCE: 9

```
gctgtgcagg tctgatgaga tccatgggca gctcggactc atcttcaggc tcggcaccac      60
cgcggcatca gccgccgcct ccgcagcagg gctcggcccc ggagctcccg ccgggcttcc     120
ggttccaccc gacggacgag gagctggtcg tgcactacct caagaagaag gccgccaagg     180
tgccgctccc cgtcaccatc atcaccgagt ggatctctac aagttcgac ccatgggagc      240
tgcccggtat gtgtatctca cctcgtcgtg cttatcaagc gccgtaattt tccagtgcaa     300
ttaaataatc gaacccatcc atcatgctta taccgtgcaa gaagtatttt tatattcttt     360
cagtacacat gtatgtagat ggtttatgta tgtgatcctg tcgtgcttgt tcatgcgctc     420
gctcgggatc gatcagagaa ggcgaccttc ggtgagcagg agtggtactt cttcagcccg     480
cgcgaccgca agtaccccaa cggcgcgcgg cccaacaggg cggctacgtc ggggtactgg     540
aaggccaccg gcacggacaa acctatcctg gcctccgggt gcggccggga gaaggtcggc     600
gtcaagaagg cgctcgtgtt ctaccgcggg aagccgccca agggcctcaa aaccaactgg     660
atcatgcacg agtaccgcct caccgacgcg tctagctccg ccaccaccag ccgaccgccg     720
cctgtcaccg gcgggagcag gtctgcctct ctcagggtac gtgtcgatcg atcgcgcggt     780
ctagcatagc agtaaccaat cgtgtttaat tactctcgag cttagggtat tgtggttgat     840
gaatttaatt agtgtacgtc gtcgtctcat cagttggacg actgggtgct gtgccgcata     900
tacaagaaga tcaacaaggc cgccgccggg gatcagcaga ggagcatgga gtgcgaggac     960
tccgtggagg acgccgtcac cgcatacccg ctttatgcca cggcgggcat gaccggtgca    1020
ggggcgcatg cagcaacta cgattcactg ctccatcacc aggacagcca cgaggacaac    1080
ttcctggacg gcctgctcac agcagaggac gccggcctct cggcgggccc cacctcgctg    1140
agccacctag ccgcggcggc gagggcgagc ccggctccga ccaaacagtt tctggccccg    1200
tcgtcttcaa ccccgttcaa ctggctcgat gcgtcaaccg ttggcatcct cccacaggca    1260
aggaatttcc ctgggtttaa caggagcaga aatgtcggca acatgtcgct gtcgtcgacg    1320
gccgacatgg cggtggacaa cggcgggggc aatgcgataa acaccatgcc tccattcatg    1380
aatcatcttc ccatgcaaga cgggacctac catcaacagc atgtcatcct cggcgccccg    1440
ctcgcgccag aagccactgc cgccgccacc tctgccttcc agcacccccgt ccaaatatcc    1500
ggcgtgaact ggaatccctg aacaaatgat atgaacacca catatgcgca tgcacgca     1558
```

<210> SEQ ID NO 10
<211> LENGTH: 396
<212> TYPE: PRT
<213> ORGANISM: Triticum turgidum
<220> FEATURE:
<223> OTHER INFORMATION: Triticum turgidum var. durum WNAC-B2 allele predicted protein
<220> FEATURE:
<221> NAME/KEY: DOMAIN
<222> LOCATION: (28)..(49)
<223> OTHER INFORMATION: conserved NAC (NAM/ATAF1/CUC2) domain
<220> FEATURE:
<221> NAME/KEY: DOMAIN
<222> LOCATION: (60)..(74)
<223> OTHER INFORMATION: conserved NAC (NAM/ATAF1/CUC2) domain
<220> FEATURE:
<221> NAME/KEY: DOMAIN
<222> LOCATION: (80)..(118)
<223> OTHER INFORMATION: conserved NAC (NAM/ATAF1/CUC2) domain
<220> FEATURE:
<221> NAME/KEY: DOMAIN
<222> LOCATION: (129)..(156)
<223> OTHER INFORMATION: conserved NAC (NAM/ATAF1/CUC2) domain -continued

```
<220> FEATURE:
<221> NAME/KEY: DOMAIN
<222> LOCATION: (181)..(193)
<223> OTHER INFORMATION: conserved NAC (NAM/ATAF1/CUC2) domain

<400> SEQUENCE: 10
```

| | | | | | | | | | | | | | | |
|---|---|---|---|---|---|---|---|---|---|---|---|---|---|---|
| Met | Gly | Ser | Ser | Asp | Ser | Ser | Gly | Ser | Ala | Pro | Pro | Arg | His | Gln |
| 1 | | | | 5 | | | | | 10 | | | | | 15 |
| Pro | Pro | Pro | Gln | Gln | Gly | Ser | Ala | Pro | Glu | Leu | Pro | Pro | Gly | Phe |
| | | 20 | | | | | 25 | | | | | 30 | | |
| Arg | Phe | His | Pro | Thr | Asp | Glu | Glu | Leu | Val | Val | His | Tyr | Leu | Lys | Lys |
| | | 35 | | | | 40 | | | | | 45 | | | | |
| Lys | Ala | Ala | Lys | Val | Pro | Leu | Pro | Val | Thr | Ile | Ile | Thr | Glu | Val | Asp |
| 50 | | | | | 55 | | | | | 60 | | | | | |
| Leu | Tyr | Lys | Phe | Asp | Pro | Trp | Glu | Leu | Pro | Lys | Ala | Thr | Phe | Gly |
| 65 | | | | | 70 | | | | | 75 | | | | | 80 |
| Glu | Gln | Glu | Trp | Tyr | Phe | Phe | Ser | Pro | Arg | Asp | Arg | Lys | Tyr | Pro | Asn |
| | | | | 85 | | | | | 90 | | | | | 95 | |
| Gly | Ala | Arg | Pro | Asn | Arg | Ala | Ala | Thr | Ser | Gly | Tyr | Trp | Lys | Ala | Thr |
| | | | 100 | | | | | 105 | | | | | 110 | | |
| Gly | Thr | Asp | Lys | Pro | Ile | Leu | Ala | Ser | Gly | Cys | Gly | Arg | Glu | Lys | Val |
| | | | 115 | | | | | 120 | | | | | 125 | | |
| Gly | Val | Lys | Lys | Ala | Leu | Val | Phe | Tyr | Arg | Gly | Lys | Pro | Pro | Lys | Gly |
| | 130 | | | | | 135 | | | | | 140 | | | | |
| Leu | Lys | Thr | Asn | Trp | Ile | Met | His | Glu | Tyr | Arg | Leu | Thr | Asp | Ala | Ser |
| 145 | | | | | 150 | | | | | 155 | | | | | 160 |
| Ser | Ser | Ala | Thr | Thr | Ser | Arg | Pro | Pro | Val | Thr | Gly | Gly | Ser | Arg |
| | | | | 165 | | | | | 170 | | | | | 175 | |
| Ser | Ala | Ser | Leu | Arg | Leu | Asp | Asp | Trp | Val | Leu | Cys | Arg | Ile | Tyr | Lys |
| | | | 180 | | | | | 185 | | | | | 190 | | |
| Lys | Ile | Asn | Lys | Ala | Ala | Ala | Gly | Asp | Gln | Gln | Arg | Ser | Met | Glu | Cys |
| | | | 195 | | | | | 200 | | | | | 205 | | |
| Glu | Asp | Ser | Val | Glu | Asp | Ala | Val | Thr | Ala | Tyr | Pro | Leu | Tyr | Ala | Thr |
| | 210 | | | | | 215 | | | | | 220 | | | | |
| Ala | Gly | Met | Thr | Gly | Ala | Gly | Ala | His | Gly | Ser | Asn | Tyr | Asp | Ser | Leu |
| 225 | | | | | 230 | | | | | 235 | | | | | 240 |
| Leu | His | His | Gln | Asp | Ser | His | Glu | Asp | Asn | Phe | Leu | Asp | Gly | Leu | Leu |
| | | | | 245 | | | | | 250 | | | | | 255 | |
| Thr | Ala | Glu | Asp | Ala | Gly | Leu | Ser | Ala | Gly | Pro | Thr | Ser | Leu | Ser | His |
| | | | 260 | | | | | 265 | | | | | 270 | | |
| Leu | Ala | Ala | Ala | Ala | Arg | Ala | Ser | Pro | Ala | Pro | Thr | Lys | Gln | Phe | Leu |
| | 275 | | | | | 280 | | | | | 285 | | | | |
| Ala | Pro | Ser | Ser | Ser | Thr | Pro | Phe | Asn | Trp | Leu | Asp | Ala | Ser | Thr | Val |
| 290 | | | | | 295 | | | | | 300 | | | | | |
| Gly | Ile | Leu | Pro | Gln | Ala | Arg | Asn | Phe | Pro | Gly | Phe | Asn | Arg | Ser | Arg |
| 305 | | | | | 310 | | | | | 315 | | | | | 320 |
| Asn | Val | Gly | Asn | Met | Ser | Leu | Ser | Ser | Thr | Ala | Asp | Met | Ala | Val | Asp |
| | | | | 325 | | | | | 330 | | | | | 335 | |
| Asn | Gly | Gly | Gly | Asn | Ala | Ile | Asn | Thr | Met | Pro | Pro | Phe | Met | Asn | His |
| | | | 340 | | | | | 345 | | | | | 350 | | |
| Leu | Pro | Met | Gln | Asp | Gly | Thr | Tyr | His | Gln | Gln | His | Val | Ile | Leu | Gly |
| | | 355 | | | | | 360 | | | | | 365 | | | |
| Ala | Pro | Leu | Ala | Pro | Glu | Ala | Thr | Ala | Ala | Ala | Thr | Ser | Ala | Phe | Gln |
| | 370 | | | | | 375 | | | | | 380 | | | | |

His Pro Val Gln Ile Ser Gly Val Asn Trp Asn Pro
385                 390                 395

<210> SEQ ID NO 11
<211> LENGTH: 1740
<212> TYPE: DNA
<213> ORGANISM: Hordeum vulgare
<220> FEATURE:
<223> OTHER INFORMATION: Hordeum vulgare cv. Optic WNAC-H1 allele
      genomic DNA
<220> FEATURE:
<221> NAME/KEY: 5'UTR
<222> LOCATION: (1)..(118)
<220> FEATURE:
<221> NAME/KEY: CDS
<222> LOCATION: join(119..362, 603..934, 1059..1703)
<223> OTHER INFORMATION: Hordeum vulgare cv. Optic WNAC-H1 allele
      predicted protein
<220> FEATURE:
<221> NAME/KEY: exon
<222> LOCATION: (119)..(362)
<220> FEATURE:
<221> NAME/KEY: intron
<222> LOCATION: (363)..(602)
<220> FEATURE:
<221> NAME/KEY: exon
<222> LOCATION: (603)..(934)
<220> FEATURE:
<221> NAME/KEY: intron
<222> LOCATION: (935)..(1058)
<220> FEATURE:
<221> NAME/KEY: exon
<222> LOCATION: (1059)..(1703)
<220> FEATURE:
<221> NAME/KEY: 3'UTR
<222> LOCATION: (1704)..(1740)

<400> SEQUENCE: 11
agctgctagc tagaagcctt ggcagttgag ttaggtgctg tgccgctgcg tttgttggtg    60
tggaagctag ctgctagcta gccaggggaa gaagaagaag atctgatcga tgaggtccat   120
gggcagcccg gactcatcct ccggctcggc gcaaaaacca ccgcggcatc agcatcagca   180
tcagccgccg cctccgcggc ggcagggctc ggcgccggag ctccctcccg gcttccggtt   240
ccacccgacg gacgaggagc tggtcgtgca ctacctcaag aagaaggccg ccaaggcgcc   300
gctccccgtc accatcatcg ccgaggtgga cctctacaag ttcgacccat gggagctccc   360
cggtatgtac tactagttag tactatgtct atccctatct cgtcgatcgt gcttgcttgc   420
tctatcaagc gccgtaattt cccggtgcaa ttaaataatc gaatccgtcc acgcatccat   480
ccatcatgct ttttattata ctgtgcacaa gtatttttat attcttccag taagtacagc   540
gcatgtatgt gatcctgtcg tcgtgcttgt tcatgcgctc gggcgggatc atcatccatc   600
agagaaggcg accttcgggg agcacagatg gtacttcttc agcccgcgcg accgcaagta   660
cgccaacggc gcgcggccga accgggcggc gacgtcgggc tactggaagg ccaccggcac   720
ggacaagcct atcctggcct cggccaccgg gtgcggccgg agaaggtcg gcgtcaagaa   780 ggcgctcgtc ttctaccgcg ggaagccgcc cagggggcctc aagaccaact ggatcatgca   840
tgagtaccgc ctcaccggag cctctgctgg ctccaccacc accagccggc cgccgccggt   900
gaccggcggg agcagggccc cggcctctct cagggtacgt acttacacgt gtccatcgca   960
cggtctatca gtatttattt attaactact ctcgagctta attatggtat tgttgatagt  1020
tgatgaagtt aattattgta cgccgtctca tcgatcagtt ggacgactgg gtgctgtgcc  1080
gcatctacaa gaagaccagc aaggccgcg ccgcggtcgg agatgagcag aggagcatgg  1140
agtgcgagga ctccgtggag gacgcggtca ccgcgtaccc gcctacgcc acggcgggca  1200

-continued

```
tggccggcgc aggtgcgcat ggcagcaact acgttcaact gctccatcat cacgacagcc    1260
acgaggacaa cttccagcta gacggcctgc tcacagaaca cgacgtcggc ctctcggcgg    1320
gcgccgcctc gctgggccac cttgccgcgg cggcgagggc caccaaacag ttcctcgccc    1380
cgtcgtcctc aaccccgttc aactggctcg aggcgtcaac cggtggcagc atcctcccac    1440
aggcaaggaa tttccctggg tttaacagga gcagaaacgt cggcagtatg tcgctgtcat    1500
ccacggccga cgacatggct ggcgcggtgg acgtcagcga cggaggcaat gcggtgaacg    1560
ccatgtatct ccccgtgcaa gacgggacct accatcagca tgtcatcctc ggagctccgc    1620
tggcgccaga ggccatcgcg ggcgccgcca cctctggttt ccagcatcac gtccaaatat    1680
ccggcgtgaa ctggaatccc tgaacgaatg acaccaacgc cacatatgcg catgcacaca    1740
```

<210> SEQ ID NO 12
<211> LENGTH: 406
<212> TYPE: PRT
<213> ORGANISM: Hordeum vulgare
<220> FEATURE:
<223> OTHER INFORMATION: Hordeum vulgare cv. Optic WNAC-H1 allele
      predicted protein
<220> FEATURE:
<221> NAME/KEY: DOMAIN
<222> LOCATION: (35)..(55)
<223> OTHER INFORMATION: conserved NAC (NAM/ATAF1/CUC2) domain
<220> FEATURE:
<221> NAME/KEY: DOMAIN
<222> LOCATION: (67)..(81)
<223> OTHER INFORMATION: conserved NAC (NAM/ATAF1/CUC2) domain
<220> FEATURE:
<221> NAME/KEY: DOMAIN
<222> LOCATION: (87)..(125)
<223> OTHER INFORMATION: conserved NAC (NAM/ATAF1/CUC2) domain
<220> FEATURE:
<221> NAME/KEY: DOMAIN
<222> LOCATION: (138)..(165)
<223> OTHER INFORMATION: conserved NAC (NAM/ATAF1/CUC2) domain
<220> FEATURE:
<221> NAME/KEY: DOMAIN
<222> LOCATION: (192)..(204)
<223> OTHER INFORMATION: conserved NAC (NAM/ATAF1/CUC2) domain

<400> SEQUENCE: 12

```
Met Gly Ser Pro Asp Ser Ser Gly Ser Ala Gln Lys Pro Pro Arg
 1               5                  10                  15

His Gln His Gln His Gln Pro Pro Pro Arg Arg Gln Gly Ser Ala
            20                  25                  30

Pro Glu Leu Pro Pro Gly Phe Arg Phe His Pro Thr Asp Glu Glu Leu
        35                  40                  45

Val Val His Tyr Leu Lys Lys Lys Ala Ala Lys Ala Pro Leu Pro Val
    50                  55                  60

Thr Ile Ile Ala Glu Val Asp Leu Tyr Lys Phe Asp Pro Trp Glu Leu
65                  70                  75                  80

Pro Glu Lys Ala Thr Phe Gly Glu His Glu Trp Tyr Phe Phe Ser Pro
                85                  90                  95

Arg Asp Arg Lys Tyr Ala Asn Gly Ala Arg Pro Asn Arg Ala Ala Thr
            100                 105                 110

Ser Gly Tyr Trp Lys Ala Thr Gly Thr Asp Lys Pro Ile Leu Ala Ser
        115                 120                 125

Ala Thr Gly Cys Gly Arg Glu Lys Val Gly Val Lys Ala Leu Val
    130                 135                 140

Phe Tyr Arg Gly Lys Pro Pro Arg Gly Leu Lys Thr Asn Trp Ile Met
145                 150                 155                 160
```

His Glu Tyr Arg Leu Thr Gly Ala Ser Ala Gly Ser Thr Thr Thr Ser
                165                 170                 175

Arg Pro Pro Pro Val Thr Gly Gly Ser Arg Ala Pro Ala Ser Leu Arg
            180                 185                 190

Leu Asp Asp Trp Val Leu Cys Arg Ile Tyr Lys Lys Thr Ser Lys Ala
        195                 200                 205

Ala Ala Ala Val Gly Asp Glu Gln Arg Ser Met Glu Cys Glu Asp Ser
    210                 215                 220

Val Glu Asp Ala Val Thr Ala Tyr Pro Pro Tyr Ala Thr Ala Gly Met
225                 230                 235                 240

Ala Gly Ala Gly Ala His Gly Ser Asn Tyr Val Gln Leu Leu His His
                245                 250                 255

His Asp Ser His Glu Asp Asn Phe Gln Leu Asp Gly Leu Leu Thr Glu
            260                 265                 270

His Asp Val Gly Leu Ser Ala Gly Ala Ala Ser Leu Gly His Leu Ala
        275                 280                 285

Ala Ala Ala Arg Ala Thr Lys Gln Phe Leu Ala Pro Ser Ser Ser Thr
    290                 295                 300

Pro Phe Asn Trp Leu Glu Ala Ser Thr Gly Gly Ser Ile Leu Pro Gln
305                 310                 315                 320

Ala Arg Asn Phe Pro Gly Phe Asn Arg Ser Arg Asn Val Gly Ser Met
                325                 330                 335

Ser Leu Ser Ser Thr Ala Asp Asp Met Ala Gly Ala Val Asp Val Ser
            340                 345                 350

Asp Gly Gly Asn Ala Val Asn Ala Met Tyr Leu Pro Val Gln Asp Gly
        355                 360                 365

Thr Tyr His Gln His Val Ile Leu Gly Ala Pro Leu Ala Pro Glu Ala
    370                 375                 380

Ile Ala Gly Ala Ala Thr Ser Gly Phe Gln His His Val Gln Ile Ser
385                 390                 395                 400

Gly Val Asn Trp Asn Pro
                405

<210> SEQ ID NO 13
<211> LENGTH: 1628
<212> TYPE: DNA
<213> ORGANISM: Hordeum vulgare
<220> FEATURE:
<223> OTHER INFORMATION: Hordeum vulgare cv. Morex WNAC-H2 allele
      genomic DNA
<220> FEATURE:
<221> NAME/KEY: 5'UTR
<222> LOCATION: (1)..(96)
<220> FEATURE:
<221> NAME/KEY: CDS
<222> LOCATION: join(97..319, 525..844, 959..1624)
<223> OTHER INFORMATION: Hordeum vulgare cv. Morex WNAC-H2 allele
      predicted protein
<220> FEATURE:
<221> NAME/KEY: exon
<222> LOCATION: (97)..(319)
<220> FEATURE:
<221> NAME/KEY: intron
<222> LOCATION: (320)..(524)
<220> FEATURE:
<221> NAME/KEY: exon
<222> LOCATION: (525)..(844)
<220> FEATURE:
<221> NAME/KEY: modified_base
<222> LOCATION: (697)
<223> OTHER INFORMATION: n = g, a, c or t
<220> FEATURE:

```
<221> NAME/KEY: intron
<222> LOCATION: (845)..(958)
<220> FEATURE:
<221> NAME/KEY: exon
<222> LOCATION: (959)..(1624)
<220> FEATURE:
<221> NAME/KEY: 3'UTR
<222> LOCATION: (1625)..(1628)

<400> SEQUENCE: 13
gccttggcag ttgagttagg caccacaata tatactctgg tgggatcatc tggtgtgttt        60
gttgttggct agctagggga aggtttgatg aggtccatgg gcagctcgga ctcatcttcc       120
ggctcggcac cgccgcggca tcagccgccg cctccgcagc agggctcggc gccggagctc       180
ccgccgggct tccggttcca ccccacagac gaggagctgg tcgtgcacta cctcaagaag       240
aaggccgcca aggtgccgct ccctgtcacc atcatcgccg aggtggatct ctacaagttc       300
gacccatggg agctccccgg tacgtatgta tgtaaatatc tcgtcgtgct tatcaagcgc       360
cgtaaatttt ccggtgcaat taaataatag atcgaatcca tcgatcatgc ttgtacacta       420
ctgtgcaaga agtattttta tattgtttca gtacacatgt atgtagatgg tttatgtatg       480
tgatcctgtc gtgcttgttc atgcgctcgc tcgggatcga tcagagaagg cgaccttcgg       540
ggagcaggag tggtacttct tcagcccgcg cgaccgcaag tatcccaacg gcgcgcggcc       600
caacagggcg gccacgtcgg ggtactggaa ggcgaccggc acgacaagc ccatcctggc        660
ctctgggtgc ggccgggaga aggtcggcgt caagaangcg ctcgtcttct accgcgggaa       720
gccgcccaag ggcctcaaaa ccaactggat catgcacgag taccgcctca ccgacgcgtc       780
tagctccgcc gccaccagcc gacctccgcc cgtgaccgga gggagcaggg ctgcctctct       840
cagggtacgt gtcgaccgat cgcacggtca agcagtaacc gatctccgta tttcagtact       900
atatcgagct tagggtattg tggttgatga agttaattgg tgcacgtcgt ctcaccagtt       960
ggatgactgg gtgctgtgcc gcatatacaa gaagatcaac aaggccgccg ccgcggatca      1020
gcagaggagc atggagtgcg aggactccgt ggaggacgcc gtcaccgcat acccgccgta      1080
tgccacagcg tgcatgaccg gtgaaggggc gcacggcagc aactacgctt cactgctcca      1140
tcaccaggac agccacgagg acaacttcct ggacggcctg ctcacagcag aggacgccgg      1200
actctcggcg ggcgccacct cgctgagcca cctagccgcg gcggcgaggg ggagcccggc      1260
tccgaccaaa cagtttctcg ccccgtcatc gtcaacccaa ttcaactggc tcgatgcgtc      1320
aaccgttggc atcctcccac atgcaaggaa ttttcctggg tttaacagga gcagaaacgt      1380
cggaaatatg tcgctgtcat cgacggccga catggctggc gcgggaacct cgcgcggtgga    1440
caacggtgga ggcaatgcga tgaacgtcat gcctccattt atgaatcatc tccccgtgca      1500
agatgggacc taccatcaac agcatgtcat cctcggcgcc ccgctcgcgc cagaagccac      1560
cggagccgcc gcctctgcct tccagcatcc cgttcaaata tccggcgtga actggaatcc      1620
ctgaacga                                                              1628

<210> SEQ ID NO 14
<211> LENGTH: 402
<212> TYPE: PRT
<213> ORGANISM: Hordeum vulgare
<220> FEATURE:
<223> OTHER INFORMATION: Hordeum vulgare cv. Morex WNAC-H2 allele
      predicted protein
<220> FEATURE:
<221> NAME/KEY: DOMAIN
<222> LOCATION: (28)..(48)
<223> OTHER INFORMATION: conserved NAC (NAM/ATAF1/CUC2) domain
```

```
<220> FEATURE:
<221> NAME/KEY: DOMAIN
<222> LOCATION: (60)..(74)
<223> OTHER INFORMATION: conserved NAC (NAM/ATAF1/CUC2) domain
<220> FEATURE:
<221> NAME/KEY: DOMAIN
<222> LOCATION: (80)..(118)
<223> OTHER INFORMATION: conserved NAC (NAM/ATAF1/CUC2) domain
<220> FEATURE:
<221> NAME/KEY: DOMAIN
<222> LOCATION: (129)..(156)
<223> OTHER INFORMATION: conserved NAC (NAM/ATAF1/CUC2) domain
<220> FEATURE:
<221> NAME/KEY: MOD_RES
<222> LOCATION: (132)
<223> OTHER INFORMATION: Xaa = Asn or Lys
<220> FEATURE:
<221> NAME/KEY: DOMAIN
<222> LOCATION: (181)..(193)
<223> OTHER INFORMATION: conserved NAC (NAM/ATAF1/CUC2) domain

<400> SEQUENCE: 14
```

Met Gly Ser Ser Asp Ser Ser Gly Ser Ala Pro Pro Arg His Gln
 1               5                  10                  15

Pro Pro Pro Gln Gln Gly Ser Ala Pro Glu Leu Pro Pro Gly Phe
            20                  25                  30

Arg Phe His Pro Thr Asp Glu Glu Leu Val Val His Tyr Leu Lys Lys
        35                  40                  45

Lys Ala Ala Lys Val Pro Leu Pro Val Thr Ile Ile Ala Glu Val Asp
    50                  55                  60

Leu Tyr Lys Phe Asp Pro Trp Glu Leu Pro Lys Ala Thr Phe Gly
65                  70                  75                  80

Glu Gln Glu Trp Tyr Phe Phe Ser Pro Arg Asp Arg Lys Tyr Pro Asn
                85                  90                  95

Gly Ala Arg Pro Asn Arg Ala Ala Thr Ser Gly Tyr Trp Lys Ala Thr
            100                 105                 110

Gly Thr Asp Lys Pro Ile Leu Ala Ser Gly Cys Gly Arg Glu Lys Val
            115                 120                 125

Gly Val Lys Xaa Ala Leu Val Phe Tyr Arg Gly Lys Pro Pro Lys Gly
    130                 135                 140

Leu Lys Thr Asn Trp Ile Met His Glu Tyr Arg Leu Thr Asp Ala Ser
145                 150                 155                 160

Ser Ser Ala Ala Thr Ser Arg Pro Pro Val Thr Gly Gly Ser Arg
                165                 170                 175

Ala Ala Ser Leu Arg Leu Asp Asp Trp Val Leu Cys Arg Ile Tyr Lys
            180                 185                 190

Lys Ile Asn Lys Ala Ala Ala Asp Gln Gln Arg Ser Met Glu Cys
            195                 200                 205

Glu Asp Ser Val Glu Asp Ala Val Thr Ala Tyr Pro Pro Tyr Ala Thr
210                 215                 220

Ala Cys Met Thr Gly Glu Gly Ala His Gly Ser Asn Tyr Ala Ser Leu
225                 230                 235                 240

Leu His His Gln Asp Ser His Glu Asp Asn Phe Leu Asp Gly Leu Leu
                245                 250                 255

Thr Ala Glu Asp Ala Gly Leu Ser Ala Gly Ala Thr Ser Leu Ser His
            260                 265                 270

Leu Ala Ala Ala Ala Arg Gly Ser Pro Ala Pro Thr Lys Gln Phe Leu
    275                 280                 285

Ala Pro Ser Ser Ser Thr Gln Phe Asn Trp Leu Asp Ala Ser Thr Val
            290                 295                 300

-continued

```
Gly Ile Leu Pro His Ala Arg Asn Phe Pro Gly Phe Asn Arg Ser Arg
305                 310                 315                 320

Asn Val Gly Asn Met Ser Leu Ser Ser Thr Ala Asp Met Ala Gly Ala
                325                 330                 335

Gly Thr Cys Ala Val Asp Asn Gly Gly Asn Ala Met Asn Val Met
            340                 345                 350

Pro Pro Phe Met Asn His Leu Pro Val Gln Asp Gly Thr Tyr His Gln
        355                 360                 365

Gln His Val Ile Leu Gly Ala Pro Leu Ala Pro Glu Ala Thr Gly Ala
    370                 375                 380

Ala Ala Ser Ala Phe Gln His Pro Val Gln Ile Ser Gly Val Asn Trp
385                 390                 395                 400

Asn Pro

<210> SEQ ID NO 15
<211> LENGTH: 2753
<212> TYPE: DNA
<213> ORGANISM: Triticum turgidum
<220> FEATURE:
<223> OTHER INFORMATION: Triticum turgidum var. dicoccoides (DIC) allele
      UCW87 gene (BAC 409D13) genomic DNA
<220> FEATURE:
<221> NAME/KEY: 5'UTR
<222> LOCATION: (1)..(45)
<220> FEATURE:
<221> NAME/KEY: variation
<222> LOCATION: (41)..(42)
<223> OTHER INFORMATION: polymorphic base between DIC and LDN alleles
<220> FEATURE:
<221> NAME/KEY: CDS
<222> LOCATION: join(46..176, 271..327, 424..1484, 1618..1888,
      1977..2346)
<223> OTHER INFORMATION: Triticum turgidum var. dicoccoides (DIC) allele
      UCW87 predicted protein
<220> FEATURE:
<221> NAME/KEY: exon
<222> LOCATION: (46)..(176)
<220> FEATURE:
<221> NAME/KEY: intron
<222> LOCATION: (177)..(270)
<220> FEATURE:
<221> NAME/KEY: exon
<222> LOCATION: (271)..(327)
<220> FEATURE:
<221> NAME/KEY: intron
<222> LOCATION: (328)..(423)
<220> FEATURE:
<221> NAME/KEY: exon
<222> LOCATION: (424)..(1484)
<220> FEATURE:
<221> NAME/KEY: variation
<222> LOCATION: (1069)
<223> OTHER INFORMATION: polymorphic base between DIC and LDN alleles
<220> FEATURE:
<221> NAME/KEY: variation
<222> LOCATION: (1217)
<223> OTHER INFORMATION: polymorphic base between DIC and LDN alleles
<220> FEATURE:
<221> NAME/KEY: variation
<222> LOCATION: (1369)
<223> OTHER INFORMATION: polymorphic base between DIC and LDN alleles
<220> FEATURE:
<221> NAME/KEY: intron
<222> LOCATION: (1485)..(1617)
<220> FEATURE:
<221> NAME/KEY: variation
<222> LOCATION: (1520)
<223> OTHER INFORMATION: polymorphic base between DIC and LDN alleles
<220> FEATURE:
<221> NAME/KEY: variation
<222> LOCATION: (1587)..(1589)
```

```
<223> OTHER INFORMATION: polymorphic base between DIC and LDN alleles
<220> FEATURE:
<221> NAME/KEY: exon
<222> LOCATION: (1618)..(1888)
<220> FEATURE:
<221> NAME/KEY: variation
<222> LOCATION: (1694)..(1697)
<223> OTHER INFORMATION: polymorphic base between DIC and LDN alleles
<220> FEATURE:
<221> NAME/KEY: variation
<222> LOCATION: (1766)
<223> OTHER INFORMATION: polymorphic base between DIC and LDN alleles
<220> FEATURE:
<221> NAME/KEY: intron
<222> LOCATION: (1889)..(1976)
<220> FEATURE:
<221> NAME/KEY: exon
<222> LOCATION: (1977)..(2346)
<220> FEATURE:
<221> NAME/KEY: 3'UTR
<222> LOCATION: (2347)..(2753)

<400> SEQUENCE: 15
catatgactc cgtacgtata acttagatac ttacgtgtgc aatgcatgca ggtggtggtg      60
gacaacgggt tggtgcaggt gtcgctgtcg aggcccgggg gccacatcac cggcgtccgc     120
tacggcgggg aagggtcgaa cctgctgcac tccagcagga gcagaaacac tggcgggtta     180
gtacatactt cacgcttgct tgcgtgttaa ttaatttgtt cttgcagtta gttaagcaag     240
atccgtatat atgatttgta cttttgcag gtactgggat atggtgtggg catccccgg      300 ctccgatcaa cgcgacttgc tcaactcgta cgtgatcgcg aattaacttg atcgcattgt     360
cttgagaaat atatgaagtg caaatactaa gctagaatcg ctatatattg tgtgcgtacg     420
taggcttgat ggttcggagt tcagggtggt aacgcagagc gacgaccagg tggagctgtc     480
gttccggagc acgtacagcc cggaacgtcg gaacggcgtc cggctcaacg tcgacaagag     540
gctagtgatg ctcaagggca gctccgggtt ctacagctac gccatcctgg agcacggcgc     600
ggacacgccg gccatcgaca tcacccaggc ccggctcgcc ttcaagctca acacggacag     660
gttcaactac atggccgtct cggacgacgt acagcgctac atgccgcggg cggctgaccg     720
ggacgcgccc cgcagctccc cgctggcgta caaggaggcg gtgctgctgg tcgacccgtc     780
ggagccacag ttcaaggggg aggtggacga caagtaccag tacacgctgg acaccaagga     840
caacagggtg cacgggtggg tcagcactag cagcggccag ccgagccacg tcggcttctg     900
ggtcgtcacc cccagcagcg agttcaagag cggcgggccg ctcaagcgag acctcacctc     960
gcatgtcggc ccgacgtgca tcagcatgtt ccatgggagg cactatatcg gggacgacat    1020
tgtggcgcgc atcggggacg gcgagcagtg gaagaaggtc atgggccctg ttttcgtcta    1080
cctcaactct aactcggaga agggagaccc gcgggtgctc tgggaggacg ctaaggcgac    1140
ggcccaggcc gaggcggcca agtggcccta cagcttcccg gagtcgcctg acttccacaa    1200
ggccggcgag agaggctctg tcaccggccg attgctcgta agggacaggt acgtgagcag    1260
ggacaacatg cccgctcggg cagcttacgt tggcctggcc gcgccaggtc agcctggctc    1320
gtgggcgacg gagagcaagg gctaccagtt ctggacgacg gcgtcgaaca cttccggcga    1380
gttcaccatt gacaacgtcc gggcaggga gtacaacctc tacgcgtggg ttcctggagt     1440
tctcggcgat tacatgaaca ccacccgcgt caccgtaaca cccggttagt accgctacca    1500
cccgctgttc tagtccaaat ttggtttggc atttgttcca gagctagtct gcatgaccag    1560
caactctggg tactgttttg ctgacgatag tttgttcgat tttcaacctt gaaacaggcg    1620
gcgcaatcaa cctcggcgat cttgtgtacg aggccccgag atcggggccg acgctgtggg    1680
```

-continued

```
agatcggcgt tcctgatcgg agcgccaagg agatgttcgt ccccgacccc gacccgaagt    1740
acctcaacaa gctcttccag aacaaagaca ggtacaggca gtacgggctg tgggagaggt    1800
acgcccaact gtacccgacg gacgatctcg tctacaccgt cggcgaaagc caccactcca    1860
aggactggta cttcgcacat gtcacaaggt aagacacacc catgggccat gggtgcattt    1920
ccacttcagt ccaagccaac ggcacaagta ctgaccgacg ttgatctgtc gtgcagaaag    1980
gccggcgacg acatcgtgcc gacgacgcgg cagatccggt tccgcatggg ccgcgtcgtg    2040 cccgcggca cctacaccett gcgcgtcgcc ctcgcggccg ctcacgcggc gaggctgcag    2100
gtccaggtga acggggggac gaggcgtggg ggcggcgtct cgggacgcc ggcgttcgga     2160 gacggcaacg cgattgcgag gcacggcgac cacggcacgc agtggagctt cgagtttccg    2220
atcagcggga gactgctccg gcaaggggac aacaccatcc acatcacgca gacgagggcg    2280
aacagcatat tcttagggggt catgtacgac tacatacggt ttgaaggacc gcccggctct    2340
tcctagaaca gagtgttttt ttttttttgaa tgatctagaa cagagttgct tgttgcttgt    2400
tgagatgttc tggaagaata atttgagcat gaatatttgt atataaataa tttccttttt    2460
catcaaattg ttaatggttg ccattgtgcg actgtcccat tatcccacaa tcgaccagcc    2520
tatcttgcac acagctaagg tcaactccag tcagtggcgg agctagacaa aaatgcttgg    2580
gggggccgaa agacaaaaaa atccaggatg agcaactgct gctgagagca aatttataat    2640
aagtgtagct gggtcttagt tgactgagac ttaaccaagc ctcggtcgaa tgctatagta    2700
tataaaaaaa ctgaagaaaa gaatgtacag ttctctatgc aagacctaag gga           2753
```

<210> SEQ ID NO 16
<211> LENGTH: 629
<212> TYPE: PRT
<213> ORGANISM: Triticum turgidum
<220> FEATURE:
<223> OTHER INFORMATION: Triticum turgidum var. dicoccoides (DIC) allele UCW87 predicted protein
<220> FEATURE:
<221> NAME/KEY: DOMAIN
<222> LOCATION: (1)..(190)
<223> OTHER INFORMATION: conserved Rhamnogalacturonate lyase domain
<220> FEATURE:
<221> NAME/KEY: VARIANT
<222> LOCATION: (466)
<223> OTHER INFORMATION: amino acid substitution between DIC and LDN alleles

<400> SEQUENCE: 16

Met Gln Val Val Asp Asn Gly Leu Val Gln Val Ser Leu Ser Arg
1               5                   10                  15

Pro Gly Gly His Ile Thr Gly Val Arg Tyr Gly Gly Glu Gly Ser Asn
            20                  25                  30

Leu Leu His Ser Ser Arg Ser Arg Asn Thr Gly Gly Tyr Trp Asp Met
        35                  40                  45

Val Trp Asp Ile Pro Gly Ser Asp Gln Arg Asp Leu Leu Asn Ser Leu
    50                  55                  60

Asp Gly Ser Glu Phe Arg Val Val Thr Gln Ser Asp Gln Val Glu
65                  70                  75                  80

Leu Ser Phe Arg Ser Thr Tyr Ser Pro Glu Arg Arg Asn Gly Val Arg
                85                  90                  95

Leu Asn Val Asp Lys Arg Leu Val Met Leu Lys Gly Ser Ser Gly Phe
            100                 105                 110

Tyr Ser Tyr Ala Ile Leu Glu His Gly Ala Asp Thr Pro Ala Ile Asp

-continued

```
            115                 120                 125
Ile Thr Gln Ala Arg Leu Ala Phe Lys Leu Asn Thr Asp Arg Phe Asn
        130                 135                 140
Tyr Met Ala Val Ser Asp Asp Val Gln Arg Tyr Met Pro Arg Ala Ala
145                 150                 155                 160
Asp Arg Asp Ala Pro Arg Ser Ser Pro Leu Ala Tyr Lys Glu Ala Val
                165                 170                 175
Leu Leu Val Asp Pro Ser Glu Pro Gln Phe Lys Gly Glu Val Asp Asp
            180                 185                 190
Lys Tyr Gln Tyr Thr Leu Asp Thr Lys Asp Asn Arg Val His Gly Trp
                195                 200                 205
Val Ser Thr Ser Ser Gly Gln Pro Ser His Val Gly Phe Trp Val Val
    210                 215                 220
Thr Pro Ser Ser Glu Phe Lys Ser Gly Gly Pro Leu Lys Arg Asp Leu
225                 230                 235                 240
Thr Ser His Val Gly Pro Thr Cys Ile Ser Met Phe His Gly Arg His
                245                 250                 255
Tyr Ile Gly Asp Asp Ile Val Ala Arg Ile Gly Asp Gly Glu Gln Trp
            260                 265                 270
Lys Lys Val Met Gly Pro Val Phe Val Tyr Leu Asn Ser Asn Ser Glu
        275                 280                 285
Lys Gly Asp Pro Arg Val Leu Trp Glu Asp Ala Lys Ala Thr Ala Gln
        290                 295                 300
Ala Glu Ala Ala Lys Trp Pro Tyr Ser Phe Pro Glu Ser Pro Asp Phe
305                 310                 315                 320
His Lys Ala Gly Glu Arg Gly Ser Val Thr Gly Arg Leu Leu Val Arg
                325                 330                 335
Asp Arg Tyr Val Ser Arg Asp Asn Met Pro Ala Arg Ala Ala Tyr Val
            340                 345                 350
Gly Leu Ala Ala Pro Gly Gln Pro Gly Ser Trp Ala Thr Glu Ser Lys
        355                 360                 365
Gly Tyr Gln Phe Trp Thr Thr Ala Ser Asn Thr Ser Gly Glu Phe Thr
        370                 375                 380
Ile Asp Asn Val Arg Ala Gly Glu Tyr Asn Leu Tyr Ala Trp Val Pro
385                 390                 395                 400
Gly Val Leu Gly Asp Tyr Met Asn Thr Thr Arg Val Thr Val Thr Pro
                405                 410                 415
Gly Gly Ala Ile Asn Leu Gly Asp Leu Val Tyr Glu Ala Pro Arg Ser
            420                 425                 430
Gly Pro Thr Leu Trp Glu Ile Gly Val Pro Asp Arg Ser Ala Lys Glu
        435                 440                 445
Met Phe Val Pro Asp Pro Asp Pro Lys Tyr Leu Asn Lys Leu Phe Gln
        450                 455                 460
Asn Lys Asp Arg Tyr Arg Gln Tyr Gly Leu Trp Glu Arg Tyr Ala Gln
465                 470                 475                 480
Leu Tyr Pro Thr Asp Asp Leu Val Tyr Thr Val Gly Glu Ser His His
                485                 490                 495
Ser Lys Asp Trp Tyr Phe Ala His Val Thr Arg Lys Ala Gly Asp Asp
            500                 505                 510
Ile Val Pro Thr Thr Arg Gln Ile Arg Phe Arg Met Gly Arg Val Val
        515                 520                 525
Pro Gly Gly Thr Tyr Thr Leu Arg Val Ala Leu Ala Ala Ala His Ala
    530                 535                 540
```

```
Ala Arg Leu Gln Val Gln Val Asn Gly Gly Thr Arg Gly Gly Gly
545                 550                 555                 560

Val Phe Gly Thr Pro Ala Phe Gly Asp Gly Asn Ala Ile Ala Arg His
                565                 570                 575

Gly Asp His Gly Thr Gln Trp Ser Phe Glu Phe Pro Ile Ser Gly Arg
            580                 585                 590

Leu Leu Arg Gln Gly Asp Asn Thr Ile His Ile Thr Gln Thr Arg Ala
        595                 600                 605

Asn Ser Ile Phe Leu Gly Val Met Tyr Asp Tyr Ile Arg Phe Glu Gly
    610                 615                 620

Pro Pro Gly Ser Ser
625

<210> SEQ ID NO 17
<211> LENGTH: 2349
<212> TYPE: DNA
<213> ORGANISM: Triticum turgidum
<220> FEATURE:
<223> OTHER INFORMATION: Triticum turgidum var. durum tetraploid
      cultivar Langdon (LDN) allele UCW87 genomic DNA
<220> FEATURE:
<221> NAME/KEY: 5'UTR
<222> LOCATION: (1)..(46)
<220> FEATURE:
<221> NAME/KEY: variation
<222> LOCATION: (41)..(43)
<223> OTHER INFORMATION: polymorphic base between DIC and LDN alleles
<220> FEATURE:
<221> NAME/KEY: CDS
<222> LOCATION: join(47..177, 272..328, 425..1485, 1621..1891,
      1980..2349)
<223> OTHER INFORMATION: Triticum turgidum var. durum tetraploid
      cultivar Langdon (LDN) allele UCW87 predicted protein
<220> FEATURE:
<221> NAME/KEY: exon
<222> LOCATION: (47)..(177)
<220> FEATURE:
<221> NAME/KEY: intron
<222> LOCATION: (178)..(271)
<220> FEATURE:
<221> NAME/KEY: exon
<222> LOCATION: (272)..(328)
<220> FEATURE:
<221> NAME/KEY: intron
<222> LOCATION: (329)..(424)
<220> FEATURE:
<221> NAME/KEY: exon
<222> LOCATION: (425)..(1485)
<220> FEATURE:
<221> NAME/KEY: variation
<222> LOCATION: (1070)
<223> OTHER INFORMATION: polymorphic base between DIC and LDN alleles
<220> FEATURE:
<221> NAME/KEY: variation
<222> LOCATION: (1370)
<223> OTHER INFORMATION: polymorphic base between DIC and LDN alleles
<220> FEATURE:
<221> NAME/KEY: intron
<222> LOCATION: (1486)..(1620)
<220> FEATURE:
<221> NAME/KEY: variation
<222> LOCATION: (1521)
<223> OTHER INFORMATION: polymorphic base between DIC and LDN alleles
<220> FEATURE:
<221> NAME/KEY: variation
<222> LOCATION: (1588)..(1592)
<223> OTHER INFORMATION: polymorphic base between DIC and LDN alleles
<220> FEATURE:
<221> NAME/KEY: exon
<222> LOCATION: (1621)..(1891)
<220> FEATURE:
<221> NAME/KEY: variation
```

<222> LOCATION: (1697)..(1700)
<223> OTHER INFORMATION: polymorphic base between DIC and LDN alleles
<220> FEATURE:
<221> NAME/KEY: variation
<222> LOCATION: (1769)
<223> OTHER INFORMATION: polymorphic base between DIC and LDN alleles
<220> FEATURE:
<221> NAME/KEY: intron
<222> LOCATION: (1892)..(1979)
<220> FEATURE:
<221> NAME/KEY: exon
<222> LOCATION: (1980)..(2349)

<400> SEQUENCE: 17

```
catatgactc cgtacgtata acttagatac ttacgtgtgc aaatgcatgc aggtggtggt    60
ggacaacggg ttggtgcagg tgtcgctgtc gaggcccggg ggccacatca ccggcgtccg   120
ctacggcggg gaagggtcga acctgctgca ctccagcagg agcagaaaca ctggcgggtt   180
agtacatact tcacgcttgc ttgcgtgtta attaatttgt tcttgcagtt agttaagcaa   240
gatccgtata tatgatttgt acttttttgca ggtactggga tatggtgtgg acatccccg   300
gctccgatca acgcgacttg ctcaactcgt acgtgatcgc gaattaactt gatcgcattg   360
tcttgagaaa tatatgaagt gcaaatacta agctagaatc gctatatatt gtgtgcgtac   420
gtaggcttga tggttcggag ttcagggtgg taacgcagag cgacgaccag gtggagctgt   480
cgttccggag cacgtacagc ccggaacgtc ggaacggcgt ccggctcaac gtcgacaaga   540
ggctagtgat gctcaagggc agctccgggt tctacagcta cgccatcctg gagcacggcg   600
cggacacgcc ggccatcgac atcacccagg cccggctcgc cttcaagctc aacacggaca   660
ggttcaacta catggccgtc tcggacgacg tacagcgcta catgccgcgg gcggctgacc   720
gggacgcgcc ccgcagctcc ccgctggcgt acaaggaggc ggtgctgctg gtcgacccgt   780
cggagccaca gttcaagggg gaggtggacg acaagtacca gtacacgctg gacaccaagg   840
acaacagggt gcacgggtgg gtcagcacta gcagcggcca gccgagccac gtcggcttct   900
gggtcgtcac ccccagcagc gagttcaaga gcggcgggcc gctcaagcga gacctcacct   960
cgcatgtcgg cccgacgtgc atcagcatgt tccatgggag gcactatatc ggggacgaca  1020
ttgtggcgcg catcggggac ggcgagcagt ggaagaaggt catgggcccc gttttcgtct  1080
acctcaactc taactcggag aagggagacc cgcgggtgct ctgggaggac gctaaggcga  1140
cggcccaggc cgaggcggcc aagtggccct acagcttccc ggagtcgcct gacttccaca  1200
aggccggcga gagaggctct gtcaccggcc gattgctcgt aagggacagg tacgtgagca  1260
gggacaacat gcccgctcgg gcagcttacg ttggcctggc cgcgccaggt cagcctggct  1320
cgtgggcgac ggagagcaag ggctaccagt tctggacgac ggcgtcgaat acttccggcg  1380
agttcaccat tgacaacgtc cgggcagggg agtacaacct ctacgcgtgg gttcctggag  1440
ttctcggcga ttcatgaac accacccgcg tcaccgtaac acccggttag taccgctacc  1500
acccgctgtt ctagtccaaa cttggttttgg catttgttcc agagctagtc tgcatgacca  1560
gcaactctgg gtactgtttt gctgacggtc tggtttgttc gattttcaac cttgaaacag  1620
gcggcgcaat caacctcggc gatcttgtgt acgaggcccc gagatcgggg ccgacgctgt  1680
gggagatcgg cgttccggac cggagcgcca aggagatgtt cgtccccgac ccgacccga   1740
agtacctcaa caagctcttc cagaacaatg acaggtacag cagtacgggg ctgtgggaga  1800
ggtacgccca actgtacccg acggacgatc tcgtctacac cgtcggcgaa agccaccact  1860
ccaaggactg gtacttcgca catgtcacaa ggtaagacac acccatgggc catgggtgca  1920
```

-continued

```
tttccacttc agtccaagcc aacggcacaa gtactgaccg acgttgatct gtcgtgcaga    1980
aaggccggcg acgacatcgt gccgacgacg cggcagatcc ggttccgcat gggccgcgtc    2040
gtgcccggcg gcacctacac cttgcgcgtc gccctcgcgg ccgctcacgc ggcgaggctg    2100
caggtccagg tgaacggggg gacgaggcgt ggggcggcg tcttcgggac gccggcgttc     2160
ggagacggca acgcgattgc gaggcacggc gaccacggca cgcagtggag cttcgagttt    2220
ccgatcagcg ggagactgct ccggcaaggg gacaacacca tccacatcac gcagacgagg    2280
gcgaacagca tattcttagg ggtcatgtac gactacatac ggtttgaagg accgcccggc    2340
tcttcctag                                                            2349
```

<210> SEQ ID NO 18
<211> LENGTH: 629
<212> TYPE: PRT
<213> ORGANISM: Triticum turgidum
<220> FEATURE:
<223> OTHER INFORMATION: Triticum turgidum var. durum tetraploid
      cultivar Langdon (LDN) allele UCW87 predicted protein
<220> FEATURE:
<221> NAME/KEY: DOMAIN
<222> LOCATION: (1)..(190)
<223> OTHER INFORMATION: conserved Rhamnogalacturonate lyase domain
<220> FEATURE:
<221> NAME/KEY: VARIANT
<222> LOCATION: (466)
<223> OTHER INFORMATION: amino acid substitution between DIC and LDN
      alleles

<400> SEQUENCE: 18

```
Met Gln Val Val Val Asp Asn Gly Leu Val Gln Val Ser Leu Ser Arg
  1               5                  10                  15

Pro Gly Gly His Ile Thr Gly Val Arg Tyr Gly Gly Glu Gly Ser Asn
             20                  25                  30

Leu Leu His Ser Ser Arg Ser Arg Asn Thr Gly Gly Tyr Trp Asp Met
         35                  40                  45

Val Trp Asp Ile Pro Gly Ser Asp Gln Arg Asp Leu Leu Asn Ser Leu
     50                  55                  60

Asp Gly Ser Glu Phe Arg Val Val Thr Gln Ser Asp Asp Gln Val Glu
 65                  70                  75                  80

Leu Ser Phe Arg Ser Thr Tyr Ser Pro Glu Arg Arg Asn Gly Val Arg
                 85                  90                  95

Leu Asn Val Asp Lys Arg Leu Val Met Leu Lys Gly Ser Ser Gly Phe
            100                 105                 110

Tyr Ser Tyr Ala Ile Leu Glu His Gly Ala Asp Thr Pro Ala Ile Asp
        115                 120                 125

Ile Thr Gln Ala Arg Leu Ala Phe Lys Leu Asn Thr Asp Arg Phe Asn
    130                 135                 140

Tyr Met Ala Val Ser Asp Asp Val Gln Arg Tyr Met Pro Arg Ala Ala
145                 150                 155                 160

Asp Arg Asp Ala Pro Arg Ser Ser Pro Leu Ala Tyr Lys Glu Ala Val
                165                 170                 175

Leu Leu Val Asp Pro Ser Glu Pro Gln Phe Lys Gly Glu Val Asp Asp
            180                 185                 190

Lys Tyr Gln Tyr Thr Leu Asp Thr Lys Asp Asn Arg Val His Gly Trp
        195                 200                 205

Val Ser Thr Ser Ser Gly Gln Pro Ser His Val Gly Phe Trp Val Val
    210                 215                 220

Thr Pro Ser Ser Glu Phe Lys Ser Gly Gly Pro Leu Lys Arg Asp Leu
```

```
            225                 230                 235                 240

Thr Ser His Val Gly Pro Thr Cys Ile Ser Met Phe His Gly Arg His
            245                 250                 255

Tyr Ile Gly Asp Asp Ile Val Ala Arg Ile Gly Asp Gly Glu Gln Trp
            260                 265                 270

Lys Lys Val Met Gly Pro Val Phe Val Tyr Leu Asn Ser Asn Ser Glu
            275                 280                 285

Lys Gly Asp Pro Arg Val Leu Trp Glu Asp Ala Lys Ala Thr Ala Gln
            290                 295                 300

Ala Glu Ala Ala Lys Trp Pro Tyr Ser Phe Pro Glu Ser Pro Asp Phe
305                 310                 315                 320

His Lys Ala Gly Glu Arg Gly Ser Val Thr Gly Arg Leu Leu Val Arg
            325                 330                 335

Asp Arg Tyr Val Ser Arg Asp Asn Met Pro Ala Arg Ala Ala Tyr Val
            340                 345                 350

Gly Leu Ala Ala Pro Gly Gln Pro Gly Ser Trp Ala Thr Glu Ser Lys
            355                 360                 365

Gly Tyr Gln Phe Trp Thr Thr Ala Ser Asn Thr Ser Gly Glu Phe Thr
            370                 375                 380

Ile Asp Asn Val Arg Ala Gly Glu Tyr Asn Leu Tyr Ala Trp Val Pro
385                 390                 395                 400

Gly Val Leu Gly Asp Tyr Met Asn Thr Thr Arg Val Thr Val Thr Pro
            405                 410                 415

Gly Gly Ala Ile Asn Leu Gly Asp Leu Val Tyr Glu Ala Pro Arg Ser
            420                 425                 430

Gly Pro Thr Leu Trp Glu Ile Gly Val Pro Asp Arg Ser Ala Lys Glu
            435                 440                 445

Met Phe Val Pro Asp Pro Asp Pro Lys Tyr Leu Asn Lys Leu Phe Gln
450                 455                 460

Asn Asn Asp Arg Tyr Arg Gln Tyr Gly Leu Trp Glu Arg Tyr Ala Gln
465                 470                 475                 480

Leu Tyr Pro Thr Asp Asp Leu Val Tyr Thr Val Gly Glu Ser His His
            485                 490                 495

Ser Lys Asp Trp Tyr Phe Ala His Val Thr Arg Lys Ala Gly Asp Asp
            500                 505                 510

Ile Val Pro Thr Thr Arg Gln Ile Arg Phe Arg Met Gly Arg Val Val
            515                 520                 525

Pro Gly Gly Thr Tyr Thr Leu Arg Val Ala Leu Ala Ala Ala His Ala
            530                 535                 540

Ala Arg Leu Gln Val Gln Val Asn Gly Gly Thr Arg Arg Gly Gly Gly
545                 550                 555                 560

Val Phe Gly Thr Pro Ala Phe Gly Asp Gly Asn Ala Ile Ala Arg His
            565                 570                 575

Gly Asp His Gly Thr Gln Trp Ser Phe Glu Phe Pro Ile Ser Gly Arg
            580                 585                 590

Leu Leu Arg Gln Gly Asp Asn Thr Ile His Ile Thr Gln Thr Arg Ala
            595                 600                 605

Asn Ser Ile Phe Leu Gly Val Met Tyr Asp Tyr Ile Arg Phe Glu Gly
            610                 615                 620

Pro Pro Gly Ser Ser
625

<210> SEQ ID NO 19
```

```
<211> LENGTH: 18
<212> TYPE: PRT
<213> ORGANISM: Artificial Sequence
<220> FEATURE:
<223> OTHER INFORMATION: Description of Artificial Sequence:UCW87 region
      including polymorphic amino acid from Triticum
      turgidum var. dicoccoides (DIC) allele

<400> SEQUENCE: 19

Leu Asn Lys Leu Phe Gln Asn Lys Asp Arg Tyr Arg Gln Tyr Gly Leu
 1               5                  10                  15

Trp Glu

<210> SEQ ID NO 20
<211> LENGTH: 18
<212> TYPE: PRT
<213> ORGANISM: Artificial Sequence
<220> FEATURE:
<223> OTHER INFORMATION: Description of Artificial Sequence:UCW87 region
      including polymorphic amino acid from Triticum
      turgidum var. durum tetraploid cultivar Langdon
      (LDN) allele

<400> SEQUENCE: 20

Leu Asn Lys Leu Phe Gln Asn Asn Asp Arg Tyr Arg Gln Tyr Gly Leu
 1               5                  10                  15

Trp Glu

<210> SEQ ID NO 21
<211> LENGTH: 18
<212> TYPE: PRT
<213> ORGANISM: Artificial Sequence
<220> FEATURE:
<223> OTHER INFORMATION: Description of Artificial Sequence:UCW87 region
      from rice (Oryza sativa) BX000498

<400> SEQUENCE: 21

Leu Asn Lys Ile Phe Ile Thr Lys Asp Lys Tyr Arg Gln Tyr Gly Leu
 1               5                  10                  15

Trp Glu

<210> SEQ ID NO 22
<211> LENGTH: 19
<212> TYPE: PRT
<213> ORGANISM: Artificial Sequence
<220> FEATURE:
<223> OTHER INFORMATION: Description of Artificial Sequence:UCW87 region
      from Arabidipsis thaliana NP_172459

<400> SEQUENCE: 22

Val Asn Lys Leu Tyr Leu Asn His Ser Asp Lys Tyr Arg Gln Tyr Gly
 1               5                  10                  15

Leu Trp Glu

<210> SEQ ID NO 23
<211> LENGTH: 20
<212> TYPE: PRT
<213> ORGANISM: Artificial Sequence
<220> FEATURE:
<223> OTHER INFORMATION: Description of Artificial Sequence:UCW87 region
      from Arabidipsis thaliana AAD15570 and AAS99719

<400> SEQUENCE: 23

Met Asn Lys Leu Tyr Val Asn Pro Leu Gln Asp Arg Phe Arg Gln Tyr
 1               5                  10                  15
```

```
<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence:UCW87 region
      from Arabidipsis thaliana CAB79353

<400> SEQUENCE: 24

Ile Asn Lys Leu Tyr Ile Gly His Pro Asp Arg Phe Arg Gln Tyr Gly
 1               5                  10                  15

Leu Trp Glu

<210> SEQ ID NO 25
<211> LENGTH: 19
<212> TYPE: PRT
<213> ORGANISM: Artificial Sequence
<220> FEATURE:
<223> OTHER INFORMATION: Description of Artificial Sequence:UCW87 region
      from rice (Oryza sativa) XP_507326 and Arabidipsis
      thaliana XP_483712

<400> SEQUENCE: 25

Val Asn Arg Leu Tyr Ile Asn His Pro Asp Arg Phe Arg Gln Tyr Gly
 1               5                  10                  15

Leu Trp Glu

<210> SEQ ID NO 26
<211> LENGTH: 19
<212> TYPE: PRT
<213> ORGANISM: Artificial Sequence
<220> FEATURE:
<223> OTHER INFORMATION: Description of Artificial Sequence:UCW87 region
      from Arabidipsis thaliana NP_172460

<400> SEQUENCE: 26

Ile Asn Asn Leu Tyr Gln Asn His Pro Asp Arg Phe Arg Gln Tyr Gly
 1               5                  10                  15

Leu Trp Glu

<210> SEQ ID NO 27
<211> LENGTH: 19
<212> TYPE: PRT
<213> ORGANISM: Artificial Sequence
<220> FEATURE:
<223> OTHER INFORMATION: Description of Artificial Sequence:UCW87 region
      from Arabidipsis thaliana NP_172462

<400> SEQUENCE: 27

Val Asn Arg Val Leu Val His His Gln Asp Arg Phe Arg Gln Tyr Gly
 1               5                  10                  15

Leu Trp Lys

<210> SEQ ID NO 28
<211> LENGTH: 3597
<212> TYPE: DNA
<213> ORGANISM: Oryza sativa
<220> FEATURE:
<223> OTHER INFORMATION: Oryza sativa OsNAC rice homologue of WNAC-B1
      genomic DNA
<220> FEATURE:
<221> NAME/KEY: 5'UTR
<222> LOCATION: (1)..(1000)
```

```
<220> FEATURE:
<221> NAME/KEY: CDS
<222> LOCATION: join(1001..1226, 1462..1799, 1885..2597)
<223> OTHER INFORMATION: Oryza sativa OsNAC rice homologue of WNAC-B1
      predicted protein
<220> FEATURE:
<221> NAME/KEY: exon
<222> LOCATION: (1001)..(1226)
<220> FEATURE:
<221> NAME/KEY: intron
<222> LOCATION: (1227)..(1461)
<220> FEATURE:
<221> NAME/KEY: exon
<222> LOCATION: (1462)..(1799)
<220> FEATURE:
<221> NAME/KEY: intron
<222> LOCATION: (1800)..(1884)
<220> FEATURE:
<221> NAME/KEY: exon
<222> LOCATION: (1885)..(2597)
<220> FEATURE:
<221> NAME/KEY: 3'UTR
<222> LOCATION: (2598)..(3597)

<400> SEQUENCE: 28
```

| | | | | | |
|---|---|---|---|---|---|
| actcctcctg | cttatctaga | accaaaatcc | agaagcagca | tttgtccgaa | attcaaaccc |     60 |
| actcattaca | gtgtgtgaac | ctttagcatt | tggggtcata | gttctattaa | accgtaccgt |    120 |
| gtctcccggg | tatatcgcag | agatagaaca | ttctattggt | aatttggtat | gcaaccagtc |    180 |
| acagtaaaaa | acaacggaag | aaatgataat | aatcaaaggt | tacacgctga | attttcatgc |    240 |
| taatcaacgt | ccaaaaggtt | gtgcttttc | tcagggaaaa | aagttaccag | tatacttta  |    300 |
| ctcttcgact | cgcggcccat | ggcctaaact | gcttcgcgtt | gtccaaagcg | agacagtgtc |    360 |
| ctaaacgggc | caacacaaaa | ggaggcctag | taagccggtg | caaattgggc | cagaaaagac |    420 |
| ggtggaagag | gttaccatac | gctgggccgt | gtgtagccca | ggaaatgggt | ggacgttggc |    480 |
| gcgcgagggg | cgggcgggcg | ggtggcgagg | tgatcgatcg | acacgcgtg  | ggggagcggc |    540 |
| ggccggcata | cgtgtccagc | ggcgacgggc | ccgtggcggc | cgcgttcggt | acaacggagc |    600 |
| cgtatttctc | ggggccaatg | ccttcggcgc | ctctccccac | accgcgcgcc | gcgcgcaccc |    660 |
| cccttgcctg | ccttgccact | gccagcccgc | acctcatcca | tcgcctcctc | ctcgatccct |    720 |
| ctcgctcgct | agcttagcat | cctgcatgca | tgcagcgcag | cggccgaaac | cgcccaaaat |    780 |
| tcccagcgca | gatcgctcgc | ctgccttgcc | tgcccgtccg | cctaaccgac | accgcaacaa |    840 |
| accacagcca | cacagcttct | ctctgttgct | cgctttactg | tgcgtgctgt | atatacaccc |    900 |
| ggtggatgag | ggatctagct | aactagctta | gctagacagc | gtgtgttggt | ggtggtggtg |    960 |
| gtgtgtgtgt | gtgtgaggag | ggtgatcgat | cgatcgagcg | atggagagcc | cggactcgtc | 1020 |
| gtccggctcg | gcgccaccgc | gagtactacg | gcggcaacag | cagcagccgg | gctcggcgcc | 1080 |
| ggagctgccg | ccgggttcc  | ggttccaccc | gacggacgag | gagctggtgg | tgcactacct | 1140 |
| caagaagaag | gccgcctccg | ttccgctccc | cgtcaccatc | atcgccgagg | tcgatctcta | 1200 |
| caagttcgat | ccctgggatc | tccccggtac | gtaatttaat | cacttacacc | cataccaatc | 1260 |
| ataaattaag | aatttattat | tacagcttat | atatactatt | atcatgcatg | tatattatct | 1320 |
| aaaaaaaatc | agcccaaatc | tccatatgca | tgtgagcatg | ctagcttgga | tgtgtagtgc | 1380 |
| tcgatcgatc | gatcgatcga | tcgatctggt | gtcgttact  | tgtttgtgcg | atttatgcgt | 1440 |
| gcatgcatcg | gtttgtatca | gagaaggcga | acttcgggga | gcaggagtgg | tatttcttca | 1500 |
| gcccgaggga | ccgcaagtac | ccgaacgggg | cgcggccgaa | ccgggcggcg | acgtcggggt | 1560 |
| actggaaggc | caccggcacc | gacaagccca | tcatgtcgtc | ggggagcacc | cgcgagaagg | 1620 |

```
tcggcgtgaa gaaggcgctc gtgttctacc ggggcaagcc acccaagggc gtcaagacta    1680
actggatcat gcacgagtac cgtctcacgg acacgtctag ctccgccgcc gccgtcgcta    1740
cgaccaggcg gccgccgccg cccatcaccg gcggtagcaa gggcgccgtc tctctcaggg    1800
tacgtacgta tatacgtttg tgcgtgacag tctcgcttgg agtcttggac tgattgatct    1860
gatcaagttg attagtgtct cagctggatg actgggtgct gtgccgcata tacaagaaga    1920
cgaacaaggc cggtgcgggg cagaggagca tggagtgcga ggactccgtg gaggacgcgg    1980
tggccgcgta cgccgtcg tcgcagcagc atgccacggc tgctgctggc atggccggtt    2040
cggacggcgc cggaggagtt gctgcagcgc acggcggcga ctacagttca ctgctccatc    2100
acgacagcca cgaggacacc ttcctcgtaa acggcctgct caccgcggag gacgccgccg    2160
gcctctcgac cggcgccagc tctctcagcc agctcgccgc ggcggcgagg gcggcggcga    2220
caccgtgcga cgccaccaag cagcttcttg ctccgtctcc aaccccattc aactggttcg    2280
aggcattcct tccacgggcc aaggagtttc ctagtgggca agcaggagt agcagagaca    2340 tcggcgacat gtcgctgtca tcgacggtgg acaggagcct gtctgaggct ggcgccgtgg    2400
ccattgacac cggcgacgcc gccaatggcg caaacactat gcctgcattt atcaatcctc    2460
tcggcgtgca gggtgcaacc taccaacaac accaagccat catgggtgcc tcgttgccat    2520
cggagtcagc agcagcagca gccgcctgca atttccagca tccgttccaa ctctccaggg    2580
tgaattggga ttcctgaata aaaggtgccg gcattatgca tacacatata tgcacatgca    2640
tacatgcatg gcttttcaag tagtagcaca acattactag taattaatca cactaatgtg    2700
tgtggcagtc gcattcagtg agcactgatc gagtagttgc atgaacacaa cactaatgca    2760
tgcactacat atatatggcc gcattgctcc tagggcacgt acctgtacga actaggtaag    2820
tgacctaacc agctagatca tgttcagaat aaggagaaga agccgcatgc aaacacgtag    2880
atcatatggc tttgccttca catgcgtttg catcatatat atcgcattca gaaagtagtg    2940
ctgcagctaa cacatagata tggtgttagc ttcatgcgtt tgtaccatat atagcggatg    3000
cagaaagtag ctagttgcac tgttcatcat tatcccatga gatatgaact ttatataacct    3060 ttggggttgc ccttctaaag tcatgcatct agagcccccc tggtaatagc atgcattgat    3120
gtttcatgcg cacatatata taattgatat atatccttgt atatacgtag gagtaattcg    3180
ctgatagaac ggcacttaca tagtacgctg tactgtacat gtaaacaaaa acttacatat    3240
tataagaaaa aacgatatta tagacacgct gcatagctag attaaccatc tgggagaaat    3300
aaagcatcta tccacgatca ctcaaaaaca aatgcatgat gcatgtgcta gcaacagtat    3360
gtattatata tggattgaat cattgaagtg catatatata tacgtagacg agttttttgtc    3420 aggctaaagc tagactagtt accaagccct tgtcgatgcc atgtgaccat gtcttccccc    3480
agcaacatgg ctgtaacaac agcactaatc ctcccaacga tctccgtcca actcgtcgcg    3540
agaccttccc tttttccgagc gtctaacagc gccaccccg tcgtccgcgc gacaaac      3597
```

<210> SEQ ID NO 29
<211> LENGTH: 425
<212> TYPE: PRT
<213> ORGANISM: Oryza sativa
<220> FEATURE:
<223> OTHER INFORMATION: Oryza sativa OsNAC rice homologue of WNAC-B1
      predicted protein
<220> FEATURE:
<221> NAME/KEY: DOMAIN
<222> LOCATION: (29)..(50)
<223> OTHER INFORMATION: conserved NAC (NAM/ATAF1/CUC2) domain

```
<220> FEATURE:
<221> NAME/KEY: DOMAIN
<222> LOCATION: (61)..(75)
<223> OTHER INFORMATION: conserved NAC (NAM/ATAF1/CUC2) domain
<220> FEATURE:
<221> NAME/KEY: DOMAIN
<222> LOCATION: (81)..(119)
<223> OTHER INFORMATION: conserved NAC (NAM/ATAF1/CUC2) domain
<220> FEATURE:
<221> NAME/KEY: DOMAIN
<222> LOCATION: (130)..(157)
<223> OTHER INFORMATION: conserved NAC (NAM/ATAF1/CUC2) domain
<220> FEATURE:
<221> NAME/KEY: DOMAIN
<222> LOCATION: (188)..(200)
<223> OTHER INFORMATION: conserved NAC (NAM/ATAF1/CUC2) domain

<400> SEQUENCE: 29

Met Glu Ser Pro Asp Ser Ser Gly Ser Ala Pro Pro Arg Val Leu
 1               5                  10                  15

Arg Arg Gln Gln Gln Gln Pro Gly Ser Ala Pro Glu Leu Pro Pro Gly
            20                  25                  30

Phe Arg Phe His Pro Thr Asp Glu Glu Leu Val Val His Tyr Leu Lys
        35                  40                  45

Lys Lys Ala Ala Ser Val Pro Leu Pro Val Thr Ile Ile Ala Glu Val
 50                  55                  60

Asp Leu Tyr Lys Phe Asp Pro Trp Asp Leu Pro Glu Lys Ala Asn Phe
 65                  70                  75                  80

Gly Glu Gln Glu Trp Tyr Phe Phe Ser Pro Arg Asp Arg Lys Tyr Pro
                85                  90                  95

Asn Gly Ala Arg Pro Asn Arg Ala Ala Thr Ser Gly Tyr Trp Lys Ala
            100                 105                 110

Thr Gly Thr Asp Lys Pro Ile Met Ser Ser Gly Ser Thr Arg Glu Lys
        115                 120                 125

Val Gly Val Lys Lys Ala Leu Val Phe Tyr Arg Gly Lys Pro Pro Lys
        130                 135                 140

Gly Val Lys Thr Asn Trp Ile Met His Glu Tyr Arg Leu Thr Asp Thr
145                 150                 155                 160

Ser Ser Ser Ala Ala Ala Val Ala Thr Thr Arg Arg Pro Pro Pro Pro
                165                 170                 175

Ile Thr Gly Gly Ser Lys Gly Ala Val Ser Leu Arg Leu Asp Asp Trp
            180                 185                 190

Val Leu Cys Arg Ile Tyr Lys Lys Thr Asn Lys Ala Gly Ala Gly Gln
        195                 200                 205

Arg Ser Met Glu Cys Glu Asp Ser Val Glu Asp Ala Val Ala Ala Tyr
210                 215                 220

Ala Pro Ser Ser Gln Gln His Ala Thr Ala Ala Ala Gly Met Ala Gly
225                 230                 235                 240

Ser Asp Gly Ala Gly Gly Val Ala Ala Ala His Gly Gly Asp Tyr Ser
                245                 250                 255

Ser Leu Leu His His Asp Ser His Glu Asp Thr Phe Leu Val Asn Gly
            260                 265                 270

Leu Leu Thr Ala Glu Asp Ala Ala Gly Leu Ser Thr Gly Ala Ser Ser
        275                 280                 285

Leu Ser Gln Leu Ala Ala Ala Arg Ala Ala Thr Pro Cys Asp
        290                 295                 300

Ala Thr Lys Gln Leu Leu Ala Pro Ser Pro Thr Pro Phe Asn Trp Phe
305                 310                 315                 320
```

```
Glu Ala Phe Leu Pro Arg Ala Lys Glu Phe Pro Ser Gly Leu Ser Arg
            325                 330                 335

Ser Ser Arg Asp Ile Gly Asp Met Ser Leu Ser Ser Thr Val Asp Arg
            340                 345                 350

Ser Leu Ser Glu Ala Gly Ala Val Ala Ile Asp Thr Gly Asp Ala Ala
            355                 360                 365

Asn Gly Ala Asn Thr Met Pro Ala Phe Ile Asn Pro Leu Gly Val Gln
            370                 375                 380

Gly Ala Thr Tyr Gln Gln His Gln Ala Ile Met Gly Ala Ser Leu Pro
385                 390                 395                 400

Ser Glu Ser Ala Ala Ala Ala Ala Cys Asn Phe Gln His Pro Phe
            405                 410                 415

Gln Leu Ser Arg Val Asn Trp Asp Ser
            420                 425

<210> SEQ ID NO 30
<211> LENGTH: 2686
<212> TYPE: DNA
<213> ORGANISM: Zea mays
<220> FEATURE:
<223> OTHER INFORMATION: Zea mays ZmNAC (partial) GSS contig
      ZmGSStuc11-12-04.2640.2 maize orthologue of
      WNAC-B1 genomic DNA
<220> FEATURE:
<221> NAME/KEY: CDS
<222> LOCATION: join(1..175, 506..825, 994..1686)
<223> OTHER INFORMATION: Zea mays ZmNAC (partial) GSS contig
      ZmGSStuc11-12-04.2640.2 maize orthologue of
      WNAC-B1 predicted protein
<220> FEATURE:
<221> NAME/KEY: exon
<222> LOCATION: (1)..(175)
<220> FEATURE:
<221> NAME/KEY: intron
<222> LOCATION: (176)..(505)
<220> FEATURE:
<221> NAME/KEY: exon
<222> LOCATION: (506)..(825)
<220> FEATURE:
<221> NAME/KEY: intron
<222> LOCATION: (826)..(993)
<220> FEATURE:
<221> NAME/KEY: exon
<222> LOCATION: (994)..(1686)
<220> FEATURE:
<221> NAME/KEY: 3'UTR
<222> LOCATION: (1687)..(2686)

<400> SEQUENCE: 30
ccaccgcaga agcagccgag ctcggcgccg gatctcccgc cgggcttccg gttccacccc      60
acggacgagg agctggtcgt ccactacctc aagaagaagg ccgcgtccgt gccactcccc     120
gtcgccatca tcgcggaggt cgacctctac aagttcgatc cgtgggagct acctggtacg     180
taaggtagcg cgcgccatat atgccgccat atacatatcc tttccaacgt gattgatgaa     240
tataatattt attggcatgg tgatctcatc ttactcattc tgctagtgat tatactgtat     300
atacagtctc gatcgtgtct attaaaatat tattatttt agtcatgtgc atatctttt       360 tcattgtaaa taaagtagta ctgtgtatat atgcgcatct actagctttg catacatact     420
gctagcttcc atgcatgcat gtgccttact attctcacgc actgtgtggc cgcctggaca     480
tgcatggttg gatactctgg atcagataag gcgacattcg gcgagcagga gtggtacttc     540
ttcagcccga gggaccgcaa gtaccccaac ggagcgcggc cgaacagggc ggcgacgtcc     600
ggctactgga aggcgactgg cacagacaag cccatcatgg cgtccggcgg caaccgcgag     660
```

```
aaggtcggcg tcaagaaggc tctcgtgttc taccgcggga agccgccaaa gggcctcaag      720
accaactgga tcatgcacga gtaccgcctc gcggatgcgg cgagctcaac caccagccgg      780
ccgccgccgc cttgcaacgc cggaggcaag gccacgtctc tcagggtatg tgtgctactt      840
tgtaaaaaaa cctgcatata caagccgatc tatagctagc ctgagattgc atcgaccaat      900
atatatgcat gcatatcaat aacctcccat aatgttttcg ctaaatataa tagctggtgt      960
ggttagttga tcaagctcta cctagtgtct cagctcgacg actgggtgtt atgccgcatc     1020
tacaagaaga tcgacaaact tggagtcggc gatccgccgc ggatcatgga gtgcggcgag     1080
gactccgtgg agaatgcggt ggcagcctac ccgacgcatg ccgcggctgc tgccatggcc     1140
gtcgcagtcg caggcggagg aggggcttac cataccggca attacacttc gctgatccac     1200
caccatcacg aggacagctt cctggtggat gggctgctca cagcagagga cgcgggcggc     1260
agctccctga gccagctagc cgcggcagcc agggcagctg ctccaacaga caccaccaag     1320
cagctcctcg tcccgtcctc caccaccccg ttcaactggc tcgacgcgtc ggcactcacg     1380
attcttccgc cggcaaagag gttccatggg tacaacagag acaccactga cggcggcggc     1440
acgtccctcc cgtcgccgtc cgagaggaat aacctgcagg cggctgtcgg cgccgtcgat     1500
agtggcgcca gcggtggcac tagtgccgtc attccatcat ttctcaatcc gctcggcgtg     1560
caaggtgcga caagctatca ccaccacgcc attttcggca caccggtgac gccggaagcc     1620
gccgcggccg ccgcatgcag tttccagcac ccctaccagc tgtccggcgt gaactggaac     1680
ccgtaaaaaa tccttgatac cgacgttgca ttggtgcata tggctggctt ttcaggtaga     1740
tcacagcatc accagcatgt agtagtacag ttgttatagt ggtagtatca ttcagtgaac     1800
cacaggacaa attaattaaa gcccatgcat attgccgcat tgcctactac gagcacgtac     1860
ctgtacggag ctctaagcaa ccgcgaacca gctggtaggg cgcgatattg agacaaaaaa     1920
tctagctagg cgagacttag cgatagatat gagatattaa ttagccatct agcctcttgc     1980
atcgtctcta tatctacaaa ttgagccctg cataaaataa tttagcctgc atgcacagtt     2040
catgacatgc ccttcagaaa acaaaattaa cagctgcttt actatgtata tatgcacggt     2100
tcacatgggc atgtagttaa caggggtaaa aatatagggg cacgtacgat aattgtattt     2160
gcatatgcat gtagataatc gtatcatcgt atgcttgatt catatatgca cacgcatggt     2220
cagtgttcat atactagcta gctagtaacc tagtactaca tacgtagata gaggatttcc     2280
gaattgagcc gcagctgttg tgtatagatc ttctcttgca atgggttggt tgctagatat     2340
gaaagccgcc gccgtcatt ggcgccatct agtactaggc acctgcaggt tgtgcgcatg     2400
catgcatgca caagatagct gcgtatgtaa tctatgtttc agctgaatta ttggactgta     2460
atgtatatac agacgagttt tagaaatggt tagaccgttt gcactatcac ctgtggtgcc     2520
atgtcacttg caccctcata tatcgtctac tgatattgag agggagagac tgagaacatg     2580
ccataacgga atctcgtcca gctagcagcc tcattcccac gtcgtgatcg ctggatcaac     2640
gctagcttac cacccgatca atggccatca tttccggcct aatact                    2686
```

<210> SEQ ID NO 31
<211> LENGTH: 395
<212> TYPE: PRT
<213> ORGANISM: Zea mays
<220> FEATURE:
<223> OTHER INFORMATION: Zea mays ZmNAC (partial) GSS contig
      ZmGSStuc11-12-04.2640.2 maize orthologue of
      WNAC-B1 predicted protein
<220> FEATURE:
<221> NAME/KEY: DOMAIN

```
<222> LOCATION: (12)..(33)
<223> OTHER INFORMATION: conserved NAC (NAM/ATAF1/CUC2) domain
<220> FEATURE:
<221> NAME/KEY: DOMAIN
<222> LOCATION: (44)..(58)
<223> OTHER INFORMATION: conserved NAC (NAM/ATAF1/CUC2) domain
<220> FEATURE:
<221> NAME/KEY: DOMAIN
<222> LOCATION: (64)..(102)
<223> OTHER INFORMATION: conserved NAC (NAM/ATAF1/CUC2) domain
<220> FEATURE:
<221> NAME/KEY: DOMAIN
<222> LOCATION: (113)..(140)
<223> OTHER INFORMATION: conserved NAC (NAM/ATAF1/CUC2) domain
<220> FEATURE:
<221> NAME/KEY: DOMAIN
<222> LOCATION: (165)..(177)
<223> OTHER INFORMATION: conserved NAC (NAM/ATAF1/CUC2) domain

<400> SEQUENCE: 31

Pro Pro Gln Lys Gln Pro Ser Ser Ala Pro Asp Leu Pro Gly Phe
 1               5                  10                  15

Arg Phe His Pro Thr Asp Glu Glu Leu Val Val His Tyr Leu Lys Lys
                20                  25                  30

Lys Ala Ala Ser Val Pro Leu Pro Val Ala Ile Ile Ala Glu Val Asp
            35                  40                  45

Leu Tyr Lys Phe Asp Pro Trp Glu Leu Pro Asp Lys Ala Thr Phe Gly
        50                  55                  60

Glu Gln Glu Trp Tyr Phe Phe Ser Pro Arg Asp Arg Lys Tyr Pro Asn
65                  70                  75                  80

Gly Ala Arg Pro Asn Arg Ala Ala Thr Ser Gly Tyr Trp Lys Ala Thr
                85                  90                  95

Gly Thr Asp Lys Pro Ile Met Ala Ser Gly Gly Asn Arg Glu Lys Val
            100                 105                 110

Gly Val Lys Lys Ala Leu Val Phe Tyr Arg Gly Lys Pro Pro Lys Gly
        115                 120                 125

Leu Lys Thr Asn Trp Ile Met His Glu Tyr Arg Leu Ala Asp Ala Ala
    130                 135                 140

Ser Ser Thr Thr Ser Arg Pro Pro Pro Cys Asn Ala Gly Gly Lys
145                 150                 155                 160

Ala Thr Ser Leu Arg Leu Asp Asp Trp Val Leu Cys Arg Ile Tyr Lys
                165                 170                 175

Lys Ile Asp Lys Leu Gly Val Gly Asp Pro Pro Arg Ile Met Glu Cys
            180                 185                 190

Gly Glu Asp Ser Val Glu Asn Ala Val Ala Ala Tyr Pro Thr His Ala
        195                 200                 205

Ala Ala Ala Ala Met Ala Val Ala Val Ala Gly Gly Gly Gly Ala Tyr
    210                 215                 220

His Thr Gly Asn Tyr Thr Ser Leu Ile His His His Glu Asp Ser
225                 230                 235                 240

Phe Leu Val Asp Gly Leu Leu Thr Ala Glu Asp Ala Gly Gly Ser Ser
                245                 250                 255

Leu Ser Gln Leu Ala Ala Ala Ala Arg Ala Ala Ala Pro Thr Asp Thr
            260                 265                 270

Thr Lys Gln Leu Leu Val Pro Ser Ser Thr Pro Phe Asn Trp Leu
        275                 280                 285

Asp Ala Ser Ala Leu Thr Ile Leu Pro Pro Ala Lys Arg Phe His Gly
    290                 295                 300

Tyr Asn Arg Asp Thr Thr Asp Gly Gly Gly Thr Ser Leu Pro Ser Pro
```

```
               305                 310                 315                 320
          Ser Glu Arg Asn Asn Leu Gln Ala Ala Val Gly Ala Val Asp Ser Gly
                          325                 330                 335

Ala Ser Gly Gly Thr Ser Ala Val Ile Pro Ser Phe Leu Asn Pro Leu
                      340                 345                 350

Gly Val Gln Gly Ala Thr Ser Tyr His His His Ala Ile Phe Gly Thr
                  355                 360                 365

Pro Val Thr Pro Glu Ala Ala Ala Ala Ala Cys Ser Phe Gln His
                  370                 375                 380

Pro Tyr Gln Leu Ser Gly Val Asn Trp Asn Pro
          385                 390                 395
```

NAC FROM WHEAT FOR INCREASING GRAIN PROTEIN CONTENT

STATEMENT AS TO RIGHTS TO INVENTIONS MADE UNDER FEDERALLY SPONSORED RESEARCH AND DEVELOPMENT

This invention was made with Government support under Grant (or Contract) No. 2001-52100-11293 awarded by the USDA-IFAFS, No. 97-36200-5272 awarded by the USDA-Fund for Rural America, and No. US-3224-01R and No. US-3573-04C awarded by BARD, The United States-Israel Binational Agricultural Research and Development Fund. The US and Israel Governments have certain rights in the invention.

FIELD OF THE INVENTION

This invention is in the field of plant breeding and plant molecular biology. In particular, this invention relates to non-naturally occurring plants with altered grain protein content and other improved characteristics.

BACKGROUND OF THE INVENTION

High grain protein content (GPC) is one of the most important factors determining pasta and breadmaking quality, and is also important to human nutrition. In addition, high protein determines premium prices for wheat in many regions of the world, making high grain protein content a primary target for hard common wheats and durum wheat breeding-programs. The emphasis on end-use quality in the current export markets has increased the value of this trait.

In spite of the economic importance of high grain protein content, genetic improvement of this trait by conventional breeding has been slow because of the complex genetic system governing this trait, the high influence of the environment and the existence of a negative correlation between GPC and yield. There is thus a need for the identification of genetic determinants of high grain protein content.

BRIEF SUMMARY OF THE INVENTION

In order to meet these needs, the present invention is directed to the sequence of the NAC genes and their use to modulate grain protein in small grain cereals.

Transgenic modifications of this gene can be used to modify the amount of protein in the grain, to alter the senescence process, and to modify the length of grain maturation and grain filling periods in wheat and barley. The promoter of the WNAC-1 gene can be used to express any type of introduced genes in leaves after anthesis.

The current invention describes a non-naturally occurring plant comprising a recombinant nucleic acid encoding a plant WNAC-1 protein, where said nucleic acid hybridizes to the nucleic acid sequence depicted in SEQ ID NO:1 or its complement under hybridization conditions that include at least one wash in 0.1×SSC and 0.1% SDS at 60-65° C. for thirty minutes, or where said nucleic acid is more than 70%, more than 80%, more than 90%, more than 95% identical or substantially identical to the nucleic acid sequence depicted in SEQ ID NOS:1, 3, 5, 7, 9, 11, 13, 15 or 17, or when the nucleic acid encodes a polypeptide which is substantially identical to the amino acid sequence depicted in SEQ ID NOS:2, 4, 6, 8, 10, 12, 14, 16 or 18, or where the nucleic acid encodes a polypeptide which is at least 70%, at least 80%, at least 90%, at least 95%, or greater than 95% identical to the amino acid sequence depicted in SEQ ID NOS:2, 4, 6, 8, 10, 12, 14, 16, or 18, or where the nucleic acid is operably linked to a promoter.

Another aspect of the invention is a non-naturally occurring plant comprising a recombinant nucleic acid encoding a plant WNAC-1 protein, where the plant is selected from the group consisting of wheat, rice, barley, rye, oats, rice maize, sorghum and forage grasses, and seeds from the transgenic plants described.

A further aspect of the invention is methods of detecting the presence or absence of a WNAC-1 allele in a plant or plant part comprising detecting the WNAC-1 gene or gene product by PCR and/or the use of a microarray, or hybridization or sequencing, or detecting WNAC-1 protein levels, structure or activity.

Another aspect of the present invention is an antibody which recognizes a WNAC-1 protein.

Another aspect of the current invention is a non-naturally occurring plant with an increased grain protein content compared to its level in a control, naturally occurring plant. The grain protein content can be increased by increasing the mRNA or protein levels encoded by a functional WNAC-1 gene (for example, SEQ ID NOS:1 and 2) in the non-naturally occurring plant compared to the mRNA or protein levels encoded by the functional WNAC-1 gene in a control, naturally occurring plant. The mRNA or protein levels can be increased by introduction of a recombinant WNAC-1 gene or a portion thereof, by mutagenesis, or by introduction of a WNAC-1 allele from a wild relative which is not present in the cultivated crop.

Another aspect of the current invention is a non-naturally occurring plant with a decreased grain protein content compared to its level in a control, naturally occurring plant. The grain protein content can be decreased by decreasing the mRNA or protein levels encoded by a functional WNAC-1 gene (for example, SEQ ID NOS:1 and 2) in the non-naturally occurring plant compared to the mRNA or protein levels encoded by the functional WNAC-1 gene in a control, naturally occurring plant. The mRNA or protein levels can be decreased by introduction of an antisense recombinant WNAC-1 gene, by RNA interference, or by mutagenesis.

Another aspect of the invention is a non-naturally occurring plant exhibiting delayed timing of senescence onset compared to the timing of senescence onset in a control, naturally occurring plant where the timing of senescence onset is delayed in said non-naturally occurring plant by reducing the in RNA or protein levels encoded by a functional WNAC-1 gene in said non-naturally occurring plant compared to the mRNA or protein levels encoded by the functional WNAC-1 gene in the control, naturally occurring plant. The mRNA or protein levels can be reduced by expression of the WNAC-1 gene or a portion thereof in the antisense orientation, or by RNA interference, or by mutagenesis.

A further aspect of the present invention is a method of increasing the rate of senescence in a plant by increasing the mRNA or protein levels encoded by a functional WNAC-1 allele, or increasing the activity of a WNAC-1 protein.

Another aspect of the invention is a method of decreasing the rate of senescence in a plant by reducing the mRNA or protein levels encoded by a functional WNAC-1 allele, or decreasing the activity of a WNAC-1 protein.

BRIEF DESCRIPTION OF THE DRAWINGS

FIG. 2 depicts a comparison of the UCW87 region (SEQ ID NOS:19-27) including the polymorphic amino acid with the most similar rice and *Arabidopsis* proteins.

FIG. 5 depicts the expression profile of OsNAC gene in Rice: Top: RT-PCR amplification using Rice-Actin primers (control). Below: amplification using genome specific primers for OsNAC. 1) leaves from seedling stage (Feekes scale 1.0). 2) leaves from tillering stage (Feekes scale 3.0). 3) leaves from stem elongation stage (Feekes scale 7.0). 4) Flag leaves at beginning of spike emergence (Feekes scale 10). 5) Flag leaf at ripening (Feekes scale 11.4). 6) rice genomic DNA control. 7) Water control.

FIG. 8 depicts the effect of WNAC-B1 on the moisture content of grains from isogenic lines of hexaploid wheat Anza (a), RSI5 (b) and tetraploid wheat Kofa (c). Black lines with solid squares represent the original recurrent parent and grey lines with open diamonds represent the corresponding isogenic line with the WNAC-B1a allele. Significant differences (P<0.05) between isogenic pairs are represented by arrows on the corresponding date. Error bars are standard errors of the means.

SEQUENCE LISTING

Figure 1:
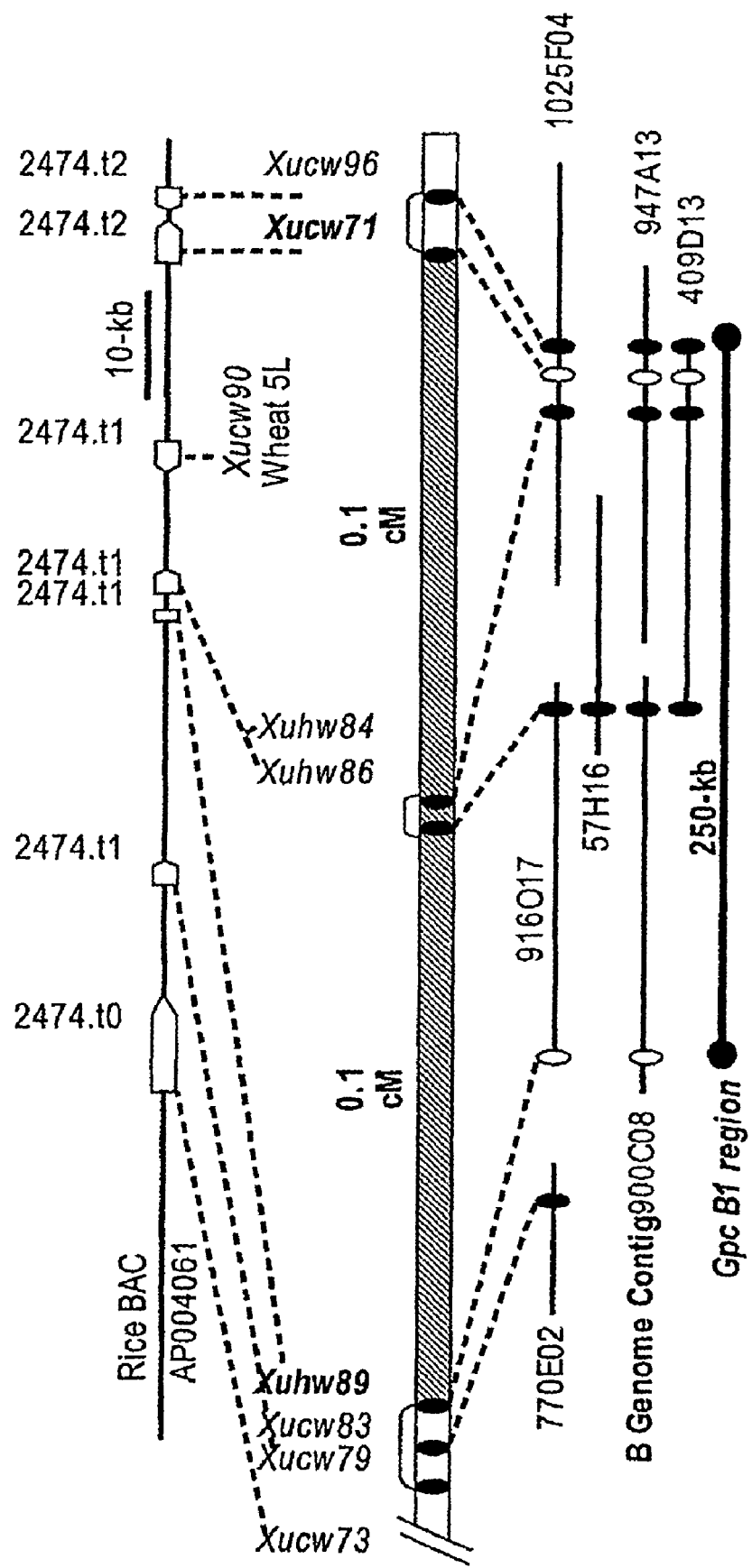
FIG. 1 depicts genetic and physical maps of the Gpc-B1 region in wheat. Top: Rice BAC AP004061. Middle: High resolution genetic map. The gray area represents the 0.2 cM region of the genetic map including the Gpc-B1 locus. Bottom: Physical map. Xuhw markers were developed at the University of Haifa and Xucw markers at the University of California at Davis.
Figure 3:
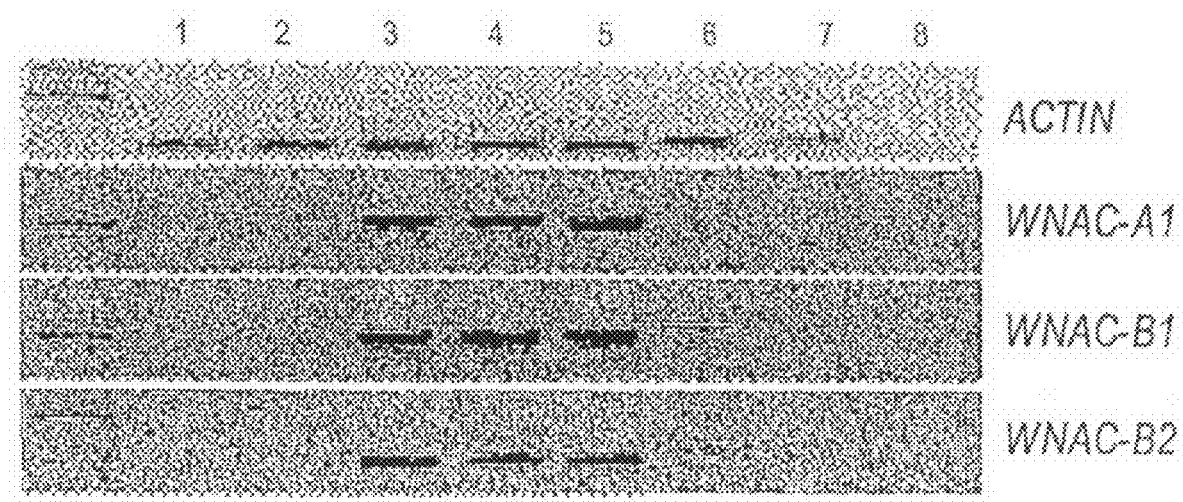
FIG. 3 depicts RT-PCR results. Top: amplification using ACTIN primers (control). Below: amplification using genome specific primers for WNAC-A1, WNAC-B1, WNAC-B2.1 & 3) RSL152 with DIC allele, rest LDN allele. 1-2) Flag leaves at beginning of spike emergence (Feekes scale 10). 3-4) Flag leaves 10 days after anthesis at medium milk stage (Feekes scale 11.1). 5) Flag leaf at ripening (Feekes scale 11.4). 6-7) Beginning of emergence of the flag leaf (Feekes scale 8), 6) yellowing leaf, 7) young green leaf 8) Water control.

SEQ ID NO:1. WNAC-B1a allele BAC 916017, chromosome 6BS. This gene corresponds to the Gpc-B1 locus. Genomic DNA sequence from the functional *Triticum turgidum* var. *dicoccoides* allele. The 5'UTR was determined by 5' race and the 3' UTR predicted by presence of a putative TAATAAATA polyadenilation signal. The sequence includes 1000-bp upstream from the start codon and 1000-bp downstream from the stop codon.

SEQ ID NO:2. Predicted protein for the WNAC-B1 a allele from the functional *Triticum turgidum* var. *dicoccoides* allele (SEQ ID NO:1). Conserved NAC domains are identified.

SEQ ID NO:3. WNAC-B1b allele, chromosome arm 6BS. Genomic DNA sequence from the *Triticum turgidum* var. *durum* non functional allele with a 1-bp frame-shift mutation.

SEQ ID NO:4. Predicted protein for the WNAC-B1b non-functional allele (SEQ ID NO:3, assuming conserved exon structure). No conserved NAC domains nor significant BLASTP results.

SEQ ID NO:5. WNAC-A1. Genomic DNA sequence from the *Triticum turgidum* var. *durum* variety Langdon from the A genome (chromosome arm 6AS).

SEQ ID NO:6. Predicted protein for the WNAC-A1 gene from the *Triticum turgidum* var. *durum* from the A genome (SEQ ID NO:5). Conserved NAC domains are indicated.

SEQ ID NO: 7. WNAC-D1. Genomic DNA sequence from the D genome (*Triticum tauschii*).

SEQ ID NO:8. Predicted protein for the WNAC-D1 gene from the D genome, *Triticum tauschii* (SEQ ID NO:7). Conserved NAC domains are indicated.

SEQ ID NO:9. WNAC-B2 allele. Genomic DNA sequence from the *Triticum turgidum* var. *durum* allele from chromosome arm 2BS.

SEQ ID NO:10. Predicted protein for the WNAC-B2 allele (SEQ ID NO:9) from *Triticum turgidum* var. *durum* chromosome arm 2BS. Conserved NAC domains are indicated.

SEQ ID NO:11. HvNAC-H1 allele. Genomic DNA sequence from the *Hordeum vulgare* cv. Optic allele from chromosome 6.

SEQ ID NO:12. Predicted protein for the HvNAC-H1 allele (SEQ ID NO:11) from *Hordeum vulgare* cv. Optic allele from chromosome 6. Conserved NAC domains are indicated.

SEQ ID NO:13. HvNAC-H2 allele. Genomic DNA sequence from the *Hordeum vulgare* cv. Morex allele.

SEQ ID NO:14. Predicted protein for the HvNAC-H2 allele (SEQ ID NO:13) from *Hordeum vulgare* cv. Morex allele. Conserved NAC domains are indicated.

SEQ ID NO:15. UCW87 BAC 409D13, chromosome arm 6BS. Genomic DNA sequence from *Triticum turgidum* var. *dicoccoides*.

SEQ ID NO:16. Predicted protein for the UCW87 gene from chromosome arm 6BS from the *Triticum turgidum* var. *dicoccoides* allele (SEQ ID NO: 15). The conserved Rhamnogalacturonate lyase domain is indicated.

SEQ ID NO:17. UCW87, chromosome arm 6BS. Genomic DNA sequence from the *Triticum turgidum* var. *durum* allele.

SEQ ID NO:18. Predicted protein for the UCW87 gene from chromosome arm 6BS from the *Triticum turgidum* var. *durum* allele (SEQ ID NO: 17). The conserved Rhamnogalacturonate lyase domain is indicated. Only one amino acid substitution (N by K) was observed between the DIC and LDN alleles.

SEQ ID NO:28. *Oryza sativa* OsNAC rice homologue of WNAC-B1.

SEQ ID NO:29. Predicted protein of *Oryza sativa* OsNAC gene (SEQ ID NO:29). Conserved NAC domains are indicated.

SEQ ID NO:30. *Zea mays* ZmNAC maize homologue of WNAC-B1.

SEQ ID NO:31. Predicted protein of *Zea mays* ZmNAC gene (SEQ ID NO:30). Conserved NAC domains are indicated.

DETAILED DESCRIPTION OF THE INVENTION

The present invention is based, at least in part, on the characterization of the high grain protein content locus Gpc-B1 in wheat. A frame shift mutation in the B genome copy of this gene located on chromosome arm 6BS is associated with the recessive gpc-B1 allele for low grain protein content. This frame shift mutation is linked to the low grain protein content in a segregating population of 3000 gametes and this non-functional mutation is the prevalent allele in the cultivated tetraploid wheats.

The WNAC-1 gene is a transcription factor with a NAC (NAM/ATAF1/CUC2) domain and is associated with leaf senescence. Transcription of this gene starts in the flag leaves at the time of anthesis and increases dramatically during senescence. The presence of the functional Gpc-B1 allele is associated with an acceleration of the senescence process, with an increase in the concentration of free amino acids and soluble protein in the flag leaves, a more efficient remobilization of nitrogen from the vegetative tissues to the grain, and significantly higher grain protein content. The cloning and characterization of this gene has provided means to clone homologues in barley (HvNAC), rice (OsNAC) and maize (ZmNAC). Natural allelic variants from these genes can be used to increase or decrease protein content in the grain of small grain cereals such as wheat, barley, oats, triticale, and sorghum, as well as rice, maize and forage grasses.

This invention includes also the natural allelic variation of NAC genes and their use to develop molecular markers for the different Gpc-B1 alleles. These markers can be used in breeding programs aimed to increase or decrease grain protein content in cereals. This invention also covers the use of antibodies against the different protein variants of the NAC genes as a diagnostic tool for cereal breeding programs. Antibody recognition can be implemented in commercial kits for easy detection of alternative Gpc-B1 alleles.

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

Throughout this disclosure, various publications, patents and published patent specifications are referenced. The disclosures of these publications, patents and published patent specifications are hereby incorporated by reference into the present disclosure to more fully describe the state of the art to which this invention pertains. The practice of the present invention will employ, unless otherwise indicated, conventional techniques of plant breeding, immunology, molecular biology, microbiology, cell biology and recombinant DNA, which are within the skill of the art. See, e.g., Sambrook, Fritsch and Maniatis, MOLECULAR CLONING: A LABORATORY MANUAL, 2nd edition (1989); CURRENT PROTOCOLS IN MOLECULAR BIOLOGY [(F. M. Ausubel, et al., eds., (1987)]; PLANT BREEDING: PRINCIPLES AND PROSPECTS (Plant Breeding, Vol 1) M. D. Hayward, N. O. Bosemark, I. Romagosa; Chapman & Hall, (1993.); Coligan, Dunn, Ploegh, Speicher and Wingfeld, eds. (1995) CURRENT PROTOCOLS IN PROTEIN SCIENCE (John Wiley & Sons, Inc.); the series METHODS IN ENZYMOLOGY (Academic Press, Inc.): PCR 2: A PRACTICAL APPROACH (M. J. MacPherson, B. D. Hames and G. R. Taylor eds. (1995)], Harlow and Lane, eds. (1988) ANTIBODIES, A LABORATORY MANUAL, and ANIMAL CELL CULTURE [R. I. Freshney, ed. (1987)].

Unless otherwise noted, technical terms are used according to conventional usage. Definitions of common terms in molecular biology may be found in Lewin, Genes V, published by Oxford University Press, 1994 (SBN 0-19-854287-9); Kendrew et al. (eds.), The Encyclopedia of Molecular Biology, published by Blackwell Science Ltd., 1994 (SBN 0-632-02182-9); and Robert A. Meyers (ed.), Molecular Biology and Biotechnology, a Comprehensive Desk Reference, published by VCH Publishers, Inc., 1995 (ISBN 1-56081-569-8); Ausubel et al. (1987) Current Protocols in Molecular Biology, Green Publishing; Sambrook et al. (1989) Molecular Cloning: A Laboratory Manual, Cold Spring Harbor, N.Y.

In order to facilitate review of the various embodiments of the invention, the following definitions are provided:

NAC proteins and genes: An NAC protein or polypeptide is a protein encoded by the NAC gene, as described herein. The NAC genes of the invention encode transcription factors which comprise an NAC domain. Exemplary conserved NAC domains of NAC proteins of the invention are identified in SEQ ID NOS:2, 6, 8, 10, 12, 29, 31. Plants with a functional NAC gene (as a non-limiting example, the WNAC-B1a allele in wheat, SEQ ID NO:1) exhibit an acceleration in the senescence process, exhibited by higher levels of soluble proteins and amino acids in the flag leaves relative to plants with a non-functional WNAC-1 gene (in wheat, the WNAC-B1b gene, SEQ ID NO:3, is an example). Soluble proteins are the results of degradation of structural or storage proteins into a form which can be transported to the grain. In particular, transgenic plants with a with increased or enhanced NAC gene expression show increased grain protein content relative to identical plants lacking the transgene.

The present invention may be practiced using nucleic acid sequences that encode full length NAC, proteins as well as NAC derived proteins that retain NAC activity. NAC derived proteins which retain NAC biological activity include fragments of NAC proteins disclosed here, generated either by chemical (e.g. enzymatic) digestion or genetic engineering means; chemically functionalized protein molecules obtained starting with the exemplified protein or nucleic acid sequences, and protein sequence variants, for example allelic variants and mutational variants, such as those produced by in vitro mutagenesis techniques, such as gene shuffling (Stemmer W P. *Nature*. 1994 Aug. 4; 370(6488):389-91 (1994a); Stemmer W P. *Proc Natl Acad Sci USA*. 1994a October 25; 91(22):10747-51 (1994b)). Thus, the term "NAC protein" encompasses full-length NAC proteins, as well as such NAC derived proteins that retain NAC activity.

Representative but non-limiting NAC sequences useful in the invention include the *Triticum turgidum* var. *dicoccoides* WNAC-B1 a DNA and protein sequences (SEQ ID NOS:1 and 2).

Also encompassed within the definition of NAC sequences include the *Triticum turgidum* var. *durum* WNAC-1B1b non-functional allele DNA and protein sequences (SEQ ID NOS:3 and 4).

Also encompassed within the definition of NAC sequences include the *Triticum turgidum* var. *durum* variety Langdon WNAC-A1 DNA and protein sequences (SEQ ID NOS:5 and 6).

Also encompassed within the definition of NAC sequences include the *Triticum tauschii* WNAC-D1 DNA and protein sequences (SEQ ID NOS:7 and 8).

Also encompassed within the definition of NAC sequences include the *Triticum turgidum* var. *durum* WNAC-B2 DNA and protein sequences (SEQ ID NOS:9 and 10).

Also encompassed within the definition of NAC sequences include the *Hordeum vulgare* cv. Optic HvNAC-H1 DNA and protein sequences (SEQ ID NOS:11 and 12).

Also encompassed within the definition of NAC sequences include the *Hordeum vulgare* cv. Morex HvNAC-H2 DNA and protein sequences (SEQ ID NOS:13 and 14).

Also encompassed within the definition of NAC sequences include the *Oryza sativa* OsNAC DNA and protein sequences (SEQ ID NOS:28 and 29).

Also encompassed within the definition of NAC sequences include the *Zea mays* ZmNAC DNA and protein sequences (SEQ ID NOS:30 and 31).

NAC Promoter: An NAC promoter is a promoter for an NAC gene of the invention. NAC promoters are generally found 5' to the NAC protein coding sequence and regulate expression of the NAC gene. Such sequences can be synthesized chemically or they can be isolated from plants. Representative plants from which NAC promoters can be isolated include wheat (spring and winter), barley, rice, and maize.

Expression cassette: A nucleic acid construct, which when introduced into a host cell, results in transcription and/or translation of a RNA or polypeptide, respectively. Antisense or sense constructs that are not or cannot be translated are expressly included by this definition. In the case of both expression of transgenes and inhibition of endogenous genes (e.g., by antisense, or sense suppression) one of skill will recognize that the inserted polynucleotide sequence need not be identical and may be "substantially identical" to a sequence of the gene from which it was derived.

Sequence Identity: As noted above, sequence variants of the sequences disclosed here are encompassed by the present invention. Either all or portions of the NAC nucleic acids or proteins or of the invention may vary from the disclosed sequences and still retain the functions disclosed here. Thus, nucleic acids or proteins of the invention may have substantial identity (as defined below) to particular domains (e.g., NAC domains) and retain the functions described here.

The similarity between two nucleic acid sequences or two amino acid sequences is expressed in terms of sequence identity (or, for proteins, also in terms of sequence similarity). Sequence identity is frequently measured in terms of percentage identity; the higher the percentage, the more similar the two sequences are. As described herein, homologs and variants of the NAC nucleic acid molecules may be used in the present invention. Homologs and variants of these nucleic acid molecules will possess a relatively high degree of sequence identity when aligned using standard methods. Such homologs and variants will hybridize under high stringency conditions to one another.

Methods of alignment of sequences for comparison are well known in the art. Various programs and alignment algorithms are described in: Smith, T. F. and Waterman, M. S., *J. Mol. Biol.*, 147:195-197 (1981); Needleman, S. B. and Wunsch, C. D., *J. Mol. Biol.*, 48:443-453 (1970); Pearson, W. R., Lipman, D. J., *Proc Natl Acad Sci U.S.A.*, 85:2444-8 (1988); Higgins, D. G. and Sharp, P. M., *Gene* 73(1):237-44 (1988); Higgins, D. G. and Sharp, P. M., *Comput Appl Biosci*. 5(2): 151-3 (1989); Corpet, F., *Nucleic Acids Res.*, 16:10881-10890 (1988); Huang X. et al., *Comput. Appl. Biosci.*, 8(2): 155-65 (1992); and Pearson W R., *Methods Mol. Biol.*, 24:307-31 (1994). Altschul, S. F. et al. (1994) Nat. Genet. 6(2):119-29 presents a detailed consideration of sequence alignment methods and homology calculations.

The NCBI Basic Local Alignment Search Tool (BLAST) (Altschul, S. F. et al. (1990) J. Mol. Bio. 215:403-410) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI Website. A description of how to determine sequence identity using this program is available at the NCBI website.

Homologs of the disclosed protein and nucleic acid sequences are typically characterized by possession of at least 40% sequence identity counted over the full length alignment with the nucleic acid or amino acid sequence of the disclosed sequence using the NCBI Blast 2.0, gapped blastp or blastn set to default parameters. For example, using blastp, the adjustable parameters are preferably set with the following values: overlap span 1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity.

Nucleic acids or proteins which are "substantially identical" to a reference sequence will show increasing percentage identities when assessed by these methods. Such nucleic acids and proteins will typically show at least about 70%, 75%, 80%, 90% or 95% sequence identity to a reference sequence.

Polypeptides that are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, aspartic acid-glutamic acid, and asparagine-glutamine.

The alignment may include the introduction of gaps in the sequences to be aligned. In addition, for sequences which contain either more or fewer amino acids than the protein encoded by the sequences in the figures, it is understood that in one embodiment, the percentage of sequence identity will be determined based on the number of identical amino acids in relation to the total number of amino acids. Thus, for example, sequence identity of sequences shorter than that shown in the figures as discussed below, will be determined using the number of amino acids in the longer sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described herein for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

As will be appreciated by those skilled in the art, the sequences of the present invention may contain sequencing errors. That is, there may be incorrect nucleotides, frameshifts, unknown nucleotides, or other types of sequencing errors in any of the sequences; however, the correct sequences will fall within the homology and stringency definitions herein.

High Stringency: Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. or 65° C. For the purposes of this disclosure, stringent conditions for hybridizations are those which include at least one wash in 0.2×SSC at 63° C. for 20 minutes, or equivalent conditions. Moderately stringent conditions include at least one wash (usually 2) in 0.2×SSC at a temperature of at least about 50° C., usually about 55° C., for 20 minutes, or equivalent conditions. High stringency conditions also refer to hybridization to filter-bound DNA in 5×SSC, 2% sodium dodecyl sulfate (SDS), 100 ug/ml single stranded DNA at 55-65° C., and washing in 0.1×SSC and 0.1% SDS at 60-65° C.

Vector: A nucleic acid molecule as introduced into a host cell, thereby producing a transformed host cell. A vector may include one or more nucleic acid sequences that permit it to replicate in one or more host cells, such as origin(s) of replication. A vector may also include one or more selectable marker genes and other genetic elements known in the art.

Transformed: A transformed cell is a cell into which has been introduced a nucleic acid molecule by molecular biology techniques. As used herein, the term transformation encompasses all techniques by which a nucleic acid molecule might be introduced into such a cell, plant or animal cell, including transfection with viral vectors, transformation by *Agrobacterium*, with plasmid vectors, and introduction of naked DNA by electroporation, lipofection, and particle gun acceleration and includes transient as well as stable transformants.

Isolated: An "isolated" biological component (such as a nucleic acid or protein or organelle) has been substantially separated or purified away from other biological components in the cell or the organism in which the component naturally occurs, i.e., other chromosomal and extra chromosomal DNA and RNA, proteins and organelles. Nucleic acids and proteins that have been "isolated" include nucleic acids and proteins purified by standard purification methods. The term embraces nucleic acids including chemically synthesized nucleic acids and also embraces proteins prepared by recombinant expression in vitro or in a host cell and recombinant nucleic acids as defined below.

Operably linked: A first nucleic acid sequence is operably linked with a second nucleic acid sequence when the first nucleic acid sequence is placed in a functional relationship with the second nucleic acid sequence. For instance, a promoter is operably linked to a protein coding sequence if the promoter affects the transcription or expression of the protein coding sequence. Generally, operably linked DNA sequences are contiguous and, where necessary, join two protein coding regions in the same reading frame. With respect to polypeptides, two polypeptide sequences may be operably linked by covalent linkage, such as through peptide bonds or disulfide bonds.

Recombinant: By "recombinant nucleic acid" herein is meant a nucleic acid that has a sequence that is not naturally occurring or has a sequence that is made by an artificial combination of two otherwise separated segments of sequence. This artificial combination is often accomplished by chemical synthesis or, more commonly, by the artificial manipulation of nucleic acids, e.g., by genetic engineering techniques, such as by the manipulation of at least one nucleic acid by a restriction enzyme, ligase, recombinase, and/or a polymerase. Once introduced into a host cell, a recombinant nucleic acid is replicated by the host cell, however, the recombinant nucleic acid once replicated in the cell remains a recombinant nucleic acid for purposes of this invention. By "recombinant protein" herein is meant a protein produced by a method employing a recombinant nucleic acid. As outlined above "recombinant nucleic acids" and "recombinant proteins" also are "isolated" as described above.

Antibody production: Methods of producing antibodies which specifically recognize a protein of interest are well known in the art. Protocols for preparing immunogens, immunization of animals, and collection of antiserum may be found in Antibodies: A Laboratory Manual, E. Harlow and D. Lane, ed., Cold Spring Harbor Laboratory (Cold Spring Harbor, N.Y., 1988) pp. 55-120.

Non-naturally Occurring Plant: A non-naturally occurring plant is a plant that does not occur in nature without human intervention. Non-naturally occurring plants include transgenic plants and plants produced by non transgenic means such as plant breeding.

Transgenic plant: As used herein, this term refers to a plant or tree that contains recombinant genetic material not normally found in plants or trees of this type and which has been introduced into the plant in question (or into progenitors of the plant) by human manipulation. Thus, a plant that is grown from a plant cell into which recombinant DNA is introduced by transformation is a transgenic plant, as are all offspring of that plant that contain the introduced transgene (whether produced sexually or asexually). It is understood that the term transgenic plant encompasses the entire plant or tree and parts of the plant or tree, for instance grains, seeds, flowers, leaves, roots, fruit, pollen, stems etc.

Orthologue: Two nucleotide or amino acid sequences are orthologues of each other if they share a common ancestral sequence and diverged when a species carrying that ancestral sequence split into two species, sub species, or cultivars. Orthologous sequences are also homologous sequences. Orthologous sequences hybridize to one another under high-stringency conditions. The term "polynucleotide", "oligonucleotide", or "nucleic acid" refers to a polymeric form of nucleotides of any length, either deoxyribonucleotides or ribonucleotides, or analogs thereof. The terms "polynucleotide" and "nucleotide" as used herein are used interchangeably. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. A "fragment" or "segment" of a nucleic acid is a small piece of that nucleic acid.

Vectors

The NAC sequences of the invention may be cloned into a suitable vector. Expression vectors are well known in the art and provide a means to transfer and express an exogenous nucleic acid molecule into a host cell. Thus, an expression vector contains, for example, transcription start and stop sites such as a TATA sequence and a poly-A signal sequence, as well as a translation start site such as a ribosome binding site and a stop codon, if not present in the coding sequence. A vector can be a cloning vector or an expression vector and provides a means to transfer an exogenous nucleic acid molecule into a host cell, which can be a prokaryotic or eukaryotic cell. Such vectors include plasmids, cosmids, phage vectors and viral vectors. Various vectors and methods for introducing such vectors into a cell are described, for example, by Sambrook et al. 1989.

The invention also provides an expression cassette containing a promoter operably linked to a protein coding sequence or to a sequence that inhibits expression of a target endogenous gene. For instance, antisense or sense suppression technology can be conveniently used. To accomplish antisense suppression, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the protein of interest, see, e.g., Sheehy et al., Proc. Natl. Acad. Sci. USA, 85:8805 8809 (1988), and Hiatt et al., U.S. Pat. No. 4,801,340. In some embodiments, small interfering RNAs are used. The phenomenon of RNA interference is described and discussed, e.g., in Bass, Nature 411:428-29 (2001); Elbahir et al., Nature 411:494-98 (2001); and Fire et al., Nature 391: 806-11 (1998), where methods of making interfering RNA also are discussed. The siRNA inhibitors are less than 100 base pairs, typically 30 bps or shorter, and are made by approaches known in the art. Introduction of expression cassettes in which a nucleic acid is configured in the sense orientation with respect to the promoter has also been shown to be an effective means by which to block the transcription of target genes. For an example of the use of this method to modulate expression of endogenous genes see, Napoli et al., The Plant Cell 2:279-289 (1990), and U.S. Pat. Nos. 5,034, 323, 5,231,020, and 5,283,184.

In the constructs of the invention, each component is operably linked to the next. For example, where the construct comprises the NAC promoter, and protein encoding sequence, preferably, the NAC protein, the NAC promoter is operably linked to the 5' end of the NAC protein encoding sequence or open reading frame.

The NAC coding sequence may be from wheat or other NAC protein coding sequences as defined herein. The protein coding sequence linked to the NAC promoter may be an NAC protein coding sequence or another heterologous protein. The heterologous proteins which find use in the invention include those that provide resistance to plant pests, facilitate translocation of nutrients, provide resistance to stresses typical of the summer: heat and dehydration, etc.

The constructs of the invention may be introduced into transgenic plants. A number of recombinant vectors suitable for stable transformation of plant cells or for the establishment of transgenic plants have been described including those described in Weissbach and Weissbach (1989), and Gelvin et al. (1990). Typically, plant transformation vectors include one or more open reading frames (ORFs) under the transcriptional control of 5' and 3' regulatory sequences and a dominant selectable marker with 5' and 3' regulatory sequences. Dominant selectable marker genes that allow for the ready selection of transformants include those encoding antibiotic resistance genes (e.g., resistance to hygromycin, kanamycin, bleomycin, G418, streptomycin or spectinomycin) and herbicide resistance genes (e.g, phosphinothricin acetyltransferase).

Standard molecular biology methods, such as the polymerase chain reaction, restriction enzyme digestion, and/or ligation may be employed to produce these constructs.

Transgenic Plants

Standard molecular biology methods and plant transformation techniques can be used to produce transgenic plants that produce plants having a recombinant NAC promoter or gene.

Introduction of the selected construct into plants is typically achieved using standard transformation techniques. The basic approach is to: (a) clone the construct into a transformation vector, which (b) is then introduced into plant cells by one of a number of techniques (e.g., electroporation, microparticle bombardment, Agrobacterium infection); (c) identify the transformed plant cells; (d) regenerate whole plants from the identified plant cells, and (e) select progeny plants containing the introduced construct.

Preferably all or part of the transformation vector will stably integrate into the genome of the plant cell. That part of the transformation vector which integrates into the plant cell and which contains the introduced recombinant sequence may be referred to as the recombinant expression cassette.

Selection of progeny plants containing the introduced transgene may be made based upon the detection of the recombinant NAC allele in transgenic plants, or upon enhanced resistance to a chemical agent (such as an antibiotic) as a result of the inclusion of a dominant selectable marker gene incorporated into the transformation vector.

Successful examples of the modification of plant characteristics by transformation with cloned nucleic acid sequences are replete in the technical and scientific literature. Selected examples, which serve to illustrate the knowledge in this field of technology include: U.S. Pat. No. 5,571,706 ("Plant Virus Resistance Gene and Methods"); U.S. Pat. No. 5,677,175 ("Plant Pathogen Induced Proteins"); U.S. Pat. No. 5,510,471 ("Chimeric Gene for the Transformation of Plants"); U.S. Pat. No. 5,750,386 ("Pathogen-Resistant Transgenic Plants"); U.S. Pat. No. 5,597,945 ("Plants Genetically Enhanced for Disease Resistance"); U.S. Pat. No. 5,589,615 ("Process for the Production of Transgenic Plants with Increased Nutritional Value Via the Expression of Modified 2S Storage Albumins"); U.S. Pat. No. 5,750,871 ("Transformation and Foreign Gene Expression in *Brassica* Species"); U.S. Pat. No. 5,268,526 ("Overexpression of Phytochrome in Transgenic Plants"); U.S. Pat. No. 5,780,708 ("Fertile Transgenic Corn Plants"); U.S. Pat. No. 5,538,880 ("Method for Preparing Fertile Transgenic Corn Plants"); U.S. Pat. No. 5,773,269 ("Fertile Transgenic Oat Plants"); U.S. Pat. No. 5,736,369 ("Method for Producing Transgenic Cereal Plants"); U.S. Pat. No. 5,610,049 ("Methods for Stable Transformation of Wheat"); U.S. Pat. No. 6,235,529 ("Compositions and Methods for Plant Transformation and Regeneration") all of which are hereby incorporated by reference in their entirety. These examples include descriptions of transformation vector selection, transformation techniques and the construction of constructs designed to express an introduced transgene.

The transgene-expressing constructs of the present invention may be usefully expressed in a wide range of grain producing higher plants where an increased grain protein content is useful. The invention is expected to be particularly applicable to monocotyledonous cereal plants including barley, wheat, rye, triticale, sorghum, oat, rice, maize and forage grasses.

Methods for the transformation and regeneration of monocotyledonous plant cells are known, and the appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG-mediated transformation); transformation using viruses; micro-injection of plant cells; micro-projectile bombardment of plant cells; vacuum infiltration; and *Agrobacterium*-mediated transformation. Typical procedures for transforming and regenerating plants are described in the patent documents listed above.

Following transformation, transformants are preferably selected using a dominant selectable marker. Typically, such a marker will confer antibiotic or herbicide resistance on the seedlings of transformed plants, and selection of transformants can be accomplished by exposing the seedlings to appropriate concentrations of the antibiotic or herbicide. After transformed plants are selected and grown the plant can be assayed for expression of recombinant proteins, increased grain protein content, using a near-infrared reflectance equipment (Technicon InfraAnalyzer model 400), micro-Kjeldahl (Bradford 1976) or other protein assays well known to those of skill in the art. Similarly, onset of senescence can be detected by assaying for chlorophyll content using standard procedures described for example in Jing, H C et al., *The Plant Journal*, 32:51-63 (2002) and Woo, H R et al., *The Plant Journal*, 31: 331-340 (2002)

Uses of the Non-Naturally Occurring Plants of the Invention

The non-naturally occurring plants of the invention have many uses, including increased or decreased grain protein content and delay or acceleration in the onset of senescence. Non-naturally occurring plants include transgenic plants and plants produced by non transgenic means such as plant breeding.

The non-naturally occurring plants of the invention are useful in that they exhibit altered grain protein content. As defined herein, altered grain protein content means that the transgenic plant will have higher or lower grain protein content than a comparable non-transgenic plant.

Other transgenic plants of the invention are useful in that they exhibit an altered rate of senescence. As defined herein, an altered rate of senescence means that the transgenic plant will senesce at a slower or higher rate than a comparable non-transgenic plant.

The protein coding sequence linked to the NAC promoter may be also any heterologous protein. Heterologous proteins useful in the invention include proteins encoded by polynucleotides from any source, natural or synthetic. Suitable coding regions encode animal RNAs or polypeptides, as well as variants, fragments and derivatives thereof. The encoded products may be recovered for use outside the host plant cell (e.g., therapeutically active products) or they may alter the phenotype of the host plant cell (e.g., conferring disease resistance, the ability to survive or grow in the presence of particular substrates). Examples of such coding regions include polynucleotides derived from vertebrates, such as mammalian coding regions for RNAs (e.g., small interfering RNAs (siRNAs) anti-sense RNAs, ribozymes, and chimeric RNAs having ribozyme structure and activity) or polypeptides (e.g., human polypeptide coding regions). Other coding regions useful in the inventive methods are derived from invertebrates (e.g., insects), plants (e.g., crop plants), and other life forms such as yeast, fungi and bacteria. The heterologous proteins which find particular use in the invention include those that provide resistance to plant pests, facilitate translocation of nutrients, provide resistance to stresses typical of the summer: heat and dehydration, etc. Such protein sequences are available in the literature and known to those of skill in the art. Representative proteins of interest are described and disclosed in Plant Biochemistry and Molecular Biology, 2nd Edition, Peter Lea and Richard C. Leegood editors; Plant Molecular Biology Second Edition; D. Grierson, S. N. Covey John Innes Institute, Norwich, U K Kluwer Academic Publishers, Dordrecht April 1991 and Biochemistry & Molecular Biology of Plants, edited, Bob B. Buchanan, Wilhelm Gruissem, and Russell L. Jones; John Wiley and Sons, Publishers, 2001, all of which are hereby incorporated by reference in their entirety.

Plants Produced by Plant Breeding

Results presented here demonstrated that the allelic variation at the NAC gene is responsible for the variation of GPC and senescence in wheat. Therefore, allelic variation at the NAC gene can be used as a molecular marker for GPC and senescence in marker assisted selection programs.

These markers can be used to transfer different NAC alleles into different germplasm by marker-assisted selection. They can also be used to determine the different haplotypes present in this region in the cultivated wheats and to establish a classification of the different haplotypes. This characterization will be useful to determine the value of the different haplotypes for grain protein content.

This invention will be better understood by reference to the following non-limiting examples.

EXAMPLE 1

Identification of Gene Responsible for High Grain Protein Content in Wheat

Background Efforts to improve GPC without selecting for low yield can be accelerated by the identification of the genes that affect GPC and the direct selection of the alleles with positive effects.

A promising source of high GPC was detected in a survey of wild populations of tetraploid *Triticum turgidum* ssp. *dicoccoides* (accession FA-15-3) referred as dicoccoides or DIC hereafter (Avivi, L., *Indian Soc. Geinet. Plant Breed.*, New Delhi, pp. 372-380 (1978)). Cantrell, R. G., and L. R. Joppa., *Crop Science* 31:645-649 (1991) developed complete sets of disomic substitution lines from each of the chromosomes of this dicoccoides accession into the tetraploid durum cultivar Langdon (LDN). The substitution of the complete chromosome 6B of DIC into LDN [LDN(DIC-6B)] showed the highest protein yield. This significant increase in GPC was not associated with a significant decrease in grain yield or kernel weight (Cantrell, R. G., and L. R. Joppa., *Crop Science* 31:645-649 (1991)). Moreover, the increase in protein content in LDN(DIC-6B) was associated with an increase in the quality of the pasta products (Joppa, L. R., *Crop Science*, 31:1513-1517 (1991)). When introduced into adapted durum germplasm, the DIC allele was also associated with an increase in protein content (15 g/Kg) with non significant effects on protein quality, plant height, or heading date (Chee, P., *Crop Science* 41:295-301 (2001)).

The evaluation of a mapping population of recombinant substitution lines (RSLs) from the cross between LDN(DIC-6B)×LDN, showed that the increase in GPC in LDN(DIC-6B) was associated with a quantitative trait locus (QTL) located on the short arm of chromosome 6B (Joppa, L. R., Crop Science, 37:1586-1589 (1997)). This QTL, designated QGpc.ndsu.6Bb, accounted for approximately 66% of variation in GPC in this cross, suggesting that a single gene or a closely linked group of genes was segregating in this population.

Other QTL studies have shown significant effects on GPC associated with markers located in similar regions of the short arms of homoeologous group 6. The Xpsr167 marker on chromosome arm 6AS ($R^2=18.4\%$) and the Nor-B2 marker on chromosome arm 6BS ($R^2=6.5\%$) were significantly associated with GPC in a cross between durum wheat cultivar 'Messapia' and a wild dicoccoides accession MG4343 (Blanco, A., et al., *Plant Molecular Biology* 48:615-623 (2002)). A significant QTL for GPC on chromosome arm 6AS in hexaploid wheat was found to be associated with AFLP marker XE38M60200 (R2=17.1%) (Sourdille, P., et al., *Theoretical & Applied Genetics* 106:530-538 (2003)). Finally, QTLs for high-GPC were reported in barley chromosome 6HS associated with GPC (Mickelson, S., et al., *Journal of Experimental Botany* 54:801-812 (2003); See, D., et al., *Crop Science*, 42:680-685 (2002)). These studies suggest that a major gene affecting GPC in the Triticeae is probably located in the short arms of the chromosomes from homoeologous group 6.

Development of PCR markers for the high GPC gene into tetraploid and hexaploid wheat cultivars (Khan, I. A., et al., *Crop Science* 40: 518-524 (2000)) Two sets of PCR primers were designed to amplify regions of the non-transcribed spacer of the XNor-B2 locus. This locus was selected because it mapped on the peak of the QTL for GPC. The first pair of allele specific primers produced an amplification product only when the DIC XNor-B2 allele was present. The second pair of primers amplified fragment(s) of similar length in the different genotypes that after digestion with the restriction enzyme Bam HI allowed differentiation of the DIC allele. Four microsatellites markers were mapped on the short arm of chromosome 6B at both sides of the QTL peak and two on the long arm. These PCR markers together with 10 RFLP markers showed that the hexaploid cultivar Glupro, selected for high GPC, carries a distal segment of chromosome 6BL and a proximal segment of 6BS from dicoccoides accession FA15-3 encompassing the segment with highest LOD score for the GPC QTL. These results demonstrated that the introgression of the DIC allele into common wheat varieties also produced high GPC levels.

Construction and characterization of a BAC library of tetraploid recombinant substitution line of durum wheat cultivar 'Langdon' carrying a 30 cM segment of chromosome 6BS from DIC carrying the allele for high grain protein content (Cenci, A., *Theor Appl Genet* 107:931-939 (2003)) A total of 516,096 clones were organized in 1344 384-well plates and blotted into 28 high-density filters. The average insert size of 500 randomly selected BAC clones was 131-kb, resulting in a coverage of 5.1× genome equivalents for each of the two genomes, and a 99.4% probability of recovering any gene from each of the two genomes of durum wheat. Six known copy number probes were used to validate this theoretical coverage and gave an estimated coverage of 5.8× genome equivalents. The main objective for the construction of this BAC library was the positional cloning of the GPC gene for high grain protein content.

Detailed mapping of the GPC gene (Olmos S., et al., *Theor. Appl. Genet.* 107:1243-1251 (2003)) A larger set of secondary recombinant substitution lines with recombination events within the QGpc.ndsu.6Bb QTL region and field trials with large number of replications to map the source of the variation in GPC as a single Mendelian locus designated Gpc-B1 (GPC-B1 gene). This locus was mapped within a 2.7-cM region encompassed by restriction fragment length polymorphism (RFLP) loci Xcdo365 and Xucw67.

The precise mapping of the Gpc-B1 locus was followed by a study on the microcolinearity between rice and wheat in the Gpc-B1 region (Distelfeld A. et al., *Functional and Integrative Genomics*. 4: 59-66 (2004)). This study facilitated the use of rice as a stepping stone for the development of new markers and for the construction of a high-density map of the region. This approach enabled to narrow down the mapping of the Gpc-B1 locus to a 0.3-cM region flanked by PCR markers for loci Xucw79 and Xucw71, which corresponds to a 64-kb region in rice genome located within Nipponbare BAC AP004061.

Physiological study comparing the tetraploid recombinant substitution line #68 (RSL#68) carrying the Gpc-B1 allele from high GPC (DIC) and the near isogenic line Langdon with the allele for low GPC. Immediately after anthesis RSL#68 had higher soluble protein and amino acids concentrations in the flag leaf than the isogenic line Langdon. At maturity, both lines presented a similar above ground biomass and grain yield. However, RSL#68 showed a higher total N content in ears, grain, and chaff than Langdon; N harvest index was also higher due to a lower straw N concentration and higher grain N concentration. It was concluded that the presence of the DIC Gpc-B1 allele resulted in a more efficient N remobilization from the leaves to the ears during grain filling.

Using the tetraploid wheat BAC library and the high-density map we constructed a complete physical map of the Gpc-B1 region including the allele from DIC for high GPC (Distelfeld A. et al., New Phlytologist, 169:753-763 (2006)). The chromosome walk was initiated with the closest proximal marker (Xucw71) and was completed with the identification of overlapping BACs 409D13 and 916017 that formed a contig of approximately 250-kb that includes Xuhw84. The Xuhw89 locus corresponding to the distal end of BAC clone 916017 was mapped 0.1 cM distal to the Gpc-B1 locus. Based on these results it was concluded that the GPC-B1 gene is located within the 250-kb physical contig delimited by loci Xucw71 and Xuhw89. A high-throughput PCR marker was developed for the Xuhw89 locus to facilitate the introgression of this gene into commercial varieties by marker assisted selection. The polymorphism for the Xuhw89 locus was validated in a large collection of tetraploid and hexaploid wheat germplasm.

Identification of WNAC-1 as the gene responsible for high GPC

Sequencing of the Gpc-B1 physical contig The BACs 409D13 (1030 sub-clones both directions, 10.8× coverage) and 916017 (1270 sub-clones both directions, 20× coverage) were sequenced from the RSL#65 BAC library. These two BACs included the Gpc-B1 flanking loci Xuhw89 and Xucw71 and therefore, the Gpc-B1 gene. The ends of these two BACs overlapped on a 32,224-bp region (100% identical) confirming the connection predicted by the physical map. The sequence of the complete contig was approximately 245-kb.

BAC 409D13 proximal end included part of wheat gene UCW96 (FIG. 1). Wheat gene UCW96 was separated by 856-bp from gene UCW71 which was also close (1142-bp) to gene UHW84. These three wheat genes were in the same orientation as the colinear rice genes 2474.t23, 22474.t22 and 2474.t14, which where the most similar genes in the rice genome, confirming that these three pairs of genes were orthologous (FIG. 1). The region between 22474.t22 and 2474.t14 was larger in rice and included an additional gene 22474.t17, which was mapped in a different wheat chromosome (5L). A non-colinear wheat gene, designated UCW97, was predicted by Genscan 7,440-bp distal to UHW84. The predicted UCW97 protein includes a leucine-rich repeat (LRR), ribonuclease inhibitor (R1)-like domain (amino acids 278-448, cd00116, E=5e−6) and also showed similarity to a leucine-rich repeat (LRR) (domain COG4886, E=1e−8) between amino acids 504 to 831. This predicted gene was not supported by ESTs. The best match in the Triticum EST collection CA733412.1, showed a low level of identity (84%) to be considered a real orthologue.

An additional wheat gene that was not colinear with the rice genes was identified 38.6-kb distal to UCW97 in BAC 409D13. This putative wheat gene, designated UCW87 (SEQ ID NOS:15 and 16), includes a Rhamnogalacturonate lyase domain (pfam06045, first 190 amino acids, E=1e−56). This domain is characteristic of proteins that degrade the rhamnogalacturonan I (RG-I) backbone of pectin. This family contains mainly members from plants, but also contains the plant pathogen Erwinia chrysanthemi. The closest homologues in plants are Arabidopsis NP_172459.1 (68% similarity, E=0) and rice BACBX000498 (79% similar, E=0, chromosome 12). The wheat protein differs from both the rice and the Arabidopsis genes by the absence of introns three to seven. The large exon three from the predicted wheat protein corresponds to exons three to eight in the rice and Arabidopsis putative orthologous proteins.

Figure 4:
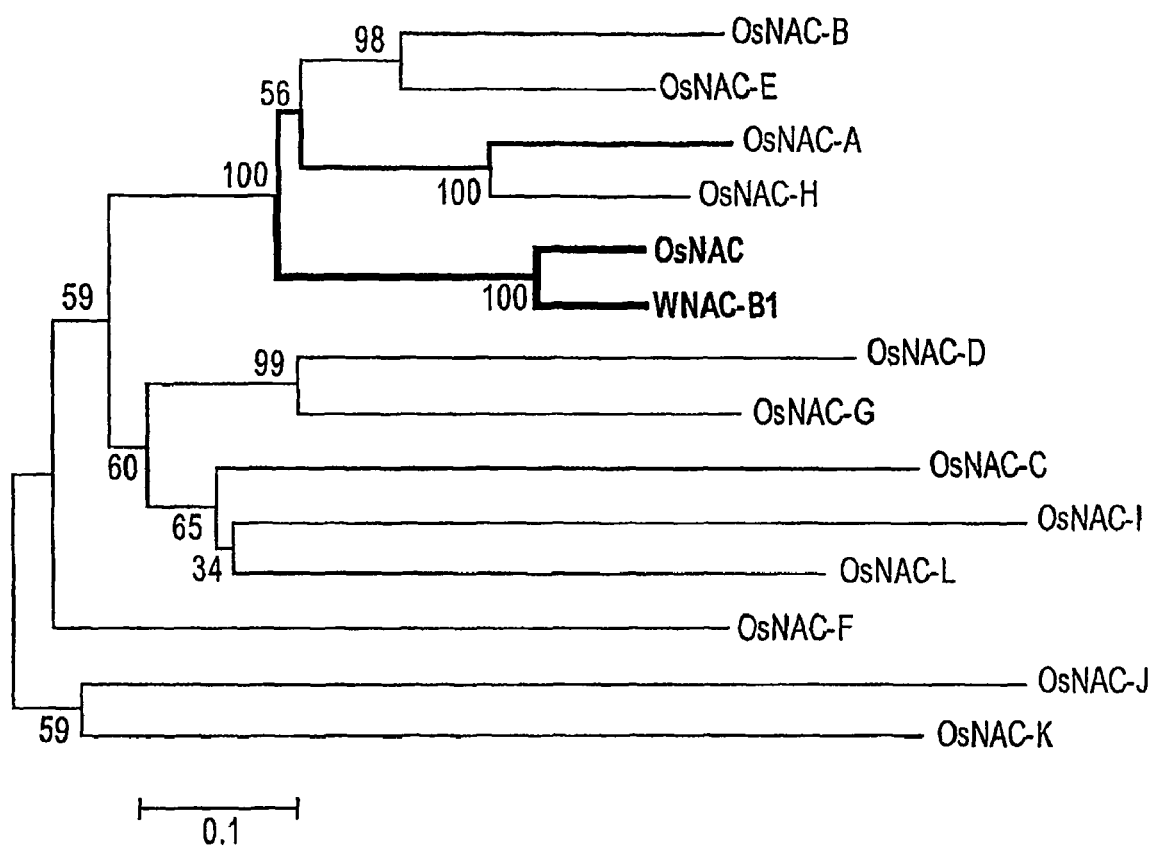
FIG. 4 depicts a phylogenetic analysis of rice NAC proteins and wheat WNAC-B1. Following the red clade, WNAC-B1 clusters alongside of OsNAC. The closest homologue of OsNAC in rice, OsNAC-A, clusters on a separate branch. Analysis done with neighbor-joining method in MEGA3. The numbers beside the branches represent bootstrap values based on 250 replications.

BAC 916017 revealed the presence of one additional wheat gene that was not colinear with the rice genes. This gene designated WNAC-B1 (SEQ ID NOS:1 and 2) includes a NAM domain (pfam 02365, E=2e−57) characteristic of a large family of plant NAC transcription factors. Reported herein are also the orthologous WNAC-1 copies for the A genome (SEQ ID NOS:5 and 6), D genome (SEQ ID NOS:7 and S), and H genome from barley (SEQ ID NOS:11 and 12). A paralogous copy of this gene designated WNAC-B2 (SEQ ID NOS:9 and 10) was mapped in the centromeric region of the short arm of wheat homoeologous group 2B using deletion lines. This paralogous gene is 91% identical at the DNA level to WNAC-B1 suggesting a relatively recent duplication. The paralogous WNAC-2 copy was also found in barley (FIG. 4, SEQ ID NO:13 and 14). The closest rice gene in rice is OsNAC5, which was mapped on rice chromosome 7 (BAC AP003932) in a region colinear to the centromeric bin of the short arm of wheat chromosome 2. This result suggests that the WNAC-2 copy in wheat is the ancestral gene and that the WNAC-1 is the result of a duplication that occurred in the Triticeae lineage after the Triticeae—rice divergence but before the wheat—barley divergence. The closest rice gene in rice in further described in Example 3. The Arabidopsis NAC genes more closely related to the WNAC-1 gene belong to the NAP subgroup (Ooka, H., et al., DNA Research 10:239-247 (2003)).

Screening for additional recombinant lines to reduce the number of candidate genes To further reduce the list of candidate genes a total of 3,000 gametes from the cross LDN×RSL65 were screened. F2-3 lines to identify recombinants between flanking markers Xuhw89 and Xucw71. Only 4 lines showed recombination between flanking markers Xuhw89 and Xucw71: RSL121, RSL152, RSL300, and RSL28 (Table 1).

TABLE 1

Molecular characterization of critical recombinant lines and linkage with the phenotype (Gpc-B1 locus) for high grain protein content.

| RSL | UCW 79 | UCW 83 | Xuhw 89 | WNAC -1 | Gpc-B1 | UCW 87 | UCW 97 | UHW | UCW 71 | UCW 96 |
|---|---|---|---|---|---|---|---|---|---|---|
| 121 | L | L | L | D | H-GPC D | D | D | D | D | D |
| 300 | D | D | D | D | H-GPC D | D | L | L | L | L |
| 152 | D | D | D | D | H-GPC D | D | D | D | L | L |
| 28 | D | D | D | D | H-GPC D | D | D | D | L | L |

*D = DIC alleles, L = LDN alleles. A change between gray and white cells indicates a recombination event.

The Gpc-B1 genotype can be accurately evaluated using near isogenic lines segregating only for the 30-cM of the GPC QTL region, combined with 10 replications (1 m rows) organized in a split plot experimental designs (Olmos S., et al., Theor. Appl. Genet. 107:1243-1251 (2003)). The same procedures were used to evaluate the critical lines in at least two independent experiments (Table 1). A line was classified as low-GPC if it was simultaneously significantly lower (P<0.01) than the high-GPC group and non-significantly (NS) different from the low-GPC group. A line was classified as high-GPC if it was simultaneously significantly higher (P<0.01) than the low-GPC control group and NS different from the high-GPC control group. To further validate the GPC determinations the critical lines were backcrossed again to Langdon (low GPC) and sister homozygous lines from the progeny with alternative alleles were compared against each other.

For example, 19 independent RSL300-derived homozygous recombinant lines were compared to both high- (P=0.9478) and low-GPC controls (P<0.001) and also to sister RSL300 lines for which the non recombinant chromosome DIC segment was fixed (P=0.6394). These results demonstrated that the recombinant chromosome in RSL300 carries the WNAC-B1 a allele for high grain protein, and therefore eliminated UCW97 and UHW84 as candidate genes for the Gpc-B1 locus.

In summary, the high-density genetic map combined with the sequencing of the physical contig showed that the Gpc-B1 locus is proximal to the Xuhw89 locus and distal to the Xucw97 locus (Table 1). Only the WNAC-1 gene and the UCW87 putative gene were completely linked to the segregation for GPC and therefore, were the only candidate genes for the Gpc-B1 locus.

Allelic variation at the WNAC-1 and UCW87 candidate genes To determine which of these two genes is Gpc-B1, the allelic variation between the DIC (high-protein parent) and LDN (low protein parent) was analyzed for both the UCW87 and WNAC-B1 candidate genes from chromosome 6B.

UCW87: The DNA genomic sequence of wheat UCW87 for both LDN and DIC alleles showed that the large exon 3 from wheat corresponded to exons 3 to 8 in the rice and Arabidopsis closely related genes (SEQ ID NOS:15 and 17). It is not known if this large structural change affected the functionality of this wheat gene.

The predicted UCW87 protein from the high-GPC parent (SEQ ID NO:16) shows only one amino acid difference relative to the predicted protein of the low-GPC parent (LDN, SEQ ID NO:18). This K (DIC) to N (LDN) mutation is outside the functional Rhamnogalacturonate lyase domain and therefore is not likely to affect the function of this domain. In addition, this mutation involves two polar amino acids with similar hydrophobicity and has therefore, a low probability to alter the protein folding. A K to N mutation is regarded as neutral in the BLOSUM 62 matrix for amino acid substitutions. Finally, a BLASTP analysis of the most similar proteins to UCW87 revealed that the polymorphic K/N amino acids are not located in a conserved position in the protein, suggesting that this amino acid is not critical for the protein function.

In summary, the single amino acid substitution observed between the LDN and DIC UCW87 proteins does not seem to be sufficient to explain the large phenotypic differences observed between the parental lines.

WNAC-B1: On the contrary, a significant difference was observed between the LDN and DIC alleles for the 6BS WNAC-B1 gene. The DIC allele for WNAC-B1, designated WNAC-B1a hereafter (SEQ ID NO:1), showed the five conserved domains characteristic of the NAC transcription factors (SEQ ID NO:2). However, the LDN allele, designated WNAC-B1b showed a 1-bp T insertion after the first 10-bp of the gene (FIG. 4, SEQ ID NO:3) that results in a frame-shift mutation that completely alter the WNAC-1 protein after the third amino acid (SEQ ID NO:4). This mutation is sufficient to produce a non-functional protein for the B genome copy of this transcription factor. Even though there is a second functional copy of the WNAC-1 transcription factor in the A genome, the abundance of functional WNAC-1 protein would be reduced in the plants carrying the LDN allele.

The WNAC-B1b allele associated with low protein content is widely distributed among the cultivated durum varieties. A survey of a world collection of 54 durum lines (Maccaferri, et al., Theor Appl Genet 107:783-797 (2003)) with a molecular marker for the frame-shift mutation revealed that all the tested durum cultivated varieties have the non functional WNAC-B1b allele for low protein content (Table 2). This result indicates that the introduction of the WNAC-B1 a allele from DIC into the cultivated durum varieties has the potential to increase GPC in a large set of tetraploid varieties.

TABLE 2

Durum varieties carrying the WNAC-B1b allele with the frame-shift mutation.

| VARIETY | COUNTRY |
| --- | --- |
| Dunfati | |
| Edolic | |
| Durfort | FRANCE |
| Exeldur | FRANCE |
| Nefer | FRANCE |
| Neodur | FRANCE |
| Minos | GREECE |
| Adamello | ITALY |
| Appio | ITALY |
| Capelli | ITALY |
| Ciccio | ITALY |
| Cirillo | ITALY |
| Colosseo | ITALY |
| Duilio | ITALY |
| Karel | ITALY |
| L35 | ITALY |
| Latino | ITALY |
| Messapia | ITALY |
| Ofanto | ITALY |
| Russello sg7 | ITALY |
| San carlo | ITALY |
| Saragolla | ITALY |
| Trinakria | ITALY |
| Valbelice | ITALY |
| Valforte | ITALY |
| Valnova | ITALY |
| Varano | ITALY |
| Zenit | ITALY |
| Appulo | ITALY |
| Vitron | SPAIN |
| Aconchi 89 | MEXICO |
| Altar 84 | MEXICO |
| Carcomun 's' | MEXICO |
| Mexicali 75 | MEXICO |
| Inrat 69 | TUNISIA |
| Karim | TUNISIA |
| Khiar | TUNISIA |
| Aldura | USA |
| Aruba | USA |
| Colorado | USA |
| Duraking | USA |
| Durex | USA |
| Imperial | USA |
| Kofa | USA |
| Kronos | USA |
| Langdon | USA |
| Leeds | USA |

TABLE 2-continued

Durum varieties carrying the WNAC-B1b
allele with the frame-shift mutation.

| VARIETY | COUNTRY |
|---|---|
| Ocotillo | USA |
| Produra | USA |
| Reva | USA |
| Ria | USA |
| UC1112 | USA |
| UC1113 | USA |
| Wb 881 | USA |

Two isogenic lines of tetraploid wheat were developed by backcrossing the WNAC-B1a allele into the durum lines Kofa and UC1113 (which have the nonfunctional WNAC-B1b allele) by six backcross generations followed by selection of homologous lines using molecular markers. In a Randomized Complete Block Design (RCBD) experiment with 10 replications (Buenos Aires, Argentina, 2004) it was demonstrated that the lines with the introgressed WNAC-B1a allele showed significantly higher levels of PC than the isogenic lines with the allele originally present in those varieties (Table 3).

The introduction of the DIC 6BS segment including the WNAC-B1a allele has been also shown to increase GPC when introduced into hexaploid wheat (Mesfin, A., R. C. Frohberg, and J. A. Anderson, Crop Science, 39:508-513 (1999), Khan, I. A., et al., Crop Science 40: 518-524 (2000)). Two additional isogenic lines of hexaploid wheat were developed by backcrossing the WNAC-B1 a allele into the high-protein HRS breeding line UC1041 and the low-protein HRS variety RSI5. The isogenic lines were developed by six backcross generations followed by selection of homozygous lines using molecular markers, and compared using a split plot design experiment with 20 replications in the field (Davis, Calif. 2004). In this experiment, the lines with the introgressed WNAC-B1a allele showed significantly higher levels of GPC than the isogenic lines with the allele originally present in those varieties. The incorporation of the DIC allele resulted in a grain protein content increase of 0.5% in UC1041 (from 14.2 to 14.7%, P=0.001) and of 1.6% in RSI5 (from 11.9% to 13.5%, P<0.0001). These results confirmed the potential of the WNAC-B1a allele from DIC to increase protein content in hexaploid wheat, both in lines of low and high-GPC.

The introduction of the DIC 6BS segment including the WNAC-B1a allele has been also shown to increase GPC when introduced into hexaploid wheat (Mesfin, A., R. C. Frohberg, and J. A. Anderson, Crop Science, 39:508-513 (1999); Khan, I. A., et al., Crop Science 40: 518-524 (2000)). Six additional isogenic lines of hexaploid wheat were developed by backcrossing the WNAC-B1 a allele into the high-protein HRS breeding lines and varieties UC1037, UC1041, Express, and Yecora Rojo and the low-protein HRS varieties Anza and RSI5. The isogenic lines were developed by six backcross generations followed by selection of homozygous lines using molecular markers. UC1041 and RSI5 were compared using a split plot design experiment with 20 replications in the field at Davis, Calif. (2004); and in an RCBD experiment with 10 replications at Buenos Airs, Argentina (2004). The other isogenic lines were tested only in the second location. In both experiments, the lines with the introgressed WNAC-B1 a allele showed significantly higher levels of GPC than the isogenic lines with the allele originally present in those varieties (Table 3). These results confirmed the potential of the WNAC-B1 a allele from DIC to increase protein content in hexaploid wheat, both in lines of low and high-GPC.

TABLE 3

Effect of the WNAC-B1b on GPC in different genetic backgrounds.

| VARIETY | Class | % Protein | | Relative Increase | Significance P value |
|---|---|---|---|---|---|
| | | Gpc-B1b | Gpc-B1a | | |
| | | Davis, CA 04 | | | |
| UC1041 | HRS | 14.2% | 14.7% | 3.5% | 0.0011 |
| RSI5 | HRS | 11.9% | 13.5% | 13.4% | <0.0001 |
| | | Argentina 04 | | | |
| UC1041 | HRS | 13.0% | 14.2% | 9.4% | <0.0001 |
| RSI5 | HRS | 10.9% | 12.0% | 10.1% | 0.0014 |
| Express | HRS | 12.2% | 13.2% | 8.0% | 0.0002 |
| UC1037 | HRS | 12.8% | 13.7% | 7.4% | 0.0075 |
| Anza | HRS | 10.8% | 11.8% | 8.5% | 0.0003 |
| Yecora Rojo | HRS | 12.4% | 13.1% | 5.1% | 0.0300 |
| Kofa | Durum | 12.9% | 14.2% | 10.6% | 0.0007 |
| UC1113 | Durum | 11.8% | 13.5% | 13.9% | <0.0001 |
| Average | | | | 9.0% | Increase GPC |

Davis, CA, USA (04): Split Plot design, 20 replications. Buenos Argentina 04: RCBD 10 replications.

Transcription profile of the candidate genes. The process of N remobilization in wheat is regulated at the leaves and ears rather than at the grain level (Bameix, A. J., and M. R. Guitman, J. Exp. Bot. 44:1607-1612 (1993), Martre, P., et al., Plant Physiol. 133:1959-1967 (2003)). The GPC-B1 gene, follows this general principle as demonstrated by the increased availability of soluble amino acids and proteins in the flag leaves of lines with the WNAC-B1 a allele relative to the lines with the WNAC-B1b allele. This increased concentration of proteins and amino acids in a form that can be readily transported to the grain provides a simple explanation to the increased grain protein content and lower straw residual N observed in the lines carrying the WNAC-B1a allele.

Since the differences in soluble proteins and amino acids were detected after anthesis but not in younger leaves, the candidate gene for the Gpc-B1 locus was expected to show some differences in the flag leaves around the time of anthesis.

No transcripts of UCW87 were observed in the flag leaves or other leaves of LDN or DIC at the time of anthesis. Transcripts were detected only with the UCW87 primers in developing seeds. These results indicate that UCW87 is not transcribed in the critical tissues and at the developmental stages expected for the GPC-B1 gene.

On the contrary WNAC-B1 showed the expected transcription profile based on the physiological experiments. Transcription of the WNAC-B1a, WNAC-B1b, WNAC-A1, and WNAC-B2 dramatically increased in the flag leaves after anthesis and during maturity (FIG. 2, lanes 3-5). No transcripts for the WNAC-1 genes were detected in earlier developmental stages in young green leaves. However a low level of transcripts was detected in senescing yellowing leaves (FIG. 2, lane 6).

Based on their natural allelic variation, transcription profiles, and the predicted function of orthologous genes in other plant species, UCW87 was eliminated as a candidate for the Gpc-B1 locus and concluded that WNAC-B1 is Gpc-B1.

EXAMPLE 2

Effect of the Allelic Variation at the Gpc-B1 Locus on Senescence

Allelic variation at the Gpc-B1 locus has other effects in addition to the observed difference in GPC. A field study comparing several RSLs carrying the WNAC-B1a allele with other carrying the WNAC-B1b allele (Davis, Calif., 2004, split plot design, 20 blocks) showed that the lines with the WNAC-B1 a senesce faster than the lines with the WNAC-B1b allele after anthesis. No significant differences were detected in ear emergence or time of anthesis between the two alleles indicating that the differences in maturation were due to differences in senescence/maturation rates. A few days after the first symptoms of senescence, the RSLs with the WNAC-B1 a allele showed a significantly higher percent of yellow peduncles (P<0.001) and a significantly lower water content in the spikes (P<0.001) than the lines with the WNAC-B1b allele. Lines with WNAC-B1a allele had an average humidity of 25.9% versus lines with LDN allele that had average of 29.5%.

The acceleration in the senescence process in the plants with the WNAC-B1a allele is consistent with the higher levels of soluble proteins and amino acids observed in the flag leaves of the plants with this allele relative to the plants with the WNAC-B1b allele. Soluble proteins are the results of degradation of structural or storage proteins into a form that can be transported to the grain. These results suggest that the WNAC-1 gene plays a significant role in the regulation of the senescence process. It is possible, that the observed difference in grain protein content is one of the multiple effects generated by the differences in senescence rates.

The *Arabidopsis* NAC genes more closely related to the WNAC-B1 gene have been shown to be upregulated during dark induced (Lin J.-F., S.-H. Wu, *The Plant Journal* 39:612-628 (2004)) and natural senescence (Guo, Y., *Plant Cell and Environment* 27:521-549 (2004)) in leaves. The initiation of WNAC-1 transcription in the flag leaves after anthesis is also consistent with the proposed role in the regulation of senescence.

The RSLs tested in the senescence experiment included the critical lines RSL28 and RSL121 facilitating a precise mapping of the difference in senescence. The locus regulating the differences in senescence was mapped between flanking loci Xuhw89 and Xucw71 (Table 1) and completely linked to the WNAC-1 gene. It appears that the different amounts of functional WNAC-1 protein generated by the frame shift mutation were responsible for both the differences in maturity and the differences in GPC content. In conclusion, the modulation of the transcript levels of the WNAC-B1 gene can be used to alter both grain protein content and also the rate of leaf senescence in wheat and other cereals.

EXAMPLE 3

WNAC-B1 Orthologues in Rice and Maize

WNAC-B1 Orthologue in Rice.

The complete genomic sequence of rice was searched to identify the closest homologue of WNAC-B1 in rice (SEQ ID NOS:28 and 29). One rice NAC protein was identified (OsNAC) that had 98% similarity to WNAC-B1 at the protein level within the NAC domain (115 of 117 amino acid residues). This high level of similarity dropped to 84% with the second highest score in the blast search (OsNAC-A). FIG. 4 displays a multiple sequence alignment of the 75 NAC proteins previously reported by Ooka, H., et al., *DNA Research* 10:239-247 (2003) and the wheat WNAC-B1 protein, followed by a phylogenetic analysis (neighbor-joining method). OsNAC and WNAC-B1 clustered together, while OsNAC-A and all the other rice NAC proteins were located on separate branches (complete tree not shown).

In addition, the promoter region of the WNAC-B1 and OsNAC genes was analyzed to find common regulatory elements. A 40-bp segment with perfect conservation between OsNAC, WNAC-B1 and homoeoallele WNAC-A1 was found. Within this conserved segment, an ABRE-like motif (ACGTG) was identified. This motif has previously been shown to be required for senescence responsive gene expression in the erd1 promoter of *Arabidopsis* (Simpson et al., 2003). This study also identified an ACG motif 40 bp downstream that was required (along with the ABRE-like motif) to promote senescence associated erd1 expression. These two motifs are perfectly conserved and separated by similar distance (38-40 bp) in the rice, wheat and barley promoters for the WNAC-B1 orthologues. The two presented sources of evidence strongly support the hypothesis that OsNAC is the single orthologue of WNAC-B1 in rice.

The rice orthologue OsNAC is located on chromosome 7, which is colinear with wheat chromosome 2. WNAC-B1 maps to wheat chromosome 6, but has a paralogous copy (WNAC-B2) on wheat chromosome 2. This gene, WNAC-B2, is in perfect colinearity with the rice OsNAC gene and therefore, the original gene that was cloned from wheat chromosome 6 is product of a duplication event that occurred in wheat, but was absent in rice. A QTL for rice soluble protein content in senescing leaf blade was mapped near marker R1357 which is located 1.6 cM proximal to OsNAC (Obara et al. 2001), while Tan et al (2001) mapped a QTL for rice GPC 3.6 cM distal to OsNAC. This colinear location between the wheat and rice NAC genes, along with the colocalization of equivalent QTLs in this region, further supports the hypothesis that OsNAC and WNAC-B1 are orthologues that share a similar function.

Additional evidence is provided by the fact that OsNAC shares similar expression patterns as WNAC-B1 (FIG. 5), with no detectable expression in any tissue until the days prior to anthesis. An electronic search for EST sequences of OsNAC before anthesis or in other tissues was negative, with the only EST identified belonging to a library developed from leaf tissue after anthesis. Taking together the conserved promoter motifs, the sequence similarity, their colinear location on the wheat and rice chromosomes and their similar expression profiles, these results strongly suggest that rice OsNAC is the unique orthologue of wheat WNAC-B1.

WNAC-B1 Orthologue in Maize.

The latest version of the maize genome assembly at the Plant Genome Database (http://www.plantgdb.org) was searched. This search identified a GSS contig (SEQ ID NOS: 30 and 31) that encodes a protein (ZmNAC) which has 100% similarity to WNAC-B1 at the protein level within the NAC domain (117 of 117 amino acid residues). This high level of conservation within the NAC domain is even higher than that found for the rice orthologue (OsNAC) providing evidence that this protein (ZmNAC) is an orthologue of the wheat WNAC-B1 protein. The possibility for other WNAC-B1 orthologues in maize exists, although ZmNAC is the most likely true orthologue to WNAC-B1 due to its high conservation within the functional NAC domain.

EXAMPLE 4

Effect of the Allelic Variation at the WNAC-B1 Locus on Senescence

Figure 6A:
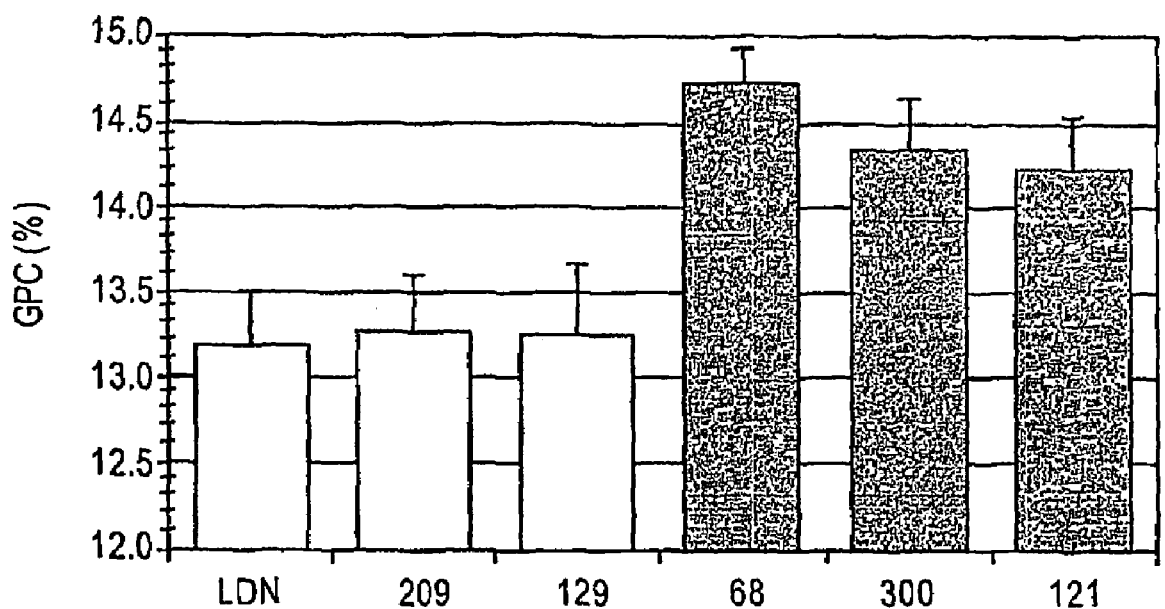
FIG. 6 depicts: a) Grain protein content of RSLs (209, 129, 300 and 121) and control lines (LDN and 65). RSLs 209 and 129 were similar to the low protein control LDN and were assigned the WNAC-B1b low protein allele (black bars), whereas RSLs 300 and 121 were similar to the high protein control RSL 65 and were assigned the WNAC-B1a high protein allele (grey bars). b) Chlorophyll content profile (SPAD units) from 13 to 35 DAA. Grey line with open diamonds represents lines with the WNAC-B1a allele and black line with solid squares represents lines with the WNAC-B1b allele. Error bars are standard errors of the means.
Figure 6B:
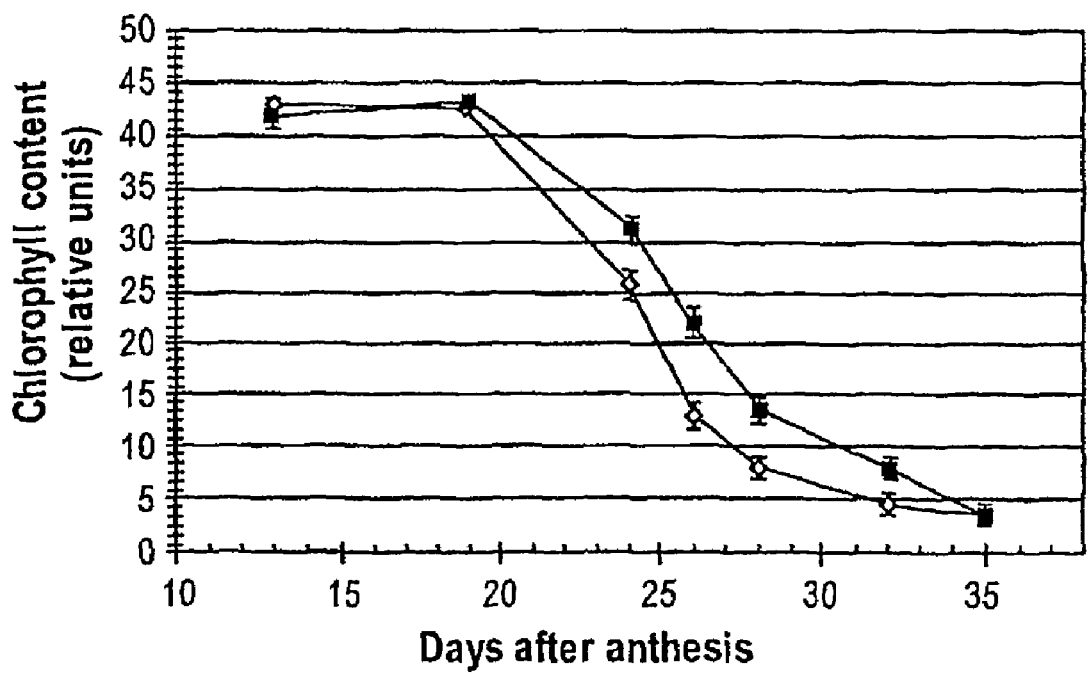
Figure 7A:
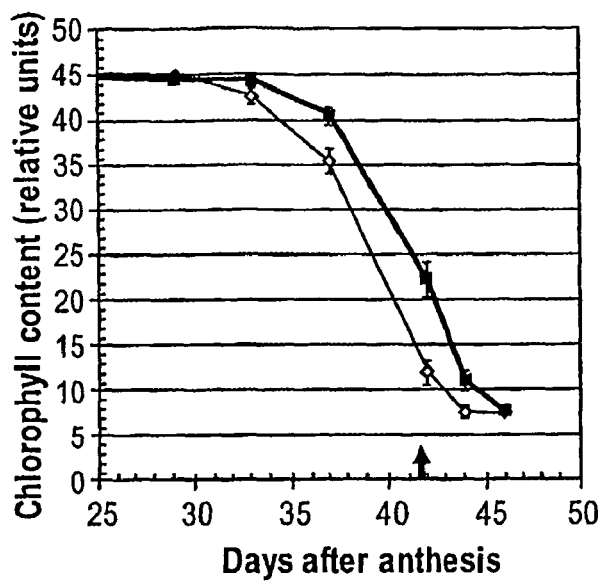
FIG. 7 depicts the effect of the WNAC-B1a allele on the chlorophyll content profile of isogenic lines of hexaploid wheat Anza (a), RSI5 (b), UC1041 (c) and tetraploid wheat Kofa (d). Chlorophyll content is measured in relative SPAD units from 20-25 DA until complete yellowing (50-60 DAA). Black lines with solid squares represent the original recurrent parent and grey lines with open diamonds represent the corresponding isogenic line with the WNAC-B1a allele. Significant differences (P<0.05) between isogenic pairs are represented by arrows on the corresponding date. Error bars are standard errors of the means.
Figure 7B:
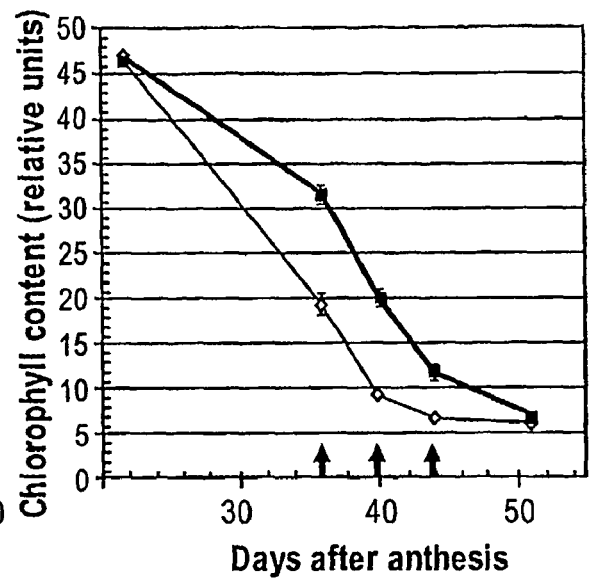
Figure 7C:
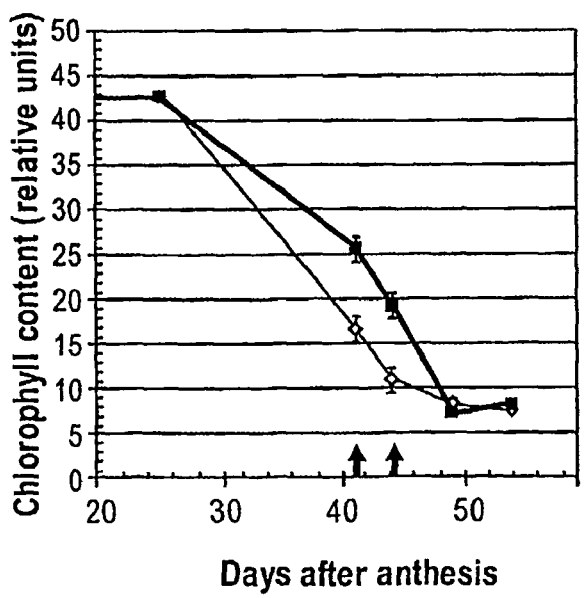
Figure 7D:
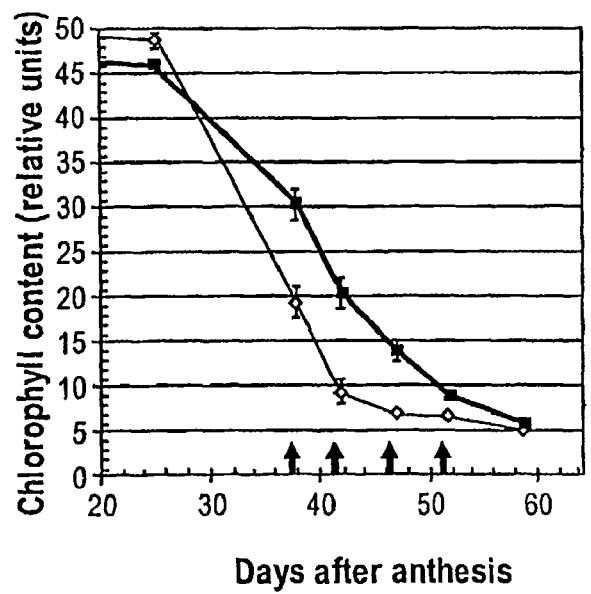

To further assess the senescence phenotype, a time-course of chlorophyll content in the flag leaves of plants grown under field conditions was established (FIG. 6b). Plants with the WNAC-B1a allele underwent earlier chlorophyll degradation than plants with the WNAC-B1b allele, starting 19 days after anthesis (DAA). Significant differences in flag leaf chlorophyll content were detected in the measurements performed at 24 DAA ($P<0.006$), 26 DAA ($P<0.002$), 28 DAA ($P<0.001$) and 32 DAA ($P<0.001$). Measurements for both alleles converged when the flag leaves were completely yellow (35 DAA). No differences were detected between RSLs and controls in the time of anthesis. The average GPC increase in the RSLs with the WNAC-B1a allele relative to the lines with the WNAC-B1b allele was 12 g/kg ($P<0.001$, FIG. 2a), confirming that the conditions were appropriate for the expression of the differences attributable to the Gpc-B1 locus.

EXAMPLE 5

Effect of WNAC-B1 on Senescence in Tetraploid and Hexaploid Isogenic Lines

The effect of WNAC-B1 in different genetic backgrounds was tested in three hexaploid (Anza, RSI5, and UC1041) and one tetraploid (Kofa) pairs of isogenic lines ($BC_6F_3$). The presence of the WNAC-B1a allele significantly increased GPC ($P<0.01$) in the three hexaploid isogenic lines (Anza, RSI5, UC1041) with respect to the recurrent parent by an average of 12.1 g $kg^{-1}$. The tetraploid line Kofa carrying the WNAC-B1a allele showed a smaller increase of GPC (3.3 g $kg^{-1}$, $P=0.26$) relative to the recurrent parent (a high-protein content variety), and the differences were not significant in this experiment.

In all four genetic backgrounds, the chlorophyll degradation time-course (FIG. 7) showed more rapid chlorophyll degradation in the lines with the WNAC-B1a allele than in the isogenic lines with the recurrent parent allele. These differences were not originated in flowering time variability since the lines for each isogenic pair reached anthesis at the same time. During the first 20-30 DAA no significant differences in chlorophyll content were detected in the flag leaves, but after that, chlorophyll degradation was faster in the isogenic lines carrying the WNAC-B1a allele (FIG. 7, grey lines with open squares) as compared with the original recurrent parent (FIG. 7, black lines with full squares). These differences were similar across genotypes, with the isogenic lines carrying the WNAC-B1a allele being on average 3-4 days more advanced in their senescence process than the corresponding recurrent parent. The significant differences in chlorophyll content ($P<0.05$, indicated by arrows in FIG. 7) were maintained until the flag leaves of the isogenic pairs approached complete yellowing.

In addition to chlorophyll degradation, the progression of grain moisture content was measured leading to the observation that the isogenic lines with the WNAC-B1a allele presented significantly lower grain moisture content than the isogenic lines with the recurrent parent allele ($P<0.05$, FIG. 4). Although isogenic lines of UC1041 were not included in FIG. 8, they also showed significant differences in grain moisture content ($P=0.02$) between the recurrent UC1041 line (20.2% moisture content) and the UC1041 isogenic line carrying the WNAC-B1a allele (8.9% moisture content). These results indicate that the more rapid chlorophyll degradation in the isogenic lines carrying the WNAC-B1a allele was associated with a shorter grain filling period in all four genotypes. This result is consistent with those observed in the tetraploid recombinant substitution lines (FIG. 6).

EXAMPLE 6

Figure 13:
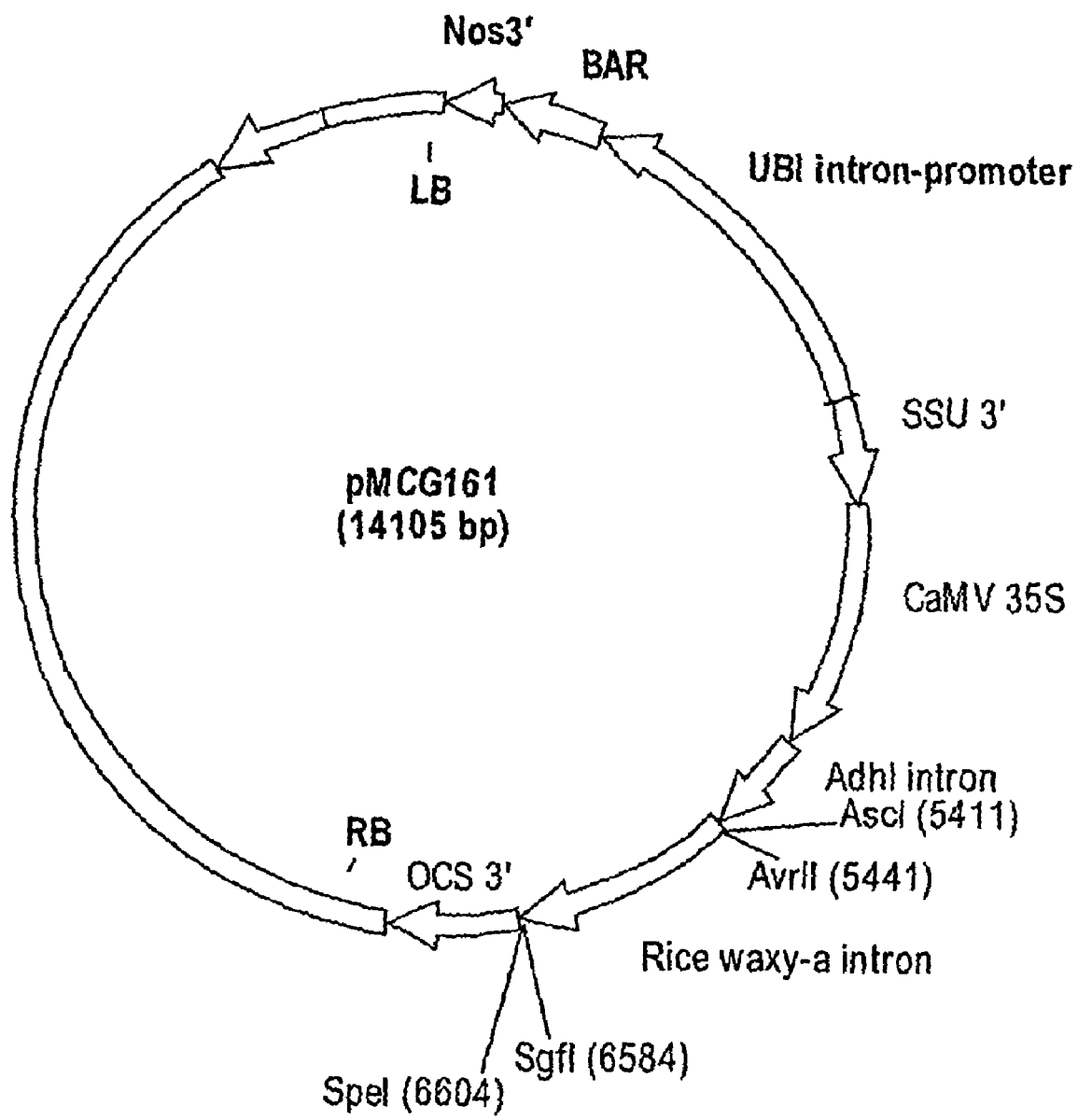
FIG. 13 depicts the vector map of pMCG161

Modulation of Senescence by Altering the Expression Levels of WNAC Using a Transgenic Approach The RNAi construct was made in the binary vector pMCG161 provided by V. Chandler and built using pCAMBIA 1200. The pMCG161 vector is depicted in FIG. 13 and described on The Plant Chromatin Database website accessible at http://www.chromdb.org/. This vector contains a cassette designed for making inverted repeat transcripts of a gene, flanking loop, which should efficiently produce a double stranded RNA. Expression of the transgene is driven by the 35S promoter followed by the Adh1 intron. A 475-bp construct was made from the functional WNAC-A1 (832-bp to TGA stop codon plus 88-bp from the 5' UTR) in the sense orientation between restriction sites AscI-AvrII and in antisense orientation between restriction sites SgfI-SpeI. The cloned region excluded the NAC domain to avoid silencing of other NAC genes. The engineered plasmid was co-transformed with UBI:BAR into immature embryos of Bobwhite, a hard white spring wheat, by electrophoresis.

Figure 9A:
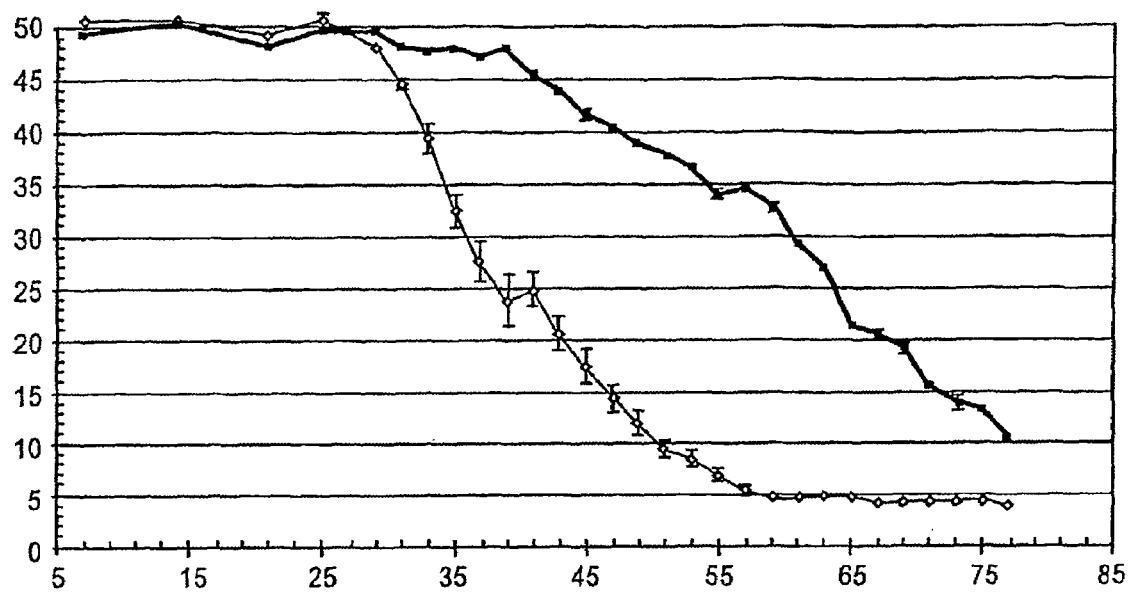
FIG. 9 depicts the effects of altering the expression levels of WNAC on different senescence phenotypes. a) Chlorophyll content profile (SPAD units). Black line with solid squares represents positive transgenic lines with reduced WNAC expression (n=25) and the gray line with open diamonds represents control lines (n=10). b) DAA for complete yellowing of peduncle. c) DAA for the main spike to be completely dry. In b) and c) black bars represent positive transgenic lines with reduced WNAC expression and the striped patterned bars represent control lines. Error bars are standard errors of the means.
Figure 9B:
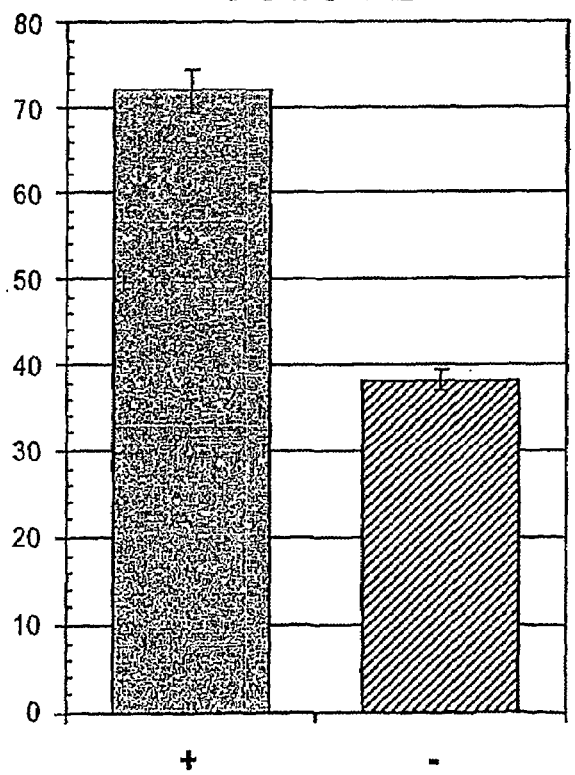
Figure 9C:
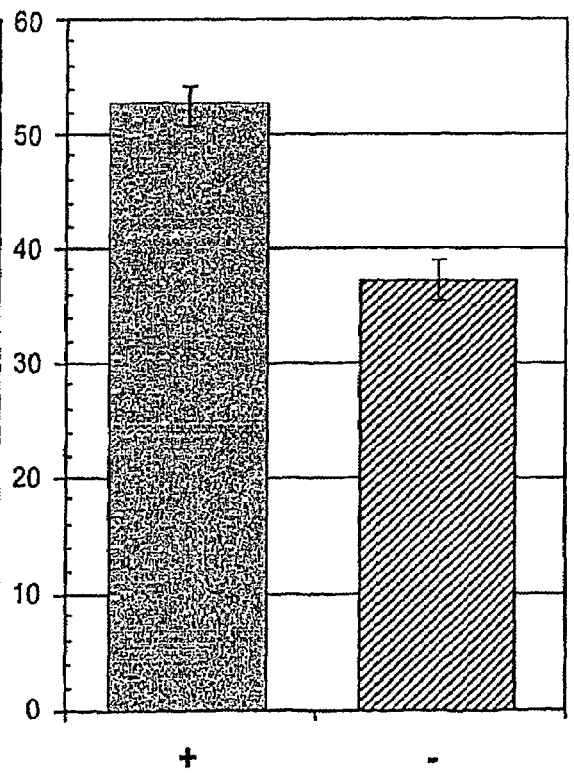
Figure 10:
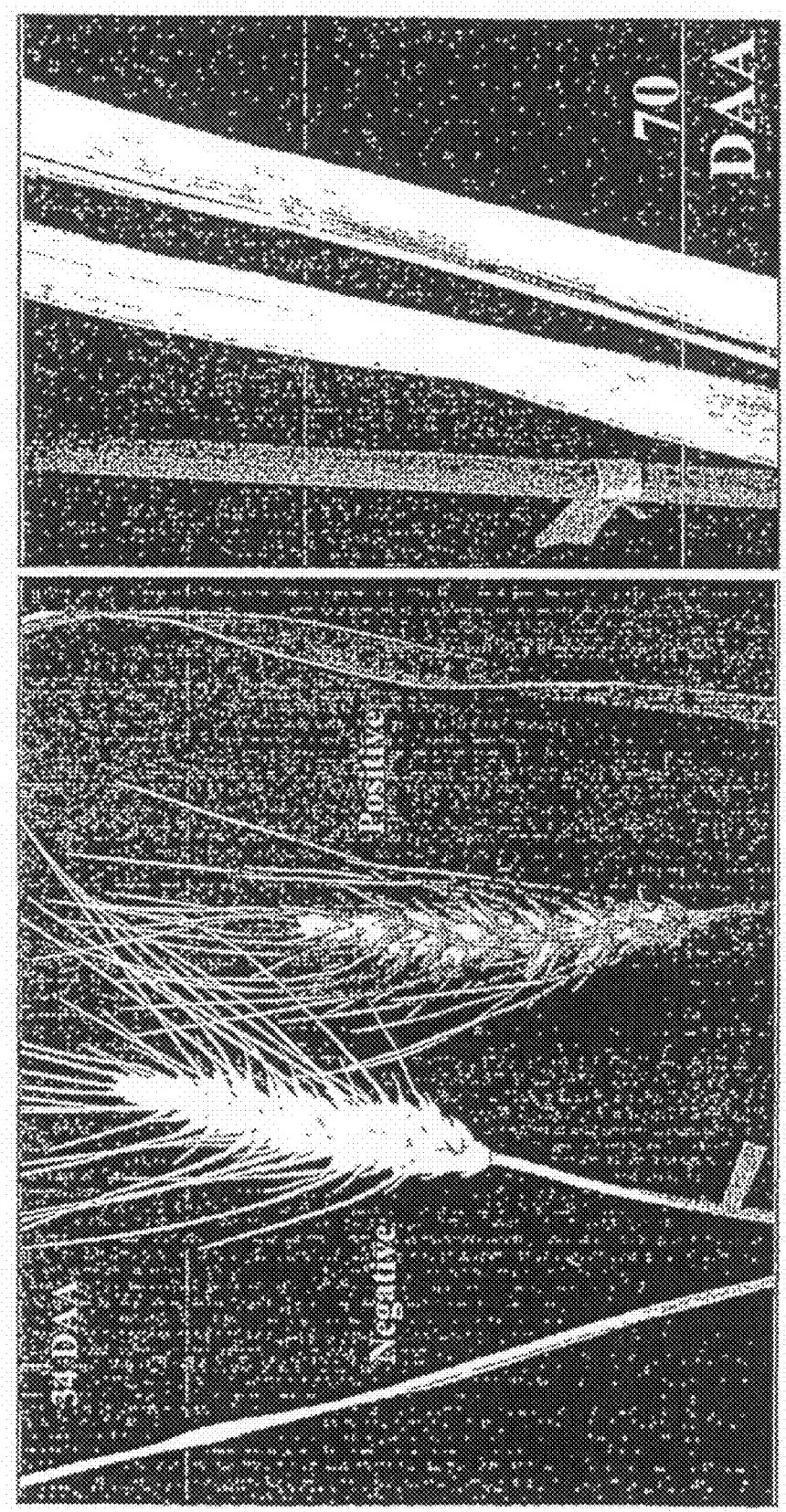
FIG. 10 depicts spike, flag leaf and peduncle color comparisons between positive and negative (control) plants at 34 and 70 DAA for event L19-54. Left panel, positive plant has green flag leaf, peduncle and immature grains compared to a completely senescence control plant. Right panel, at 70 DAA, the positive plant still has a green peduncle and flag leaf is dry but green. Spike (not shown) is completely dry.

To validate WNAC-B1 as the gene responsible for the differences in senescence observed in the RSLs (FIG. 6a), an RNAi construct was designed that was expected to decrease transcript levels for the WNAC copies on all three genomes (A, B and D), as well as on homologous group 2. A delay in senescence was expected to result in transgenic lines with reduced expression of the WNAC genes, similar to the delay of 4-5 days seen in RSLs with the non-functional WNAC-B1b allele (FIG. 6a). Two independent T, transgenic events were generated (L19-54 and L23-119) that showed a delay in senescence with respect to the non-transgenic controls (FIG. 9). Three different phenotypes were measured to determine their senescence profile: flag leaf chlorophyll degradation, DAA when the peduncle was completely yellow and DAA for the main spike to be completely dry. Plants that were positive for the RNAi construct from event L19-54 presented a delay in flag leaf chlorophyll degradation at 24 days with respect to the control lines that were negative for the transgene (FIG. 9a). These same positive plants had a delay of over 30 days to reach complete yellowing of the peduncle and a two week delay in spike yellowing (FIGS. 9b, c). Interestingly, when the flag leaf and peduncle of the positive plants dried, in many cases they still conserved chlorophyll, (FIG. 10b). This suggests a role of WNAC in chlorophyll degradation in both flag leaf and peduncle, among other senescence related processes. Positive plants had similar physical appearance compared to control plants, produced equal number of tillers and presented no differences in time to anthesis. Similar results were obtained from the second positive event, L23-119.

EXAMPLE 7

Figure 11:
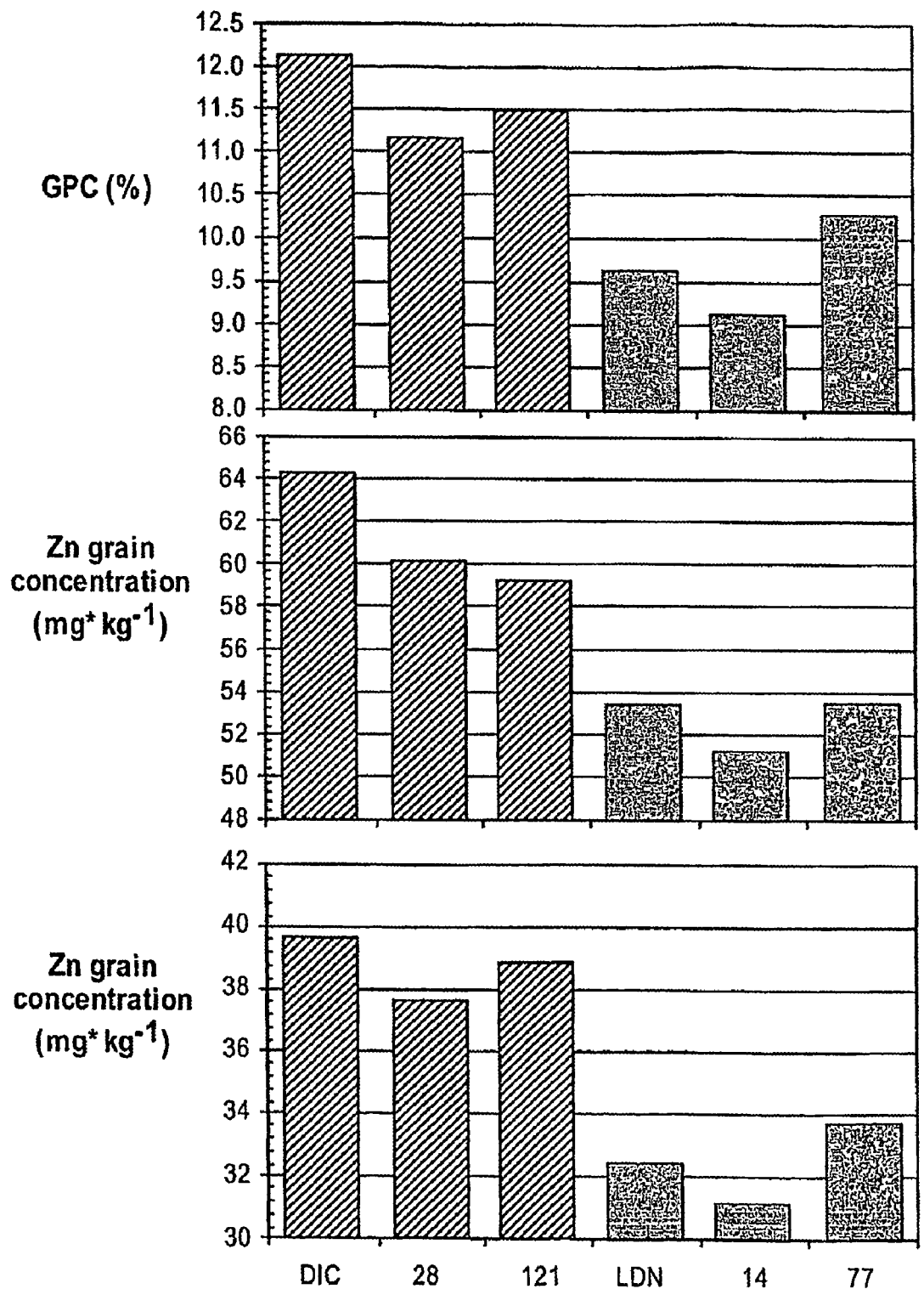
FIG. 11 depicts the effect of WNAC-B1 on protein, Zn and Fe content in the grain of RSLs (28, 121, 14 and 77) and control lines (LDN and DIC). RSLs 14 and 77 were similar to the low protein control LDN and were assigned the WNAC-B1b low protein allele (black bars), whereas RSLs 28 and 121 were similar to the high protein control DIC and were assigned the WNAC-B1a high protein allele (striped pattern bars).

Effect of the Allelic Variation at the WNAC-B1 Locus on Zn and Fe Concentration in the Grain Allelic variation at the WNAC-B1 locus has other effects in addition to the observed difference in GPC and senescence. A field study by Distelfeld A. et al., *New Phytologist*, 169:753-763 (2006) comparing several RSLs carrying the WNAC-B1a allele with other carrying the WNAC-B1b allele (Haifa, Israel, 2004-2005) showed that the lines with the WNAC-B1a accumulate 10-20% higher Zn and Fe concentration in the grain compared to the lines with the WNAC-B1b allele (FIG. 11). The RSLs with the WNAC-B1a allele showed a significantly higher GPC (P<0.01), Zn concentration (P<0.01) and Fe concentration (P<0.01) than the lines with the WNAC-B1b allele. Lines with WNAC-B1a allele had an average Zn concentration of 61 mg/kg versus the lines with the WNAC-B1b allele that had an average of 56 mg/kg. In this same manner, lines carrying the WNAC-B1a allele had an average grain Fe concentration of 39 mg/kg versus an average of 34 mg/kg in the lines with the WNAC-B1b allele. The expected differences in GPC and senescence were also observed in this experiment. Lines with the WNAC-B1a allele increased GPC by 17 g/kg and had an acceleration in senescence of 3 days (peduncle yellowing) with respect to lines with the WNAC-B1b allele.

The increased accumulation of Zn and Fe in the grain of plants with the WNAC-B1a allele is consistent with the proposed role of WNAC-B1 in modulating senescence and therefore nutrient translocation. Physiological studies concluded that the presence of the WNAC-B1a allele resulted in a more efficient N remobilization from the senescing leaves to the ears during grain filling. This same mechanism may be responsible for the increased Zn and Fe accumulation in the grain. These results suggest that WNAC-B1 plays a significant role in the regulation of the senescence and through this, in the nutrient remobilization process of not only protein, but of other micronutrients such as Zn and Fe, as well.

The RSLs tested in the Zn and Fe experiment included the critical lines RSL28 and RSL121 facilitating a precise mapping of the difference in grain mineral concentration. The locus regulating these differences was mapped within a 250-kb region and completely linked to the WNAC-1 gene. Therefore, the different amounts of functional WNAC-B1 protein generated by the frame shift mutation appears responsible for the differences in senescence, GPC, Zn and Fe content in the grain.

EXAMPLE 8

Transcription Profile of Candidate Genes

Figure 12:
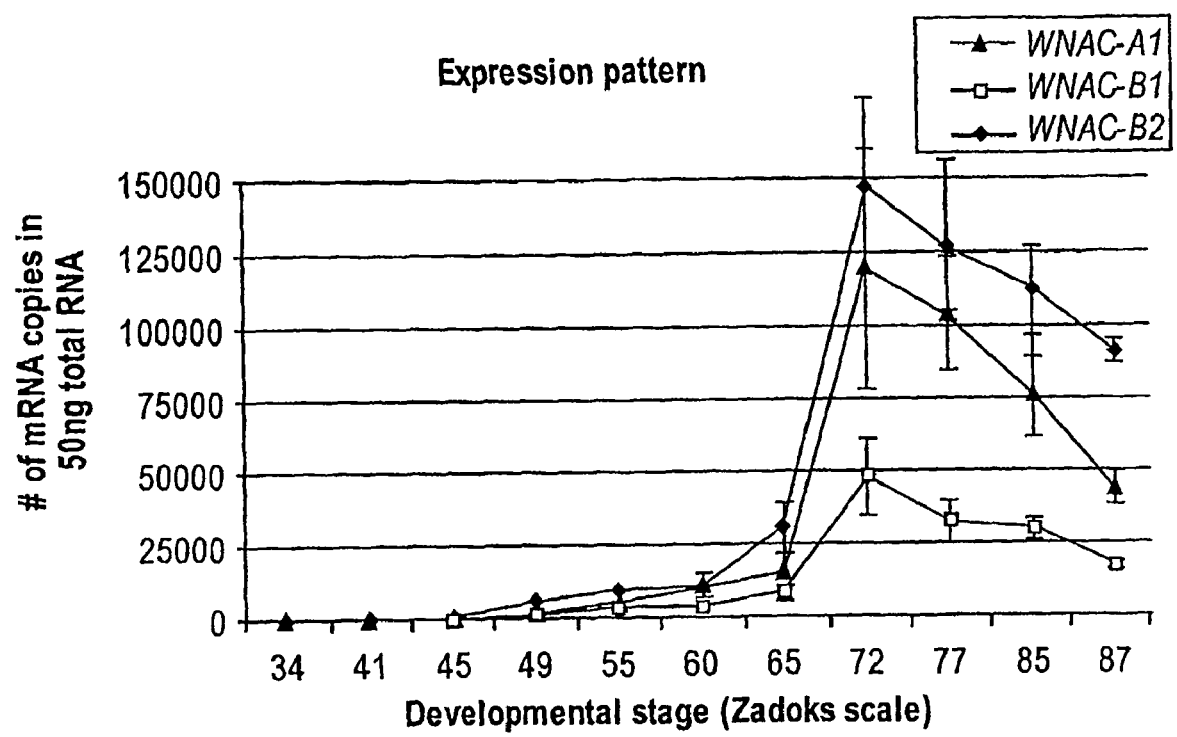
FIG. 12 depicts transcription levels of WNAC-A1, WNAC.-B1, and WNAC-B2 in wheat leaves at different stages of development using real-time reverse transcription PCR (quantitative).

Transcription of WNAC-A1, WNAC-B1, and WNAC-B2 was first detected in leaf samples from Zadoks 45 stage, 10 days before anthesis and dramatically increased in the flag leaves after anthesis (Zadoks 65 stage) and during maturity (FIG. 12). The highest transcription level was detected at Zadoks 72 stage, 10 days after anthesis. At this point the estimated mRNA copy number in 50 ng of RNA was significantly higher in WNAC-A1 (119,442) and WNAC-B2 (146,679) as compared to WNAC-B1 (47,867). From this point forward, the mRNA levels of WNAC-A1, WNAC-B1, and WNAC-B2 decreased but remained present in the leaves until complete senescence (Zadoks 87). In addition, expression of the WNAC genes was detected in green spikes and peduncles.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

What is claimed is:

1. A transgenic plant comprising a recombinant nucleic acid encoding a plant NAC protein, wherein said nucleic acid encodes a NAC protein which is at least 95% identical to the amino acid sequence depicted in SEQ ID NO: 2.

2. The transgenic plant of claim 1 wherein said NAC protein is SEQ ID NO: 2.

3. The transgenic plant of claim 1 wherein said nucleic acid is SEQ ID NO:1.

4. The transgenic plant of claim 1 wherein said nucleic acid is operably linked to a heterologous promoter.

5. The transgenic plant of claim 1 wherein said plant is selected from the group consisting of wheat, rice, or maize.

6. An isolated nucleic acid molecule comprising a recombinant expression cassette comprising a nucleic acid sequence encoding a NAC protein which is at least 95% identical to the amino acid sequence depicted in SEQ ID NO: 2.

7. A method of increasing grain protein content or of delaying senescence in a cereal plant, the method comprising introducing into the plant a recombinant expression cassette comprising the nucleic acid of claim 6.

8. The method of claim 7, wherein the NAC nucleic acid is SEQ ID NO: 1.

9. The method of claim 7, further comprising selecting plants exhibiting delayed timing of senescence onset compared to the timing of senescence onset in a control plant.

10. The method of claim 7, further comprising selecting plants exhibiting higher grain protein content compared to a control plant.

11. The nucleic acid molecule of claim 6 wherein said NAC protein is SEQ ID NO: 2.

12. The nucleic acid molecule of claim 6 wherein said nucleic acid sequence is SEQ ID NO:1.

13. The nucleic acid molecule of claim 6 wherein said nucleic acid sequence is operably linked to a heterologous promoter.

14. A method of delaying senescence in a wheat plant, the method comprising inhibiting expression of an endogenous WNAC gene in the plant, wherein the endogenous WNAC gene encodes a protein at least 95% identical to SEQ ID NO: 2.

15. The method of claim 14, wherein the method is carried out by introducing into the plant a construct encoding an interfering RNA molecule.

* * * * *